US010907154B2

(12) United States Patent
Bestwick et al.

(10) Patent No.: US 10,907,154 B2
(45) Date of Patent: *Feb. 2, 2021

(54) EXON SKIPPING COMPOSITIONS FOR TREATING MUSCULAR DYSTROPHY

(71) Applicant: Sarepta Therapeutics, Inc., Cambridge, MA (US)

(72) Inventors: Richard K. Bestwick, Bend, OR (US); Diane Elizabeth Frank, Seattle, WA (US)

(73) Assignee: Sarepta Therapeutics, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/220,799

(22) Filed: Dec. 14, 2018

(65) Prior Publication Data

US 2019/0177724 A1    Jun. 13, 2019

Related U.S. Application Data

(63) Continuation of application No. 15/431,468, filed on Feb. 13, 2017, now abandoned, which is a continuation of application No. 14/942,629, filed on Nov. 16, 2015, now abandoned, which is a continuation of application No. 14/213,607, filed on Mar. 14, 2014, now Pat. No. 9,217,148.

(60) Provisional application No. 61/784,547, filed on Mar. 14, 2013.

(51) Int. Cl.
*C12N 15/11* (2006.01)
*C12N 15/113* (2010.01)
*A61K 47/60* (2017.01)
*A61K 31/713* (2006.01)
*A61K 47/64* (2017.01)

(52) U.S. Cl.
CPC .......... *C12N 15/113* (2013.01); *A61K 31/713* (2013.01); *A61K 47/60* (2017.08); *A61K 47/6455* (2017.08); *C12N 15/111* (2013.01); *C12N 2310/11* (2013.01); *C12N 2310/3233* (2013.01); *C12N 2310/33* (2013.01); *C12N 2310/351* (2013.01); *C12N 2310/3513* (2013.01); *C12N 2310/3535* (2013.01); *C12N 2320/30* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 5,034,506 A | 7/1991 | Summerton et al. | |
| 5,138,045 A | 8/1992 | Cook et al. | |
| 5,142,047 A | 8/1992 | Summerton et al. | |
| 5,149,797 A | 9/1992 | Pederson et al. | |
| 5,166,315 A | 11/1992 | Summerton et al. | |
| 5,185,444 A | 2/1993 | Summerton et al. | |
| 5,190,931 A | 3/1993 | Inouye | |
| 5,217,866 A | 6/1993 | Summerton et al. | |
| 5,508,337 A | 4/1996 | Summerton et al. | |
| 5,521,063 A | 5/1996 | Summerton et al. | |
| 5,627,274 A | 5/1997 | Kole et al. | |
| 5,665,593 A | 9/1997 | Kole et al. | |
| 5,698,685 A | 12/1997 | Summerton et al. | |
| 5,801,154 A | 9/1998 | Baracchini et al. | |
| 5,869,252 A | 2/1999 | Bouma et al. | |
| 5,892,023 A | 4/1999 | Pirotzky et al. | |
| 5,916,808 A | 6/1999 | Kole et al. | |
| 5,976,879 A | 11/1999 | Kole et al. | |
| 6,153,436 A | 11/2000 | Hermonat et al. | |
| 6,210,892 B1 | 4/2001 | Bennett et al. | |
| 6,312,900 B1 | 11/2001 | Dean et al. | |
| 6,391,636 B1 | 5/2002 | Monia | |
| 6,451,991 B1 | 9/2002 | Martin et al. | |
| 6,653,466 B2 | 11/2003 | Matsuo | |
| 6,653,467 B1 | 11/2003 | Matsuo et al. | |
| 6,656,732 B1 | 12/2003 | Bennett et al. | |
| 6,727,355 B2 | 4/2004 | Matsuo et al. | |
| 6,784,291 B2 | 8/2004 | Iversen et al. | |
| 6,806,084 B1 | 10/2004 | Debs et al. | |
| 7,001,761 B2 | 2/2006 | Xiao | |
| 7,070,807 B2 | 7/2006 | Mixson | |
| 7,163,695 B2 | 1/2007 | Mixson | |
| 7,250,289 B2 | 7/2007 | Zhou | |
| 7,314,750 B2 | 1/2008 | Zhou | |
| 7,468,418 B2 | 12/2008 | Iversen et al. | |
| 7,534,879 B2 | 5/2009 | van Deutekom | |
| 7,655,785 B1 | 2/2010 | Bentwich | |
| 7,655,788 B2 | 2/2010 | Khvorova et al. | |
| 7,807,816 B2 | 10/2010 | Wilton et al. | |
| 7,902,160 B2 | 3/2011 | Matsuo et al. | |

(Continued)

FOREIGN PATENT DOCUMENTS

AU        780517        11/2001
AU    2003284638 A1     6/2004

(Continued)

OTHER PUBLICATIONS

*Telios Pharms., Inc.* v. *Merck KgaA*, No. 96-1307, 1998 WL 35272018 (S.D. Cal. Nov. 18, 1998), 11 pages (Exhibit No. 2153 flied in interference 106013 on Oct. 29, 2015).

(Continued)

*Primary Examiner* — Dana H Shin

(74) *Attorney, Agent, or Firm* — Sterne, Kessler, Goldstein and Fox P.L.L.C.

(57) ABSTRACT

Antisense molecules capable of binding to a selected target site in the human dystrophin gene to induce exon 44 skipping are described.

4 Claims, 6 Drawing Sheets

Specification includes a Sequence Listing.

(56) References Cited

U.S. PATENT DOCUMENTS

| | | |
|---|---|---|
| 7,960,541 B2 | 6/2011 | Wilton et al. |
| 7,973,015 B2 | 7/2011 | van Ommen et al. |
| 8,084,601 B2 | 12/2011 | Popplewell et al. |
| 8,232,384 B2 | 7/2012 | Wilton et al. |
| 8,324,371 B2 | 12/2012 | Popplewell et al. |
| 8,361,979 B2 | 1/2013 | Aartsma-Rus et al. |
| 8,436,163 B2 | 5/2013 | Iversen et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,461,325 B2 | 6/2013 | Popplewell et al. |
| 8,476,423 B2 | 7/2013 | Wilton et al. |
| 8,486,907 B2 | 7/2013 | Wilton et al. |
| 8,501,703 B2 | 8/2013 | Bennett et al. |
| 8,501,704 B2 | 8/2013 | Mourich et al. |
| 8,524,676 B2 | 9/2013 | Stein et al. |
| 8,524,880 B2 | 9/2013 | Wilton et al. |
| 8,535,147 B2 | 9/2013 | Weller et al. |
| 8,552,172 B2 | 10/2013 | Popplewell et al. |
| 8,592,386 B2 | 11/2013 | Mourich et al. |
| 8,618,270 B2 | 12/2013 | Iversen et al. |
| 8,624,019 B2 | 1/2014 | Matsuo et al. |
| 8,637,483 B2 | 1/2014 | Wilton et al. |
| 8,697,858 B2 | 4/2014 | Iversen |
| 8,741,863 B2 | 6/2014 | Moulton et al. |
| 8,759,307 B2 | 6/2014 | Stein et al. |
| 8,759,507 B2 | 6/2014 | Van Deutekom |
| 8,779,128 B2 | 7/2014 | Hanson et al. |
| 8,785,407 B2 | 7/2014 | Stein et al. |
| 8,785,410 B2 | 7/2014 | Iversen et al. |
| 8,835,402 B2 | 9/2014 | Kole et al. |
| 8,865,883 B2 | 10/2014 | Sazani et al. |
| 8,871,918 B2 | 10/2014 | Sazani et al. |
| 8,877,725 B2 | 11/2014 | Iversen et al. |
| 8,895,722 B2 | 11/2014 | Iversen et al. |
| 8,906,872 B2 | 12/2014 | Iversen et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 9,175,286 B2 | 11/2015 | Wilton et al. |
| 9,217,148 B2 | 12/2015 | Bestwick et al. |
| 9,228,187 B2 | 1/2016 | Wilton et al. |
| 9,234,198 B1 | 1/2016 | Sazani et al. |
| 9,249,416 B2 | 2/2016 | Wilton et al. |
| 9,416,361 B2 | 8/2016 | Iversen et al. |
| 9,422,555 B2 | 8/2016 | Wilton et al. |
| 9,434,948 B2 | 9/2016 | Sazani et al. |
| 9,441,229 B2 | 9/2016 | Wilton et al. |
| 9,447,415 B2 | 9/2016 | Wilton et al. |
| 9,447,416 B2 | 9/2016 | Sazani et al. |
| 9,447,417 B2 | 9/2016 | Sazani et al. |
| 9,453,225 B2 | 9/2016 | Sazani et al. |
| 9,505,058 B2 | 11/2016 | Kaye |
| 9,605,262 B2 | 3/2017 | Wilton et al. |
| 9,758,783 B2 | 9/2017 | Wilton et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0110819 A1 | 8/2002 | Weller et al. |
| 2002/0156235 A1 | 10/2002 | Manoharan et al. |
| 2003/0166588 A1 | 9/2003 | Iversen et al. |
| 2003/0224353 A1 | 12/2003 | Stein et al. |
| 2003/0235845 A1 | 12/2003 | van Ommen et al. |
| 2004/0248833 A1 | 12/2004 | Emanuele et al. |
| 2004/0254137 A1 | 12/2004 | Ackermann et al. |
| 2004/0266720 A1 | 12/2004 | Iversen et al. |
| 2005/0026164 A1 | 2/2005 | Zhou |
| 2005/0048495 A1 | 3/2005 | Baker et al. |
| 2005/0153935 A1 | 7/2005 | Iversen et al. |
| 2006/0099616 A1 | 5/2006 | van Ommen et al. |
| 2006/0147952 A1 | 7/2006 | van Ommen et al. |
| 2006/0148740 A1 | 7/2006 | Platenburg |
| 2006/0287268 A1 | 12/2006 | Iversen et al. |
| 2007/0037165 A1 | 2/2007 | Venter et al. |
| 2007/0082861 A1 | 4/2007 | Matsuo et al. |
| 2007/0265215 A1 | 11/2007 | Iversen et al. |
| 2008/0191463 A1 | 8/2008 | Weller et al. |
| 2008/0200409 A1 | 8/2008 | Wilson et al. |
| 2008/0209581 A1 | 8/2008 | van Ommen et al. |
| 2009/0076246 A1 | 3/2009 | van Deutekom |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0228998 A1 | 9/2009 | van Ommen et al. |
| 2009/0269755 A1 | 10/2009 | Aartsma-Rus et al. |
| 2009/0312532 A1 | 12/2009 | Van Deutekom et al. |
| 2010/0016215 A1 | 1/2010 | Moulton et al. |
| 2010/0130591 A1 | 5/2010 | Sazani et al. |
| 2010/0168212 A1 | 7/2010 | Popplewell et al. |
| 2011/0015253 A1 | 1/2011 | Wilton et al. |
| 2011/0015258 A1 | 1/2011 | Wilton et al. |
| 2011/0046203 A1 | 2/2011 | Wilton et al. |
| 2011/0046360 A1 | 2/2011 | Matsuo et al. |
| 2011/0110960 A1 | 5/2011 | Platenburg |
| 2011/0263682 A1 | 10/2011 | De Kimpe et al. |
| 2011/0263686 A1 | 10/2011 | Wilton et al. |
| 2011/0281787 A1 | 11/2011 | Lu et al. |
| 2011/0294753 A1 | 12/2011 | De Kimpe et al. |
| 2011/0312086 A1 | 12/2011 | Van Deutekom |
| 2012/0022134 A1 | 1/2012 | De Kimpe et al. |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0046342 A1 | 2/2012 | Van Deutekom et al. |
| 2012/0053228 A1 | 3/2012 | Iversen et al. |
| 2012/0059042 A1 | 3/2012 | Platenburg et al. |
| 2012/0065169 A1 | 3/2012 | Hanson et al. |
| 2012/0065244 A1 | 3/2012 | Popplewell et al. |
| 2012/0108652 A1 | 5/2012 | Popplewell et al. |
| 2012/0108653 A1 | 5/2012 | Popplewell et al. |
| 2012/0115150 A1 | 5/2012 | Bozzoni et al. |
| 2012/0122801 A1 | 5/2012 | Platenburg |
| 2012/0149756 A1 | 6/2012 | Schumperli et al. |
| 2012/0172415 A1 | 7/2012 | Voit et al. |
| 2012/0202752 A1 | 8/2012 | Lu |
| 2012/0289457 A1 | 11/2012 | Hanson |
| 2013/0072671 A1 | 3/2013 | Van Deutekom |
| 2013/0090465 A1 | 4/2013 | Matsuo et al. |
| 2013/0116310 A1 | 5/2013 | Wilton et al. |
| 2013/0190390 A1 | 7/2013 | Sazani et al. |
| 2013/0197220 A1 | 8/2013 | Ueda |
| 2013/0211062 A1 | 8/2013 | Watanabe et al. |
| 2013/0217755 A1 | 8/2013 | Wilton et al. |
| 2013/0253033 A1 | 9/2013 | Wilton et al. |
| 2013/0253180 A1 | 9/2013 | Wilton et al. |
| 2013/0274313 A1 | 10/2013 | Wilton et al. |
| 2013/0289096 A1 | 10/2013 | Popplewell et al. |
| 2013/0302806 A1 | 11/2013 | Van Deutekom |
| 2013/0331438 A1 | 12/2013 | Wilton et al. |
| 2014/0045916 A1 | 2/2014 | Iversen et al. |
| 2014/0057964 A1 | 2/2014 | Popplewell et al. |
| 2014/0080896 A1 | 3/2014 | Nelson et al. |
| 2014/0080898 A1 | 3/2014 | Wilton et al. |
| 2014/0094500 A1 | 4/2014 | Sazani et al. |
| 2014/0113955 A1 | 4/2014 | De Kimpe et al. |
| 2014/0128592 A1 | 5/2014 | De Kimpe et al. |
| 2014/0155587 A1 | 6/2014 | Wilton et al. |
| 2014/0213635 A1 | 7/2014 | Van Deutekom |
| 2014/0221458 A1 | 8/2014 | De Kimpe et al. |
| 2014/0243515 A1 | 8/2014 | Wilton et al. |
| 2014/0243516 A1 | 8/2014 | Wilton et al. |
| 2014/0275212 A1 | 9/2014 | van Deutekom |
| 2014/0296323 A1 | 10/2014 | Leumann et al. |
| 2014/0315862 A1 | 10/2014 | Kaye |
| 2014/0315977 A1 | 10/2014 | Bestwick et al. |
| 2014/0316123 A1 | 10/2014 | Matsuo et al. |
| 2014/0323544 A1 | 10/2014 | Bestwick et al. |
| 2014/0329762 A1 | 11/2014 | Kaye |
| 2014/0329881 A1 | 11/2014 | Bestwick et al. |

(56) References Cited

U.S. PATENT DOCUMENTS

| | | |
|---|---|---|
| 2014/0343266 A1 | 11/2014 | Watanabe et al. |
| 2014/0350067 A1 | 11/2014 | Wilton et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2015/0045413 A1 | 2/2015 | De Visser et al. |
| 2015/0057330 A1 | 2/2015 | Wilton et al. |
| 2015/0152415 A1 | 6/2015 | Sazani et al. |
| 2015/0232839 A1 | 8/2015 | Iversen et al. |
| 2015/0353931 A1 | 12/2015 | Wilton et al. |
| 2015/0361428 A1 | 12/2015 | Bestwick et al. |
| 2015/0376615 A1 | 12/2015 | Wilton et al. |
| 2015/0376616 A1 | 12/2015 | Wilton et al. |
| 2015/0376617 A1 | 12/2015 | Sazani et al. |
| 2015/0376618 A1 | 12/2015 | Sazani et al. |
| 2016/0002631 A1 | 1/2016 | Wilton et al. |
| 2016/0002632 A1 | 1/2016 | Wilton et al. |
| 2016/0002633 A1 | 1/2016 | Sazani et al. |
| 2016/0002634 A1 | 1/2016 | Sazani et al. |
| 2016/0002635 A1 | 1/2016 | Wilton et al. |
| 2016/0002637 A1 | 1/2016 | Sazani et al. |
| 2016/0040162 A1 | 2/2016 | Bestwick et al. |
| 2016/0177301 A1 | 6/2016 | Wilton et al. |
| 2016/0298111 A1 | 10/2016 | Bestwick et al. |
| 2017/0009233 A1 | 1/2017 | Wilton et al. |
| 2017/0009234 A1 | 1/2017 | Wilton et al. |
| 2017/0283799 A1 | 10/2017 | Kaye |
| 2017/0292125 A1 | 10/2017 | Sazani et al. |

FOREIGN PATENT DOCUMENTS

| | | |
|---|---|---|
| CA | 2507125 A1 | 6/2004 |
| EP | 1054058 A1 | 11/2000 |
| EP | 1160318 A2 | 12/2001 |
| EP | 1160318 B1 | 12/2001 |
| EP | 1191097 A1 | 3/2002 |
| EP | 1191098 A2 | 3/2002 |
| EP | 1191098 B9 | 3/2002 |
| EP | 1495769 A1 | 1/2005 |
| EP | 1495769 B1 | 1/2005 |
| EP | 1544297 A2 | 6/2005 |
| EP | 1544297 B1 | 6/2005 |
| EP | 1568769 A1 | 8/2005 |
| EP | 1606407 B1 | 1/2006 |
| EP | 1619249 A1 | 1/2006 |
| EP | 1619249 B1 | 1/2006 |
| EP | 1857548 A1 | 11/2007 |
| EP | 2119783 A1 | 11/2009 |
| EP | 2135948 A2 | 12/2009 |
| EP | 2206781 A2 | 7/2010 |
| EP | 2258863 A1 | 12/2010 |
| EP | 1766010 B1 | 2/2011 |
| EP | 2284264 A1 | 2/2011 |
| EP | 2374885 A2 | 10/2011 |
| EP | 2386636 A2 | 11/2011 |
| EP | 2392660 A2 | 12/2011 |
| EP | 2500430 A2 | 9/2012 |
| EP | 2530153 A1 | 12/2012 |
| EP | 2530154 A1 | 12/2012 |
| EP | 2530155 A1 | 12/2012 |
| EP | 2530156 A1 | 12/2012 |
| EP | 2581448 A1 | 4/2013 |
| EP | 2594640 A1 | 5/2013 |
| EP | 2594641 A1 | 5/2013 |
| EP | 2594642 A1 | 5/2013 |
| EP | 2602322 A1 | 6/2013 |
| EP | 2607484 A1 | 6/2013 |
| EP | 2612917 A1 | 7/2013 |
| EP | 2614827 A2 | 7/2013 |
| EP | 2623507 A1 | 8/2013 |
| EP | 2636740 A1 | 9/2013 |
| EP | 2636741 A1 | 9/2013 |
| EP | 2636742 A1 | 9/2013 |
| EP | 2435582 B1 | 10/2013 |
| EP | 2435583 B1 | 7/2014 |
| EP | 2488165 B1 | 7/2014 |
| EP | 2135948 B1 | 9/2014 |
| EP | 2799548 A1 | 11/2014 |
| EP | 2801618 A1 | 11/2014 |
| JP | 2000-325085 A | 11/2000 |
| JP | 2002-010790 A | 1/2002 |
| JP | 2002-529499 A | 9/2002 |
| JP | 2002-325582 A | 11/2002 |
| JP | 2002-390857 A | 11/2002 |
| JP | 2004-509622 A | 4/2004 |
| JP | 2008-507577 A | 3/2008 |
| JP | 2010-268815 A | 12/2010 |
| JP | 2011-101655 A | 5/2011 |
| JP | 4777777 B2 | 9/2011 |
| JP | 2011-200235 A | 10/2011 |
| JP | 4846965 B2 | 12/2011 |
| JP | 5138722 B2 | 2/2013 |
| JP | 5378423 B2 | 12/2013 |
| JP | 2014-054250 A | 3/2014 |
| JP | 2014-111638 A | 6/2014 |
| JP | 2014-138589 A | 7/2014 |
| WO | 93/20227 A1 | 10/1993 |
| WO | 94/02595 A1 | 2/1994 |
| WO | 94/26887 A1 | 11/1994 |
| WO | 96/10391 A1 | 4/1996 |
| WO | 96/10392 A1 | 4/1996 |
| WO | 97/30067 A1 | 8/1997 |
| WO | 97/34638 A1 | 9/1997 |
| WO | 00/15780 A1 | 3/2000 |
| WO | 00/44897 A1 | 8/2000 |
| WO | 0078341 A1 | 12/2000 |
| WO | 01/49775 A2 | 7/2001 |
| WO | 01/72765 A1 | 10/2001 |
| WO | 01/83503 A2 | 11/2001 |
| WO | 01/83740 A2 | 11/2001 |
| WO | 02/018656 A2 | 3/2002 |
| WO | 02/024906 A1 | 3/2002 |
| WO | 0229406 A1 | 4/2002 |
| WO | 03/053341 A2 | 7/2003 |
| WO | 04/048570 A1 | 6/2004 |
| WO | 04/083446 A2 | 9/2004 |
| WO | 2004083432 A1 | 9/2004 |
| WO | 2005/115479 A2 | 12/2005 |
| WO | 2006/000057 A1 | 1/2006 |
| WO | 2006/021724 A2 | 3/2006 |
| WO | 2006/112705 A2 | 10/2006 |
| WO | 2007/058894 A2 | 5/2007 |
| WO | 2007/133812 A2 | 11/2007 |
| WO | 2007/135105 A1 | 11/2007 |
| WO | 2008/036127 A2 | 3/2008 |
| WO | 2009/054725 A2 | 4/2009 |
| WO | 2009/101399 A1 | 8/2009 |
| WO | 2009/139630 A2 | 11/2009 |
| WO | 2010/048586 A1 | 4/2010 |
| WO | 2010/050801 A1 | 5/2010 |
| WO | 2010/050802 A2 | 5/2010 |
| WO | 2010/115993 A1 | 10/2010 |
| WO | 2010/123369 A1 | 10/2010 |
| WO | 2010/136415 A1 | 12/2010 |
| WO | 2010/136417 A1 | 12/2010 |
| WO | 2010/150231 A1 | 12/2010 |
| WO | 2011/024077 A2 | 3/2011 |
| WO | 2011/045747 A1 | 4/2011 |
| WO | 2011/057350 A1 | 5/2011 |
| WO | 2011/143008 A1 | 11/2011 |
| WO | 2012/001941 A1 | 1/2012 |
| WO | 2012/029986 A1 | 3/2012 |
| WO | 2012/043730 A1 | 4/2012 |
| WO | 2012/109296 A1 | 8/2012 |
| WO | 2012/150960 A1 | 11/2012 |
| WO | 2013/033407 A2 | 3/2013 |
| WO | 2013/053928 A1 | 4/2013 |
| WO | 2013/00190 A1 | 7/2013 |
| WO | 2013/112053 A1 | 8/2013 |
| WO | 2013/142087 A1 | 9/2013 |
| WO | 2014/007620 A2 | 1/2014 |
| WO | 2014/100714 A1 | 6/2014 |
| WO | 2014/153220 A2 | 9/2014 |
| WO | 2014/153240 A2 | 9/2014 |

(56) References Cited

FOREIGN PATENT DOCUMENTS

| WO | 2014/172669 A1 | 10/2014 |
|---|---|---|
| WO | 2014/144978 A2 | 11/2014 |
| WO | 2017/059131 A1 | 4/2017 |

OTHER PUBLICATIONS

*University of Western Australia* v. *Academisch Ziekenhuis Leiden*, University of Western Australia Exhibit List As of Oct. 29, 2015, filed in Patent Interference No. 106,013, Oct. 29, 2015, pp. 1-10 (Doc 199).

*University of Western Australia* v. *Academisch Ziekenhuis Leiden*, University of Western Australia Request for Rehearing, filed in Patent Interference No. 106,013, Oct. 29, 2015, pp. 1-20 (Doc 198).

*Vikase Corp.* v. *Am. Nat'l. Can Co.*, No. 93-7651, 1996 WL 377054 (N.D. Ill. Jul. 1, 1996), 3 pages (Exhibit No. 2152 filed in interference 106013 on Oct. 29, 2015).

International Preliminary Report on Patentability, PCT/US2014/029669, dated Sep. 15, 2015, pp. 1-10.

International Preliminary Report on Patentability, PCT/US2014/029766, dated Sep. 15, 2015, pp. 1-10.

*University of Western Australia* v. *Academisch Ziekenhuis Leiden*, Decision—Priority 37 CFR § 41.125 (a), 18 pages, Patent Interference No. 106,013, (Doc 196), dated Sep. 29. 2015.

*University of Western Australia* v. *Academisch Ziekenhuis Leiden*, Judgment—37 CFR § 41.127, 2 pages, Patent Interference No. 106,013, (Doc 197), dated Sep. 29, 2015.

*University of Western Australia* v. *Academisch Ziekenhuis Leiden*, Statement Concerning Subsequent Settlement Discussions, filed in Patent Interference No. 106,013, Aug. 24, 2015, pp. 1-3 (Doc 195).

*University of Western Australia* v. *Academisch Ziekenhuis Leiden*, UWA Notice of Recent Authority, filed in Patent Interference No. 106,007, Sep. 2, 2015, pp. 1-18 (Doc 470).

*University of Western Australia* v. *Academisch Ziekenhuis Leiden*, UWA Notice of Recent Authority, filed in Patent Interference No. 106,008, Sep. 2, 2015, pp. 1-18 (Doc 478).

U.S. Pat. No. 8,759,307 (Stein et al.), pp. 35, Exhibit No. 1101 filed in interferences 106,007 and 106,008 on Feb. 13, 2015.

U.S. Pat. No. 8,779,128 (Hanson et al.), pp. 104, Exhibit No. 1102 filed in interferences 106,007 and 106,008 on Feb. 13, 2015.

U.S. Pat. No. 8,785,407 (Stein et al.), pp. 35, Exhibit No. 1103 filed in interferences 106,007 and 106,008 on Feb. 13, 2015.

U.S. Pat. No. 8,785,410 (Iversen et al.), pp. 20, Exhibit No. 1104 filed in interferences 106,007 and 106,008 on Feb. 13, 2015.

U.S. Pat. No. 8,835,402 (Kole et al.), pp. 27, Exhibit No. 1105 filed in interferences 106,007 and 106,008 on Feb. 13, 2015.

U.S. Pat. No. 8,865,883 (Sazani et al.), pp. 199, Exhibit No. 1106 filed in interferences 106,007 and 106,008 on Feb. 13, 2015.

U.S. Pat. No. 8,871,918 (Sazani et al.), pp. 195, Exhibit No. 1107 filed in interferences 106,007 and 106,008 on Feb. 13, 2015.

U.S. Pat. No. 8,877,725 (Iversen et al.), pp. 34, Exhibit No. 1108 filed in interferences 106,007 and 106,008 on Feb. 13, 2015.

U.S. Pat. No. 8,895,722 (Iversen at al.), pp. 29, Exhibit No. 1109 filed in interferences 106,007 and 106,008 on Feb. 13, 2015.

U.S. Pat. No. 8,906,872 (Iversen et al.), pp. 69, Exhibit No. 1110 filed in interferences 106,007 and 106,008 on Feb. 13, 2015.

US Abandonment for U.S. Appl. No. 13/902,376, 1 page, dated Jun. 12, 2014 (Exhibit No. 1047 filed in interferences 106008, 106007 on Nov. 18, 2014).

U.S. Amendment After Non-Final Action for U.S. Appl. No. 11/233,495, 31 pages, dated Jun. 24, 2010 (Exhibit No. 2073 filed in interferences 106008, 106013, 106007 on Nov. 18, 2014).

U.S. Amendment for U.S. Appl. No. 11/233,495, 15 pages, dated Apr. 1, 2009 (Exhibit No. 2071 filed in interferences 106008, 106013, 106007 on Nov. 18, 2014).

U.S. Amendment for U.S. Appl. No. 11/233,495, 19 pages, dated Sep. 16, 2009 (Exhibit No. 2072 filed in interferences 106008, 106013, 106007 on Nov. 18, 2014).

U.S. Amendment for U.S. Appl. No. 11/233,495, 9 pages, dated Oct. 31, 2007 (Exhibit No. 2070 filed in interferences 106008, 106013, 106007 on Nov. 18, 2014).

U.S. Amendment for U.S. Appl. No. 11/570,691, 9 pages, dated Jun. 15, 2010 (Exhibit No. 1043 filed in interferences 106008, 106007 on Nov. 18, 2014).

U.S. Amendment for U.S. Appl. No. 13/271,080, 30 pages, dated Jan. 30, 2013 (Exhibit No. 1049 filed in interferences 106008, 106007 on Nov. 18, 2014).

U.S. Amendment for U.S. Appl. No. 13/902,376, 36 pages, dated Mar. 21, 2014 (Exhibit No. 1046 filed in interferences 106008, 106007 on Nov. 18, 2014).

U.S. Amendment in Response to Advisory Action for U.S. Appl. No. 11/233,495, 23 pages, dated Mar. 14, 2011 (Exhibit No. 2074 filed in interferences 106008, 106013, 106007 on Nov. 18, 2014).

U.S. Amendments to the Claims for U.S. Appl. No. 11/233,495, 4 pages, dated May 8, 2014 (Exhibit No. 2077 filed in interferences 106008, 106013, 106007 on Nov. 18, 2014).

U.S. Amendments to the Claims for U.S. Appl. No. 14/198,992, 3 pages, dated Jul. 16, 2014 (Exhibit No. 2079 filed in interferences 106008, 106013, 106007 on Nov. 18, 2014).

U.S. Applicant-Initiated Interview Summary and Notice of Allowance for U.S. Appl. No. 13/550,210, 9 pages dated May 19, 2014 (Exhibit No. 2076 filed in interferences 106008, 106013, 106007 on Nov. 18, 2014).

US application as-filed and Preliminary Amendment for U.S. Appl. No. 13/550,210, 59 pages dated Jul. 16, 2012 (Exhibit No. 2087 filed in interferences 106008, 106013, 106007 on Nov. 18, 2014).

US Application as-filed for U.S. Appl. No. 14/198,992, 52 pages, dated Mar. 6, 2014 (Exhibit No. 2086 filed in interferences 106008, 106013, 106007 on Nov. 18, 2014).

US Application as-filed, Application Data Sheet, and Preliminary Amendment for U.S. Appl. No. 12/837,359, 101 pages, dated Jul. 15, 2010 (Exhibit No. 2100 filed in interferences 106008, 106013, 106007 on Nov. 18, 2014).

US Application for Letters Patent for U.S. Appl. No. 11/233,495 as-filed and preliminary amendment, 77 pages, dated Sep. 21, 2005 (Exhibit No. 2095 filed in interferences 106008, 106013, 106007 on Nov. 18, 2014).

U.S. Appl. No. 11/233,495, 74 pages; excerpts of prosecution history including: U.S. Supplemental Amendment and Response dated May 8, 2014; Second Supplemental Response dated Jul. 25, 2013; Supplemental Amendment dated Jun. 26, 2013; Amendment after Non-final Action dated Nov. 1, 2010; Amendment under 35 USC 1.114 dated Sep. 16, 2009 (Exhibit No. 2054 filed in interferences 106008, 106013, 106007 on Nov. 18, 2014).

U.S. Appl. No. 14/198,992, 17 pages; excerpts of prosecution history including: Supplemental Amendment dated Jul. 16, 2014; Response to Non-Final Office Action dated Jul. 14, 2014 (Exhibit No. 2056 filed interferences 106008, 106013, 106007 on Nov. 18, 2014).

U.S. Appl. No. 14/248,279, 29 pages; excerpts of prosecution history including: Amendment under 37 CFR 1.312 dated Sep. 19, 2014; Amendment in Response to Final Office Action dated Aug. 7, 2014; Declaration under 37 CFR 1.132 dated May 26, 2014; Declaration under 37 CFR 1.132 dated May 27, 2014; Response dated Jun. 3, 2014 (Exhibit No. 2057 filed in interferences 106008, 106013, 106007 on Nov. 18, 2014).

U.S. Appl. No. 13/550,210, 27 pages; excerpts of prosecution history including: Response and Amendment dated May 12, 2014; Response to Non-Final Office Action dated Jan. 21, 2014; Second Preliminary Amendment dated Jan. 3, 2013 (Exhibit No. 2955 filed in interferences 106008, 106013, 106007 on Nov. 18, 2014).

U.S. claim amendments for U.S. Appl. No. 13/550,210, 3 pages, dated May 12, 2014 (Exhibit No. 2078 filed in interferences 106008, 106013, 106007 on Nov. 18, 2014).

Claims for U.S. Appl. No. 12/976,381, 1 page, dated Dec. 22, 2010 (Exhibit No. 2065 filed in interferences 106008, 106013, 106007 on Nov. 18, 2014).

U.S. Declaration of Richard K. Bestwick, for U.S. Appl. No. 11/570,691, 5 pages, Jun. 15, 2010 (Exhibit No. 1044 filed in interferences 106008, 106007 on Nov. 18, 2014).

(56) References Cited

OTHER PUBLICATIONS

US E-mail from Patent Trial and Appeal Board to Danny Huntington, 2 pages, dated Oct. 9, 2014 (Exhibit No. 2002 filed in interferences 106008 on Oct. 17, 2014).

U.S. Non-Final Office Action for U.S. Appl. No. 11/570,691, 16 pages, dated Mar. 15, 2010 (Exhibit No. 1042 filed in interferences 106008, 106007 on Nov. 18, 2014).

U.S. Office Action for U.S. Appl. No. 13/271,080, 25 pages, dated Jul. 30, 2012 (Exhibit No. 1048 filed in interferences 106008, 106007 on Nov. 18, 2014).

U.S. Office Action for U.S. Appl. No. 13/550,201, 12 pages, dated Sep. 27, 2013 (Exhibit No. 2080 filed in interferences 106008, 106013, 106007 on Nov. 18, 2014).

U.S. Office Action for U.S. Appl. No. 13/902,376, 7 pages, dated Jan. 7, 2014 (Exhibit No. 1045 filed in interferences 106008, 106007 on Nov. 18, 2014).

U.S. Appl. No. 12/198,007 as-filed, 64 pages, dated Aug. 25, 2008 (Exhibit No. 2092 filed in interferences 106008, 106013, and 106007 on Nov. 18, 2014).

U.S. Preliminary Amendment and application as-filed for U.S. Appl. No. 12/976,381,64 pages, dated Dec. 22, 2010 (Exhibit No. 2089 filed in Interferences 106007, 106008, and 106013 on Nov. 18, 2014).

U.S. Preliminary Amendment for U.S. Appl. No. 11/233,495, 10 pages, dated Sep. 21, 2005 (Exhibit No. 2069 filed in interferences 106008, 106013, 106007 on Nov. 18, 2014).

US Preliminary Remarks for U.S. Appl. No. 14/198,992, 1 page, dated Mar. 6, 2014 (Exhibit No. 2097 filed in interferences 106008, 106013, 106007 on Nov. 18, 2014).

US Proposed Terminal Disclaimer for U.S. Appl. No. 12/860,078, 2 pages, dated Oct. 17, 2014 (Exhibit No. 2001 filed in interference 106003 on Oct. 17, 2014).

US Remarks for U.S. Appl. No. 14/248,279, 2 pages, dated Aug. 27, 2014 (Exhibit No. 2110 filed in Interferences 106008, 106013, 106007 on Nov. 18, 2014).

U.S. Response and amendments for U.S. Appl. No. 13/550,210, 12 pages, dated Jan. 21, 2014 (Exhibit No. 2063 filed in interferences 106008, 106013, 106007 on Nov. 18, 2014).

US Revised Figure 4H, U.S. Appl. No. 13/271,080, 1 page (Exhibit No. 1050 filed in interferences 106008, 106007 on Nov. 18, 2014).

US Terminal Discaimer for U.S. Appl. No. 14/198,992, 1 page, dated Jul. 15, 2014 (Exhibit No. 2096 filed in interferences 106008, 106013, 106007 on Nov. 18, 2014).

US Terminal Disclaimer for U.S. Appl. No. 14/248,279, 1 page, dated Aug. 7, 2014 (Exhibit No. 2109 filed in interferences 106008, 106013, 106007 on Nov. 18, 2014).

US Track One Request, Application as-filed, and Application Data Sheet for U.S. Appl. No. 14/248,279, 68 pages, dated Apr. 8, 2014 (Exhibit No. 2108 filed in interferences 106008, 106013, 106007 on Nov. 18, 2014).

US Transmittal, application as-filed, and Preliminary Amendment for U.S. Appl. No. 11/570,691, 102 pages, dated Dec. 15, 2006 (Exhibit No. 2103 filed in interferences 106008, 106013, 106007 on Nov. 18, 2014).

AON PS229 (h53AON1) HPLC Method Report, pp. 3, Exhibit No. 1139 filed in Interferences 106,007 and 106,008 on Feb. 16, 2015.

AON PS229 (h53AON1) Mass Spectrometry Data, pp. 3, Exhibit No. 1142 filed in Interferences 106,007 and 106,008 on Feb. 16, 2015.

AON PS229 (h53AON1) Synthesis Laboratory Notebook Entry, pp. 1, Exhibit No. 1137 filed in Interferences 106,007 and 106,008 on Feb. 16, 2015.

AON PS229L (h53AON229L) Certificate of Analysis, pp. 1, Exhibit No. 1129 filed in Interferences 106,007 and 106,008 on Feb. 17, 2015.

AON PS43 (h51AON1) Certificate of Analysis, pp. 1, Exhibit No. 1134 filed in Interferences 106,007 and 106,008 on Feb. 16, 2015.

AON PS43 (h51AON1) HPLC Chromatogram, pp. 1, Exhibit No. 1131 filed in Interferences 106,007 and 106,008 on Feb. 17, 2015.

AON PS43 (h51AON1) HPLC Method Report, pp. 4, Exhibit No. 1130 filed in Interferences 106,007 and 106,008 on Feb. 17, 2015.

AON PS43 (h51AON1) Mass Spectrometry Data, pp. 3, Exhibit No. 1135 filed in Interferences 106,007 and 106,008 on Feb. 16, 2015.

AON PS43 (h51AON1) UPLC-UV Data, pp. 2, Exhibit No. 1136 filed in Interferences 106,007 and 106,008 on Feb. 16, 2015.

AONs PS1958, PS1959, PS1960, PS1961, PS1962, PS1963, PS1964, PS1965, PS1966, and PS1967 HPLC Method Report, pp. 3, Exhibit No. 1143 filed in Interferences 106,007 and 106,008 on Feb. 16, 2015.

Applicant-Initiated Interview Summary dated Apr. 8, 2013 in U.S. Appl. No. 13/094,548, (University of Western Australia Exhibit 2144, filed Apr. 3, 2015 in Interferences 106007, 106008, and 106013, pp. 1-11).

Arechavala-Gomeza V, et al., "Immunohistological intensity measurements as a tool to assess sarcolemma-associated protein expression," Neuropathol Appl Neurobiol 2010;36: 265-74.

Arechavala-Gomeza, V, et al., "Comparative Analysis of Antisense Oligonucleotide Sequences for Targeted Skipping of Exon 51 During Dystrophin Pre-mRNA Splicing in Human Muscle," Human Gene Therapy, vol. 18:790-810 (2007).

Arora, Vikram et al., "c-Myc Antisense Limits Rat Liver Regeneration and Indicates Role for c-Myc in Regulating Cytochrome P-450 3A Activity," The Journal of Pharmacology and Experimental Therapeutics, vol. 292(3):921-928 (2000).

*Asetek Danmark A/S v. CMI USA, Inc.*, 2014 WL 5990699, N.D. Cal. 2014, 8 pages, (Academisch Ziekenhuis Leiden Exhibit 1237, filed May 5, 2015 in Interference 106007 and 106008).

Asvadi, Parisa et al., "Expression and functional analysis of recombinant scFv and diabody fragments with specificity for human RhD," Journal of Molecular Recognition, vol. 15:321-330 (2002).

Australian Application No. 2004903474, 36 pages, dated Jul. 22, 2005 (Exhibit No. 1004 filed in interferences 106008, 106007 on Nov. 18, 2014).

AVI BioPharma, Inc., "Exon 51 Sequence of Dystrophin," Document D19 as filed in Opposition of European Patent EP1619249, filed Jun. 23, 2009, 7 pages.

AZL's PCT/NL03/00214 (the as-filed AZL PCT Application) Exhibit No. 1006, filed in Interference No. 106,007, 64 pages, Dec. 23, 2014.

AZL's U.S. Appl. No. 14/295,311 and claims, as-filed Jun. 3, 2014 ("The '311 Application") (Exhibit No. 1077 filed in interferences 106008, 106007 on Dec. 23, 2014).

Azofeifa J, et al., "X-chromosome methylation in manifesting and healthy carriers of dystrophinopathies: concordance of activation ratios among first degree female relatives and skewed inactivation as cause of the affected phenotypes," Hum Genet 1995;96:167-176.

Beaucage, S.L. et al., "Deoxynucleoside Phosphoramidites—A New Class of Key Intermediates for Deoxypolynucleotide Synthesis," Tetrahedron Letters, vol. 22(20):1859-1862 (1981).

Bellare, Priya et al., "A role for ubiquitin in the spliceosome assembly pathway," Nature Sturctural & Molecular Biology, vol. 15(5):444-451 (2008) (Exhibit No. 1057 filed in interferences 106008, 106007 on Nov. 18, 2014).

Bellare, Priya et al., "Ubiquitin binding by a variant Jab1/MPN domain in the essential pre-mRNA splicing factor Prp8p," RNA, vol. 12:292-302 (2006) (Exhibit No. 1056 filed in interferences 106008, 106007 on Nov. 18, 2014).

Bennett, C. Frank et al., "RNA Targeting Therapeutics: Molecular Mechanisms of Antisense Oligonucleotides as a Therapeutic Platform," Annu. Rev. Pharmacol. Toxicol., vol. 50:259-293 (2010) (Exhibit No. 1025 filed in interferences 106008, 106007 on Nov. 18, 2014).

Berge, Stephen M. et al., "Pharmaceutical Salts," Journal of Pharmaceutical Sciences, vol. 66(1):1-18 (1977).

Bestas et al., "Design and Application of Bispecific Splice Switching Oligonucleotides," Nuc. Acid Therap., vol. 24, No. 1, pp. 13-24 (2014), Exhibit No. 1120 filed in interferences 106,007 and 106,008 on Feb. 17, 2015.

Braasch, Dwaine A. et al., "Locked nucleic acid (LNA): fine-tuning the recognition of DNA and RNA," Chemistry & Biology, vol. 8:1-7 (2001) (Exhibit No. 2009 filed in interferences 106008, 106013, 106007 on Nov. 18, 2014).

(56) References Cited

OTHER PUBLICATIONS

Braasch, Dwaine A. et al., "Novel Antisense and Peptide Nucleic Acid Strategies for Controlling Gene Expression," Biochemistry, vol. 41(14):4503-4510 (2002) (Exhibit No. 2006 filed in interferences 106008, 106013, 106007 on Nov. 18, 2014).

Bremmer-Bout, Mattie et al., "Targeted Exon Skipping in Transgenic hDMD Mice: A Model for Direct Preclinical Screening of Human-Specific Antisense Oligonucleotides," Molecular Therapy, vol. 10(2):232-240 (2004) (Exhibit No. 2024 filed in interferences 106008, 106013, 106007 on Nov. 18, 2014).

Brooke MH, et al., "Clinical investigation in Duchenne dystrophy: 2. Determination of the "power" of therapeutic trials based on the natural history," Muscle Nerve. 1983;6:91-103.

Brown, Susan C. et al., "Dystrophic phenotype induced in vitro by antibody blockade of muscle alpha-dystroglycan-laminin interaction," Journal of Cell Science, vol. 112:209-216 (1999).

Bushby K., et al. "Diagnosis and management of Duchenne muscular dystrophy, part 1: diagnosis, and pharmacological and psychosocial management," Lancet Neurol 2010;9:77-93.

Bushby KM, et al., "The clinical, genetic and dystrophin characteristics of Becker muscular dystrophy," II. Correlation of phenotype with genetic and protein abnormalities. J Neurol 1993;240: 105-112.

Bushby KM, et al., "The clinical, genetic and dystrophin characteristics of Becker muscular dystrophy," I. Natural history. J Neurol 1993;240:98-104.

Canonico, A.E. et al., "Expression of a CMV Promoter Drive Human alpha-1 Antitrypsin Gene in Cultured Lung Endothelial Cells and in the Lungs of Rabbits," Clinical Research, vol. 39(2):219A (1991).

Cirak, Sebahattin et al., "Exon skipping and dystrophin restoration in patients with Duchenne muscular dystrophy after systemic phosphorodiamidate morpholino oligomer treatment: an open-label, phase 2, dose-escalation study," Lancet, vol. 378(9791):595-605 (2011).

Claim Chart U.S. Appl. No. 11/233,195, pp. 57, Exhibit No. 1216 filed in Interferences 106,007 and 106,008 on Feb. 17, 2015.

Claim Chart U.S. Appl. No. 13/550,210, pp. 45, Exhibit No. 1217 filed in Interferences 106,007 and 106,008 on Feb. 17, 2015.

Claim Chart, U.S. Pat. No. 7,807,816, 14 pages (Exhibit No. 1063 filed in interferences 106008, 106007 on Nov. 18, 2014).

Claim Chart, U.S. Pat. No. 7,960,541, 17 pages (Exhibit No. 1064 filed in interferences 106008, 106007 on Nov. 18, 2014).

Claim Chart, U.S. Pat. No. 8,455,636, 32 pages (Exhibit No. 1062 filed in interferences 106008, 106007 on Nov. 18, 2014).

Claim Comparison Chart—Claims 11 and 29 in U.S. Appl. No. 13/550,210, pp. 1, Exhibit No. 1226 filed in Interferences 106,007 and 106,008 on Feb. 17, 2015.

Claim Comparison Chart U.S. Appl. No. 13/550,210 vs U.S. Appl. No. 11/233,495, pp. 12, Exhibit No. 1218 filed in Interferences 106,007 and 106,008 on Feb. 17, 2015.

Claim Comparison Chart U.S. Appl. No. 13/550,210 vs U.S. Appl. No. 12/198,007, pp. 1, Exhibit No. 1219 filed in Interferences 106,107 and 106,008 on Feb. 17, 2015.

Claims from U.S. Appl. No. 11/233,495, 6 pages, dated Sep. 21, 2005 (Exhibit No. 2068 filed in interferences 106008, 106013, 106007 on Nov. 18, 2014).

Classification Excerpts from USPC, System, 21 pages, (Academisch Ziekenhuis Leiden Exhibit 1234, filed May 5, 2015 In Interference 106007 and 106008).

Collins, C.A. et al., "Duchenne's muscular dystrophy: animal models used to investigate pathogenesis and develop therapeutic strategies," Int. J. Exp. Pathol., vol. 84(4):165-172 (2003).

Confirmation of Dystrophin Exon 48 to 50 Deletion in Cell Line 8036 Laboratory Notebook Entry, pp. 3, Exhibit No. 1167 filed in Interferences 106,007 and 106,008 on Feb. 16, 2015.

Confirmation of Dystrophin Exon 52 Deletion in Cell Line R1809 Laboratory; Notebook Entry, pp. 3, Exhibit No. 1168 filed in Interferences 106,007 and 106,008 on Feb. 16, 2015.

Confirmatory Study of Eteplirsen in DMD Patients, An Open-Label, Multi-Center, 48-Week Study With a Concurrent Untreated Control Arm to Evaluate the Efficacy and Safety of Eteplirsen in Duchenne Muscular Dystrophy ,Clinical Trials.gov, Clinical Trial Identifier NCT02255552, Oct. 1, 2014, 3 pages.

Confirmatory Study of Eteplirsen in DMD Patients, An Open-Label, Multi-Center, 48-Week Study With a Concurrent Untreated Control Arm to Evaluate the Efficacy and Safety of Eteplirsen in Duchenne Muscular Dystrophy, Clinical Trials.gov, Clinical Trial Identifier NCT02255552, May 26, 2015, 3 pages.

*Coolidge* v. *Efendic*, 2008 WI. 2080735, Int. No. 105,457 (BPAI May 16, 2008), 42 pages, (Academisch Ziekenhuis Leiden Exhibit 1235, filed May 5, 2015 in Interference 106007 and 106008).

Corey, David R. et al., Morpholino antisense oligonucleotides: tools for investigating vertebrate development, Genome Biology, vol. 2(5):1015.1-1015.3 (2001) (Exhibit No. 1026 filed in interferences 106008, 106007 on Nov. 18, 2014).

Corrected Priority Statement filed by UWA in Int. No. 106,008 (as PN 219),pp. 5, Exhibit No. 1002 filed in Interference 106,013 on Feb. 17, 2015.

Cortes, Jesus J., et al., "Mutations in the conserved loop of human U5 snRNA generate use of novel cryptic 5' splice sites in vivo," EMBO J., vol. 12, No. 13, pp. 5181-5189 (1993), Exhibt No. 1187 filed in Interferences 106,007 and 106,008 on Feb. 17, 2015.

Crooke, Stanley T., Antisense Drug Technology, Principles, Strategies, and Applications, Marcel Dekker, Inc., New York, Chapters 15 and 16, pp. 375-389, 391-469 (2001) (Exhibit No. 2075 filed in interferences 106008, 106013, 106007 on Nov. 18, 2014).

Curriculum Vitae of Judith van Deutekom, pp. 6, Exhibit No. 1126 filed in interferences 106,007 and 106,008 on Feb. 17, 2015.

Curriculum Vitae, Erik Joseph Sontheimer, 18 pages, dated Sep. 29, 2014 (Exhibit No. 1013 filed in interferences 106008, 106007 on Nov. 18, 2014).

CV, Professor Matthew J.A. Wood, 3 pages (Exhibit No. 2003 filed in interferences 106008, 106007 on Nov. 18, 2014).

Davis, Richard J. et al., "Fusion of PAX7 to FKHR by the Variant t(1;13)(p36;q14) Translocation in Alveolar Rhabdomyosarcoma," Cancer Research, vol. 54:2869-2872 (1994) (Exhibit No. 1027 filed in interferences 106008, 106007 on Nov. 18, 2014).

De Angelis, Fernanda Gabriella el al., "Chimeric snRNA molecules carrying antisense sequences against the splice junctions of exon 51 of the dystrophic pre-mRNA induce exon skipping and restoration of a dystrophin synthesis in 48-50 DMD cells," PNAS, vol. 99(14):9456-9461 (2002).

Decision on Appeal, Ex Parte Martin Gleave and Hideaki Miyake, Appeal No. 2005-2447, U.S. Appl. No. 09/619,908 (Jan. 31, 2006) (2009 WL 6927761 (Bd.Pat.App.& Interf.), pp. 12, Exhibit No. 1207 filed in Interferences 106,007 and 106,008 on Feb. 17, 2015.

Decision on Request for ReHearing, Ex Parte Roderick John Scott, Appeal No. 2008-004077, U.S. Appl. No. 10/058,825 (Jan. 6, 2010) (2010 WL 191079 (Bd.Pat.App. & Interf.),pp. 21, Exhibit No. 1208 filed in Interferences 106,007 and 106,008 on Feb. 17, 2015.

Declaration of Judith C.T. van Deutekorn Under 37 C.F.R. §1.132, filed on Jan. 27, 2012, in U.S. Patent Reexamination Control No. 90/011,320, regarding U.S. Pat. No. 7,534,879, (University of Western Australia Exhibit 2133, filed Apr. 3, 2015 in Interferences 106007, 106003, and 106013, pp. 1-10).

Declaration of Judith van Deutekom, pp. 45, Exhibit No. 1125 filed in interferences 106,007 and 106,008 on Feb. 17, 2015.

Dellorusso, Christiana et al., "Functional correction of adult mdx mouse muscle using gutted adenoviral vectors expressing full-length dystrophin," PNAS, vol. 99(20):12979-12984 (2002).

Deposition Transcript of Erik J. Sontheimer, Ph.D. of Jan. 21, 2015 (99 pages), Exhibit No. 1215 filed in Interferences 106,007 and 106,008 on Feb. 17, 2015.

Deposition Transcript of Matthew J. A. Wood, M.D. , D. Phil., Jan. 22, 2015, including Errata Sheet, pp. 198, Exhibit No. 1007 filed in Interference 106,013 on Feb. 17, 2015.

Deposition Transcript of Matthew J.A. Wood, M D., D. Phil., pp. 196, Exhibit No. 1122 filed in interferences 106,007 and 106,008 on Feb. 17, 2015.

Desalting of Oligonucleotides, pp. 2, Exhibit No. 1132 filed in Interferences 106,007 arid 106,008 on Feb. 17, 2015.

(56) References Cited

OTHER PUBLICATIONS

Dirksen, Wessel P. et al., "Mapping the SF2/ASF Binding Sites in the Bovine Growth Hormone Exonic Splicing Enhancer," The Journal of Biological Chemistry, vol. 275(37):29170-29177 (2000).
Dominski, Zbigniew et al., "Identificaton and Characterization by Antisense Oligonucleotides of Exon and Intron Sequences Required for Splicing," Molecular and Cellular Biology, vol. 14(11):7445-7454 (1994).
Dominski, Zbigniew et al., "Restoration of correct splicing in thalassemic pre-mRNA by antisense oligonucleotides," Proc. Natl. Acad. Sci. USA, vol. 90:8673-8677 (1993).
Doran, Philip et al., "Proteomic profiling of antisense-induced exon skipping reveals reversal of pathobiochemical abnormalities in dystrophic mdx diaphragm," Proteomics, vol. 9:671-685, DOI 10.1002/pmic.200800441 (2009).
Douglas, Andrew G.L. et al., "Splicing therapy for neuromuscular disease," Molecular and Cellular Neuroscience, vol. 56:169-185 (2013) (Exhibit No. 2005 filed in interferences 106008, 106013, 106007 on Nov. 18, 2014).
Doyle, Donald F., et al. (2001) "Inhibition of Gene Expression Inside Cells by PeptideNucleic Acids: Effect of mRNA Target Sequence, Mismatched Bases, and PNA Length," Biochemistry 40:53-64, (Exhibit No. 2123 filed in interferences 106,007 and 106,008 on Feb. 17, 2015.
Dr. Wood Errata Sheet—Jan. 22, 2015, pp. 2, Exhibit No. 1227 filed in Interferences 106,007 and 106,008 on Feb. 17, 2015.
Dunckley, Matthew C. et al., "Modification of splicing in the dystrophin gene in cultured Mdx muscle cells by antisense oligoribonucleotides," Human Molecular Genetics, vol. 5(1):1083-1090 (1995).
Dunckley, Matthew G. et al., "Modulation of Splicing in the DMD Gene by Antisense Oligoribonucleotides," Nucleosides & Nucleotides, vol. 16(7-9):1665-1668 (1997).
Eckstein, F., "Nucleoside Phosphorothioates," Ann. Rev. Biochem., vol. 54:367-402 (1985) (Exhibit No. 1028 filed in interferences 106008, 106007 on Nov. 18, 2014).
Elayadi, Anissa N. et al., "Application of PNA and LNA oligomers to chemotherapy," Current Opinion in Investigational Drugs, vol. 2(4):558-561 (2001).
Email from Danny Huntington to Interference Trial Section, dated Sep. 21, 2014, pp. 2, Exhibit No. 3001 filed in Interference 106,007, 106,008, and 106,013 on Sep. 26, 2014.
Email From Sharon Crane to Interference Trial Section, dated Nov. 13, 2014, pp. 2, Exhibit No. 3002 filed in Interference 106,007, 106,008, and 106,013 on dated Nov. 14, 2014.
Emery, A.E. H., "Population frequencies of inherited neuromuscular diseases—a world survey," Neuromuscul Disord 1991;1:19-29.
Errata sheet for the Jan. 22, 2015 deposition of Matthew J. A. Wood, M.D., D. Phil., 2 pages, (Exhibit No. 2128 filed in interferences 106,007 and 106,008 on Feb. 17, 2015.
Errata sheet for the Mar. 12, 2015 deposition of Erik J. Sontheimer, PhD., (University of Western Australia Exhibit 2149, filed Apr. 3, 2015 in Interferences 106007, 106008, and 106013, p. 1).
Errington, Stephen J. et al., "Target selection for antisense oligonucleotide induced exon skipping in the dystrophin gene," The Journal of Gene Medicine, vol. 5:518-527 (2003).
European Office Acton for Application No. 09752572.9, 5 pages, dated Feb. 29, 2012.
European Response, Application No. 10004274.6, 7 pages, dated Nov. 5, 2013 (Exhibit No. 1060 filed in Interferences 106008, 106007 on Nov. 18, 2014).
European Response, Application No. 12198517.0, 7 pages, dated Oct. 21, 2014 (Exhibit No. 2084 filed in interferences 106008, 106013, 106007 on Nov. 18, 2014).
European Response, Application No. 13160338.3, 4 pages, dated Jun. 26, 2014 (Exhibit No. 2085 filed in interferences 106008, 106013, 106007 on Nov. 18, 2014).
European Search Report for Application No. 10004274.6, 12 pages, dated Jan. 2, 2013.

European Search Report for Application No. 12162995.0, 11 pages, dated Jan. 15, 2013.
European Search Report, EP15168694.6, dated Jul. 23, 2015, pp. 1-8.
Excerpts from Prosecution History of U.S. Appl. No. 13/741,150: Notice of Allowance dated Mar. 16, 2015; List of References cited by Applicant and Considered by Examiner; Notice of Allowance and Fees due dated Sep. 18, 2014; Amendment in Response to Non-Final Office Action dated Jul. 11, 2014, (Academisch Ziekenhuis Leiden Exhibit 1229, filed Apr. 3, 2015 in Interference 106007 and 106008, pp. 1-133).
Excerpts from Prosecution History of U.S. Appl. No. 13/826,880: Notice of Allowance dated Jan. 26, 2015 and Amendment in Response to Non-Final Office Action dated Oct. 15, 2014, (Academisch Ziekenhuis Leiden Exhibit 1228, filed Apr. 3, 2015 in Interference 106007 and 106008, pp. 1-16).
Excerpts from Yeo (Ed.), "Systems Biology of RNA Binding Proteins," Adv. Exp. Med. Biol., Chapter 9, 56 pages (2014), (Academisch Ziekenhuis Leiden Exhibit 1232, filed Apr. 3, 2015 in Interference 106007 and 106008, pp. 1-56).
Excerpts of SEC Form 8-K, dated Nov. 23, 2014, for BioMarin Pharmaceutical Inc., (University of Western Australia Exhibit 2129, filed Apr. 3, 2015 in Interferences 106007, 106008, and 106013, pp. 1-9).
Exon 51 Internal Sequence Schematic, pp. 1, Exhibit No. 1224 filed in Interferences 106,007 and 106,008 on Feb. 17, 2015.
Sontheimer, Erik J. et al., "Metal ion catalysis during splicing of premessenger RNA," Nature, vol. 388:801-805 (1997) (Exhibit No. 1036 filed in interferences 106008, 106007 on Nov. 18, 2014).
Sontheimer, Erik J. et al., "The U5 and U6 Small Nuclear RNAs as Active Site Components of the Spliceosome," Science, vol. 262:1989-1997 (1993) (Exhibit No. 105B filed in interferences 106006, 106007 on Nov. 18, 2014).
Standard Operating Procedure FPLC Desalting, pp. 6, Exhibit No. 1144 filed in Interferences 106,007 and 106,008 on Feb. 16, 2015.
Stanton, Robert et al., "Chemical Modification Study of Antisense Gapmers", Nucleic Acid Therapeutics, vol. 22(5):344-359 (2012).
Statement on a Nonproprietary Name Adopted by the USAN Council, ETEPLIRSEN, Chemical Structure, 2010, pp. 1-5.
Stein, CA, "Delivery of antisense oligonucleotides to cells: a consideration of some of the barriers," Monographic supplement series: Oligos & Peptides—Chimica Oggi—Chemistry Today, vol. 32(2):4-7 (2014) (Exhibit No. 2022 filed in interferences 106008, 106013, 106007 on Nov. 18, 2014).
Stein, Cy A. et al., "Therapeutic Oligonucleotides: The Road Not Taken," Clin. Cancer Res., vol. 17(20):6369-6372 (2011) (Exhibit No. 2026 filed in interferences 106008, 106013, 106007 on Nov. 18, 2014).
Stein, David et al., "A Specificity Comparison of Four Antisense Types: Morpholino, 2'-O-Methyl RNA, DNA, and PHosphorothioate DNA," Antisense & Nucleic Acid Drug Development, vol. 7:151-157 (1997).
Strober JB, "Therapeutics in Duchenne muscular dystrophy," NeuroRX 2006; 3:225-34.
Summary of Professional Experience (Dr. Erik J Sontheimer), pp. 4, Exhibit No. 1223 filed in Interferences 106,007 and 106,008 on Feb. 17, 2015.
Summerton, James et al., "Morpholino and Phosphorothioate Antisense Oligomers Compared in Cell-Free and In-Cell Systems," Antisense & Nucleic Acid Drug Development, vol. 7:63-70 (1997).
Summerton, James et al., "Morpholino Antisense Oligomers: Design, Preparation, and Properties," Antisense & Nucleic Acid Drug Development, vol. 7:187-195 (1997).
Summerton, James, "Morpholino antisense oligomers: the case for an Rnase H-independent structural type," Biochimica et Biophysica Acta, vol. 1489:141-158 (1999) (Exhibit No. 1038 filed in interferences 106008, 106013, 106007 on Nov. 18, 2014).
Supplementary European Search Report for Application No. 10829367.1, 8 pages, dated May 22, 2013.
Suter et al., "Double-target antisense U7 snRNAs promote efficient skipping of an aberrant exon in three human Beta-thalassemic

(56) References Cited

OTHER PUBLICATIONS mutations," 8:13 Human Molecular Genetics 2415-2423 (1999) (Exhibit No. 1083 filed in interferences 106008, 106007 on Dec. 23, 2014).

T Hoen, Peter A.C. et al., "Generation and Characterization of Transgenic Mice with the Full-length Human DMD Gene," The Journal of Biological Chemistry, vol. 283:(9):5899-5907 (2008) Exhibit No. 2030 filed in interferences 106008, 106013, 106007 on Nov. 18, 2014).

Table 1: Primer and Product Details for Exon 51 and 53 Reports on AONs of 20 to 50 Nucleotides dd Jan. 7, 2015, pp. 1, Exhibit No. 1177 filed in Interferences 106,007 and 106,008 on Feb. 16, 2015.

Takeshima et al., "Oligonucleotides against a splicing enhancer sequence led to dystrophin production in muscle cells from a Duchenne muscular dystrophy patient," Brain & Dev., vol. 23, pp. 788-790 (2001), Exhibit No. 1196 filed in Interferences 106,007 and 106,008 on Feb. 17, 2015.

Takeshima, Yasuhiro et al., "Modulation of In Vitro Splicing of the Upstream Intron by Modifying an Intra-Exon Sequence Which Is Deleted from the Dystrophin Gene in Dystrophin Kobe," J. Clin. Invest., vol. 95:515-520 (1995).

Tanaka, Kenji et al., "Polypurine Sequences within a Downstream Exon Function as a Splicing Enhancer," Molecular and Cellular Biology, vol. 14(2):1347-1354 (1994).

Thanh, Le Thiet et al., "Characterization of Revertant Muscle Fibers in Duchenne Muscular Dystrophy, Using Exon-Specific Monoclonal Antibodies against Dystrophin," Am. J. Hum. Genet., vol. 56:725-731 (1995).

*The Regents of the University of California v. Dako North America, Inc.*, U.S.D.C., N.D. California, No. C05-03955 MHP, Apr. 22, 2009 (2009 WL 1083446 (N.D.Cal.), Exhibit No. 1206 filed in Interferences 106,007 and 106,008 on Feb. 17, 2015.

Tian, Xiaobing et al., "Imaging Oncogene Expression," Ann. N.Y. Acad. Sci., vol. 1002:165-188 (2003) (Exhibit No. 2029 filed in interferences 106008, 106013, 106007 on Nov. 18, 2014).

Transcript of 2nd Deposition of Erik J. Sontheimer, Ph.D., dated Mar. 12, 2015, (Academisch Ziekenhuis Leiden Exhibit 1231, filed Apr. 3, 2015 in Interference 106007 and 106008, pp. 1-185).

Transcript of 2nd Deposition of Matthew J.A. Wood, M.D., D. Phil, dated Mar. 5, 2015, (Academisch Ziekenhuis Leiden Exhibit 1230, filed Apr. 3, 2015 in Interference 106007 and 106008, pp. 1-117).

Transcript of Dec. 12, 2014 Teleconference with Administrative Patent Judge Schafer (rough draft) (previously filed in Int. No. 106,008 as Ex. 2114), pp. 28 Exhibit No. 1001 filed in Interference 106,013 on Feb. 17, 2015.

Transcript of the Jan. 21, 2015 deposition of Erik Sontheimer, Ph.D., Patent Interference Nos. 106,007 and 106,008, 98 pages, dated Jan. 21, 2015 (Exhibit No. 2122 filed in interferences 106,007 and 106,008 on Feb. 17, 2015.

Transcript of the Mar. 11, 2015 deposition of Judith van Deutekom, Ph.D., (University of Western Australia Exhibit 2141, filed Apr. 3, 2015 in Interferences 106007, 106008, and 106013, pp. 1-168).

Transcript of the Mar. 12, 2015 deposition of Erik J. Sontheimer, Ph.D., (University of Western Australia Exhibit 2142, filed Apr. 3, 2015 in Interferences 106007, 106008, and 106013, pp. 1-183).

Transcript of the Mar. 5, 2015 deposition of Matthew J. A. Wood, M.D., D. Phil., (University of Western Australia Exhibit 2146, filed Apr. 3, 2015 in Interferences 106007, 106008, and 106013, pp. 1-115).

Transfection of AON, pp. 1, Exhibit No. 1170 filed in Interferences 106,007 and 106,008 on Feb. 16, 2015.

U.S. Food and Drug Administration Statement, dated Dec. 30, 2014 (2 pages), Exhibit No. 1204 filed in Interferences 106,007 and 106,008 on Feb. 17, 2015.

U.S. Appl. No. 12/198,007, as-filed Aug. 25, 2008 ("the '007 Application") (Exhibit No. 1073 filed in interferences 106008, 106007 on Dec. 23, 2004).

U.S. Appl. No. 12/976,381, filed Dec. 22, 2010 ("The '381 Application") (Exhibit No. 1074 filed in interferences 106008, 106007 on Dec. 23, 2014).

U.S. Patent Application Publication No. 2001/0056077 ("Matsuo") 10 pages, (Exhibit No. 1080 filed in interferences 106008, 106007 on Dec. 23, 2014).

U S. Patent Application Publication No. 2002/0049173 ("Bennett et al.") 50 pages, (Exhibit No. 1081 filed in interferences 106008, 106007 on Dec. 23, 2014).

U.S. Pat. No. 5,190,931 ("The '931 Patent") 22 pages,(Exhibit No. 1069 filed in interferences 106008, 106007 on Dec. 23, 2014).

U.S. Pat. No. 7,001,761 (the "Xiao" Patent) 64 pages, (Exhibit No. 1070 filed in interferences 106008, 106007 on Dec. 23, 2014).

University of Western Australia Objections to Opposition Evidence, served on Feb. 24, 2015 filed in Interference No. 106,007, Exhibit 2150, filed Apr. 10, 2015 in Interference Nos. 106007 and 106008, pp. 1-15.

University of Western Australia Objections to Opposition Evidence, served on Feb. 24, 2015, filed in Interference No. 106,008, Exhibit 2151, filed Apr. 10, 2015, in Interference Nos. 106007and 106008, pp. 1-15.

*University of Western Australia v. Academisch Ziekenhuis Leiden*, Academisch Ziekenhuis Leiden List of Exhibits (as of Apr. 3, 2015), filed in Patent Interference No. 106,007, Apr. 3, 2015, pp. 1-18, (Doc 423).

*University of Western Australia v. Academisch Ziekenhuis Leiden*, Academisch Ziekenhuis Leiden List of Exhibits (as of Apr. 3, 2015), filed in Patent Interference No. 106,008, Apr. 3, 2015, pp. 1-18 (Doc 435).

*University of Western Australia v. Academisch Ziekenhuis Leiden*, Academisch Ziekenhuis Leiden List of Exhibits, 18 pages, Patent Interference No. 106,007, (Doc 391), dated Feb. 17, 2015.

*University of Western Australia v. Academisch Ziekenhuis Leiden*, Academisch Ziekenhuis Leiden List of Exhibits, 18 pages, Patent Interference No. 106,008, (Doc 398), dated Feb. 17, 2015.

*University of Western Australia v. Academisch Ziekenhuis Leiden*, Academisch Ziekenhuis Leiden List of Exhibits, 3 pages, Patent Interference No. 106,013, (Doc 147), dated Feb. 17, 2015.

*University of Western Australia v. Academisch Ziekenhuis Leiden*, Academisch Ziekenhuis Leiden Notice of Service of Supplemental Evidence; 3 pages, Patent Interference No. 106,007 (Doc 414), dated Mar. 9, 2015.

*University of Western Australia v. Academisch Ziekenhuis Leiden*, Academisch Ziekenhuis Leiden Notice of Service of Supplemental Evidence, 3 pages, Patent Interference No. 106,008 (Doc 422), dated Mar. 9, 2015.

*University of Western Australia v. Academisch Ziekenhuis Leiden*, Academisch Ziekenhuis Leiden Opposition 1 (35 U.S.C. § 112(a)), 83 pages, Patent Interference. No. 106,008, (Doc 400), dated Feb. 17, 2015.

*University of Western Australia v. Academisch Ziekenhuis Leiden*, Academisch Ziekenhuis Leiden Opposition 1 (35 U.S.C. § 112(a)), 93 pages, Patent Interference No. 106,007, (Doc 392), dated Feb. 17, 2015.

*University of Western Australia v. Academisch Ziekenhuis Leiden*, Academisch Ziekenhuis Leiden Opposition 1 (Standing Order ¶ 203.1 and 37 C.F.R. § 41.202(a) and (e)), 20 pages, Patent Interference No. 106,013, (Doc 148), dated Feb. 17, 2015.

US Transmittal, application as-filed, and Preliminary Amendment for U.S. Appl. No. 13/270,992, 101 pages, dated Oct. 11, 2011 (Exhibit No. 2098 filed in interferences 106008, 106013, 106007 on Nov. 18, 2014).

US Transmittal, application as-filed, and Preliminary Amendment for U.S. Appl. No. 13/271,080, 115 pages, dated Oct. 11, 2011 (Exhibit No. 2111 filed in interferences 106008, 106013, 106007 on Nov. 18, 2014).

US Updated Filing Receipt for U.S. Appl. No. 13/550,210, 3 pages, dated Dec. 11, 2012 (Exhibit No. 2044 filed in interferences 106008, 106013, 106007 on Nov. 18, 2014).

USPTO "2014 Procedure for Subject Matter Eligibility Analysis of Claims Reciting or Involving . . . Natural Products" ("The March Guidance"), 19 pages, (Exhibit No. 2118 filed in interferences 106,007 and 105,008 on Feb. 17, 2015.

USPTO Written Description Training Materials, Revised Mar. 25, 2008, Example 12, 6 pages, (Exhibit No. 1068 filed in interferences 106008, 106007 on Dec. 23, 2014.

(56) References Cited

OTHER PUBLICATIONS

UWA Clean Claims and Sequence, as filed in Interference No. 106,007 on Aug. 1, 2014 (Paper 12), 8 pages, (Exhibit No. 2126 filed in interferences 106,007 and 106,008 on Feb. 17, 2015.

UWA Clean Claims and Sequence, as filed in Interference No. 106,007 on Aug. 7, 2014 (Paper 12), 8 pages, (Exhibit No. 2127 filed in interferences 106,007 and 106,008 on Feb. 17, 2015.

UWA Motion 1 (For Judgment Under 35 § 112(a)) from Int. No. 106,007 (PN210), 40 Pages, Exhibit No. 1005 filed in Interference 106,013 on Feb. 17, 2015.

UWA Motion 1 (For Judgment Under 35 § 112(a)) from Int. No. 106,008 (Doc 213), pp. 38, Exhibit No. 1004 filed in Interference 106,013 on Feb. 17, 2015.

UWA submission of teleconference transcript , 28 pages, dated Dec. 12, 2014 (Exhibit No. 2114 filed in interferences 106008 and 106007 on Dec. 12, 2014).

Valorization Memorandum published by the Dutch Federation of University Medical Centers in Mar. 2009, (University of Western Australia Exhibit 2140, filed Apr. 3, 2015 in Interferences 106007, 106008, and 106013, pp. 1-33).

Van Deutekom et al., "Antisense-induced exon skipping restores dystrophin expression in DMD patient derived muscle cells," Human Molecular Genetics vol. 10, No. 15: 15.47-1554 (2001)(Exhibit No. 1084 filed in interferences 106008, 106007 on Dec. 23, 2014).

Van Deutekom et al., "Local Dystrophin Restoration with Antisense Oligonucleotide PRO051," N. Engl. J. Med., vol. 357, No. 26, pp. 2677-2686 (Dec. 2007), Exhibit No. 1213 filed in Interferences 106,007 and 106,008 on Feb. 17, 2015.

Van Deutekom, Judith C. T., et al., "Advances in Duchenne Muscular Dystrophy Gene Therapy," Nature Reviews Genetics, vol. 4(10):774-783 (2003).

Van Ommen 2002 PCT (WO 02/24906 A1), 43 pages,(Exhibit No. 1071 filed in interferences 106008, 106007 on Dec. 23, 2014).

Van Putten M, et al., The Effects of Low Levels of Dystrophin on Mouse Muscle Function and Pathology. PLoS ONE 2012;7:e31937, 13 pages.

Van Vliet, Laura et al., "Assessment of the Feasibility of Exon 45-55 Multiexon Skipping for Duchenne Muscular Dystrophy" BMC Medical Genetics, vol. 9(1):105 (2008).

Verma, Sandeep et al., "Modified Olgonucleotides: Synthesis and Strategy for Users," Annu. Rev. Biochem., vol. 67:99-134 (1998) (Exhibit No. 1040 filed in interferences 106008, 106007 on Nov. 18, 2014).

Voit, Thomas et al., "Safety and efficacy of drisapersen for the treatment of Duchenne muscular dystrophy (DEMAND II): an exploratory, randomised, placebo-controlled phase 2 study," Lancet Neurol., vol. 13:987-996 (2014) (Exhibit No. 2037 filed in interferences 106008, 106013, 106007 on Nov. 18, 2014).

Volloch, Vladimir et al., "Inhibition of Pre-mRNA Splicing by Antisense RNA in Vitro: Effect of RNA Containing Sequences Complementary to Exons," Biochemical and Biophysical Research Communications, vol. 179 (3):1593-1599 (1991).

Wahlestedt et al., "Potent and nontoxic antisense oligonucleotides containing locked nucleic acids," PNAS, vol. 97, No. 10, pp. 5633-5638 (May, 2000). Exhibit No. 1201 filed in Interferences 106,007 and 106,008 on Feb. 17, 2015.

Wang et al., "In Vitro evaluation of novel antisense oligonucleotides is predictive of in vivo exon skipping activity for Duchenne muscular dystrophy," J. Gene Medicine, vol. 12, pp. 354-364 (Mar. 2010), Exhibit No. 1115 filed in interferences 106,007 and 106,008 on Feb. 17, 2015.

Wang, Chen-Yen et al., "pH-sensitive immunoliposomes mediate target-cell-specific delivery and controlled expression of a foreign gene in mouse," Proc. Natl. Acad. Sci. USA, vol. 84:7851-7855 (1987).

Watakabe, Akiya et al., "The role of exon sequences in splice site selection," Genes & Development, vol. 7:407-418 (1993).

Watanabe et al., "Plasma Protein Binding of an Antisense Oligonucleotide Targeting Human ICAM-1 (ISIS 2302)," Oligonucleotides, vol. 16, pp. 169-180 (2006), Exhibit No. 1197 filed in Interferences 106,007 and 106,008 on Feb. 17, 2015.

Wijnaendts, L.C.D. et al., "Prognostic importance of DNA flow cytometric variables in rhabdomyosarcomas," J. Clin. Pathol., vol. 46:948-952 (1993) (Exhibit No. 1041 filed in interferences 106008, 106007 on Nov. 18. 2014).

Wilton et al. (2007) "Antisense Oligonucleotide-induced Exon Skipping Across the Human Dystrophin Gene Transcript," Molecular Therapy 15(7)1288-1296, 10 pages, (Exhibit No. 2121 filed in interferences 106,007 and 106,008 on Feb. 17, 2015.

Wilton, Stephen D. et al., "Antisense oligonucleotides in the treatment of Duchenne muscular dystrophy: where are we now?" Neuromuscular Disorders, vol. 15:399-402 (2005).

Wilton, Stephen D. et al., "Specific removal of the nonsense mutation from the mdx dystrophin mRNA using antisense oligonucleotides," Neuromuscular Disorders, vol. 9:330-338 (1999).

WO 2002/24906 A1 of AZL, (University of Western Australia Exhibit 2134, filed Apr. 3, 2015 in Interferences 106007, 106008, and 106013, pp. 1-43.).

WO 2004/083432 (the published AZL PCT Application "Van Ommen"), pp. 71, Exhibit No. 1003 filed in interference 106,013 on Feb. 17, 2015.

WO 2013/112053 A1, (University of Western Australia Exhibit 2130, filed Apr. 3, 2015 in Interferences 106007, 106008, and 106013, pp. 1-177).

Wolff, Jon A. et al., "Direct Gene Transfer into Mouse Muscle in Vivo," Science, vol. 247:1465-1468 (1990).

Wong, Marisa L. et al., "Real-time PCR for mRNA quantitation," BioTechniques, vol. 39:75-85 (2005) (Exhibit No. 1066 flied in interferences 106008, 106007 on Nov. 18, 2014).

Wood, "Toward an Oligonucleotide Therapy for Duchenne Muscular Dystrophy: A Complex Development Challenge," Science Translational Medicine, vol. 2, No. 25, pp. 1-6 (Mar. 2010), Exhibit No. 1116 filed in interferences 106,007 and 106,008 on Feb. 17, 2015,Doc 335.

Written Opinion for Application No. PCT/AU2010/001520, 6 pages, dated Jan. 21, 2011.

Wu, B. et al., "Dose-dependent restoration of dystrophin expression in cardiac muscle of dystrophic mice by systemically delivered morpholino," Gene Therapy, vol. 17:132-140 (2010).

Wu, Bo et al., "Effective rescue of dystrophin improves cardiac function in dystrophin-deficient mice by a modified morpholino oligomer," PNAS, vol. 105(39):14814-14819 (2008).

Wu, Bo et al., "Targeted Skipping of Human Dystrophin Exons in Transgenic Mouse Model Systemically for Antisense Drug Development," PLoS One, vol. 6(5):e19906, 11 pages (2011).

Wu, George Y. et al., "Receptor-mediated Gene Delivery and Expression in Vivo," The Journal of Biological Chemistry, vol. 263(29):14621-14624 (1988).

Wu, George Y. et al., "Receptor-medated in Vitro Gene Transformation by a Soluble DNA Carrier System," The Journal of Biological Chemistry, vol. 262(10):4429-4432 (1987).

Wyatt et al. "Site-specific cross-linking of mammalian U5 snRNP to the 5' splice site before the first step of pre-mRNA splicing," Genes & Development, vol. 6, pp. 2542-2553 (1992), Exhibit No. 1196 filed in Interferences 106,007 and 106,008 on Feb. 17, 2015.

Yin et al., "A fusion peptide directs enhanced systemic dystrophin exon skipping and functional restoration in dystrophin-deficient mdx mice," Human Mol. Gen., vol. 18, No. 22, pp. 4405-4414 (2009), Exhibit No. 1200 filed in Interferences 106,007 and 106,008 on Feb. 17, 2015.

Yin et al., "Cell Penetrating peptide-conjugated antisense oligonucleotides restore systemic muscle and cardiac dystrophin expression and function," Human Mol. Gen., vol. 17, No. 24, pp. 3909-3918 (2008), Exhibit No. 1199 filed in Interferences 106,007 and 106,008 on Feb. 17, 2015.

Yin et al., "Functional Rescue of Dystrophin-deficient mdx Mice by a ChimericPeptide-PMO," Mol. Therapy, vol. 18, No. 10, pp. 1822-1829 (Oct. 2010), Exhibit No. 1117 filed in interferences 106,007 and 106,008 on Feb. 17. 2015.

Yokota et al., "Efficacy of Systematic Morpholino Exon-Skipping in Duchenne Dystrophy Dogs," American Neurological Assoc., vol.

(56) References Cited

OTHER PUBLICATIONS

65. No. 6, pp. 667-676 (Jun. 2009), Exhibit No. 1214 filed in Interferences 106,007 and 106,008 on Feb. 17, 2015.

*Zoltek Corp. v U.S.*, 95 Fed. Cl. 681 (2011), 23 pages, (Academisch/tekenhuis Leiden Exhibit 1236, filed May 5, 2015 in Interference 106007 and 106008).

File Excerpts from Prosecution History of U.S. Appl. No. 13/270,992 (UWA's U.S. Pat. No. 8,486,907), pp. 122, Exhibit No. 1006 filed in Interference 106,013 on Feb. 17, 2015.

Hoffman EP, et al., "Restoring dystrophin expression in Duchenne muscular dystrophy muscle: Progress in exon skipping and stop codon read through," Am J Path 2011;179:12-22.

Hudziak, Robert M. et al., "Antiproliferative Effects of Steno Blocking Phosphorodiamidate Morpholino Antisense Agents Directed against c-myc," Antisense & Nucleic Acid Drug Development, vol. 10:163-176 (2000) (Exhibit No. 1032 filed in interferences 106008, 106007 on Nov. 18, 2014).

Hudziak, Robert M. et al., "Resistance of Morpholino Phosphorodiamidate Oligomers to Enzymatic Degradation," Antisense & Nucleic Acid Drug Development, vol. 6:267-272 (1996).

Hussey, Nicole D. et al., "Analysis of five Duchenne muscular dystrophy exons and gender determination using conventional duplex polymerase chain reaction on single cells," Molecular Human Reproduction, vol. 5(11):1089-1094 (1999).

Interim Guidance on Patent Subject Matter Eligibility ("the December Guidance," 16 pages,(Exhibit No. 2119 filed in interferences 106,007 and 106,008 on Feb. 17, 2015.

International Patent Application No. PCT/AU2000/00693 ("Wraight"), published as WO 00/78341 dated Dec. 28, 2000, 201 pages, (Exhibit No. 2125 filed in interferences 106,007 and 106,008 on Feb. 17, 2015.

International Preliminary Report on Patentability and Written Opinion for Application No. PCT/US2009/061960, 8 pages, dated Apr. 26, 2011.

International Preliminary Report on Patentability for Application No. PCT/AU2005/000943, 8 pages, dated Dec. 28, 2006.

International Preliminary Report on Patentability, PCT/US2013/077216, dated Jun. 23, 2015, pp. 1-7.

International Preliminary Report on Patentability, PCT/US2014/029610, dated Jul. 1, 2015, pp. 1-122.

International Search Report and Written Opinion of the International Searching Authority issued in International Patent Application No. PCT/US2013/077216, 5 pages, dated Mar. 27, 2014.

International Search Report and Written Opinion of the International Searching Authority issued in International Patent Application No. PCT/US2014/029610, 6 pages, dated Sep. 18, 2014.

International Search Report and Written Opinion of the International Searching Authority issued in International Patent Application No. PCT/US2014/029689, 8 pages, dated Oct. 21, 2014.

International Search Report and Written Opinion of the International Searching Authority issued in International Patent Application No. PCT/US2014/029766, 8 pages, dated Oct. 21, 2014.

International Search Report for Application No. PCT/AU2005/000943, 5 pages, dated Oct. 20, 2005.

International Search Report for Application No. PCT/US01/14410, 5 pages, dated Mar. 6, 2002.

International Search Report for Application No. PCT/US2009/061960, 9 pages, dated Apr. 6, 2010.

Invitation to pay fees and Partial International Search Report issued by the International Search Authority in International Patent Application No. PCT/US2014/029689, 8 pages, dated Jul. 29, 2014.

ISIS Pharmaceuticals website, 2 pages, http://www.isispharm.com/Pipeline/Therapeutic-Areas/Other.htm (2014) (Exhibit No. 2021 filed in interferences 106008, 106013, 106007 on Nov. 18, 2014).

Iversen, Patrick L. et al., "Efficacy of Antisense Morpholino Oligomer Targeted to c-myc in Prostate Cancer Xenograft Murine Model and a Phase I Safety Study in Humans," Clinical Cancer Research, vol. 9:2510-2519 (2003).

Jarver, Peter et al., "A Chemical View of Oligonucleotides for Exon Skipping and Related Drug Applications," Nucleic Acid Therapeutics, vol. 24(1):37-47 (2014) (Exhibit No. 2061 filed in interferences 106008, 106013, 106007 on Nov. 18, 2014).

Jason, Tracey L.H. et al., "Toxicology of antisense therapeutics," Toxicology and Applied Pharmacology, vol. 201:66-83 (2004) (Exhibit No. 2027 filed in interferences 106008, 106013, 106007 on Nov. 18, 2014).

Jearawiriyapaisarn, Natee et al., "Long-term improvement in mdx cardiomyopathy after therapy with peptide-conjugated morpholino oligomers," Cardiovascular Research, vol. 35:444-453 (2010).

Jearawiriyapaisarn, Natee et al., "Sustained Dystrophin Express Induced by Peptide-conjugated Morpholino Oligomers in the Muscles of mdx Mice," Mol. Ther., vol. 16(9):1624-1629 (2008).

Job Posting by Sarepta for "Scientist II, Muscle Biology" (2 pages), (Academisch Ziekenhuis Leiden Exhibit 1233, filed Apr. 3, 2015 in Interference 106007 and 106008).

Jones, Simon S. et al., "The Protection of Uracil and Guanine Residues in Oligonucleotide Synthesis," Tetrahedron Letters, vol. 22(47):4755-4758 (1981).

Karlen, Yann et al., "Statistical significance of quantitative PCR," BMC Bioinformatics, 8:131, 16 pages (2007) (Exhibit No. 1033 filed in interferences 106003, 106007 on Nov. 18, 2014).

Karras, James G. et al., "Deletion of Individual Exons and Induction of Soluble Murine Interleukin-5 Receptor-alpha Chain Expression through Antisense Oligonucleotide-Mediated Redirection of Pre-mRNA splicing," Molecular Pharmacology, vol. 58:380-387 (2000).

Kaye, Ed, "Results of the Eteplirsen Phase 2b and Phase 2b Extension Study in Duchenne Muscular Dystrophy," 8th Annual Meeting of the Oligonucleotide Therapeutics Society, Session 9: Advances in Oligonucleotide Clinical Development II, p. 48 (2012).

Kinali, Maria el al., "Local restoration of dystrophin expression with the morpholino oligomer AVI-4658 in Duchenne muscular dystrophy: a single-blind, placebo-controlled, dose-escalation, proof-of-concept study," Lancet Neurol., vol. 8:918-928 (2009).

King et al., "A Dictionary of Genetics," Oxford University Press, 4th Ed. (1990), Exhibit No. 1189 filed in Interferences 106,007 and 106,008 on Feb. 17, 2015.

Koenig, M. et al., "The Complete Sequence of Dystrophin Predicts a Rod-Shaped Cytoskeleton Protein," Cell, vol. 53:219-223 (1988) (Exhibit No. 1010 filed in interferences 106003, 106007 on Nov. 18, 2014).

Koenig, M. et al., "The Molecular Basis for Duchenne versus Becker Muscular Dystrophy: Correlation of Severity with Type of Deletion," Am. J. Hum. Genet., vol. 45:498-506 (1989) (Exhibit No. 1011 filed in interferences 106008, 106007 on Nov. 18, 2014).

Kohler M, et al., "Quality of life, physical disability and respiratory impairment in Duchenne muscular dystrophy," Am J Respir Crit Care Med 2005;172:1032-6.

Koshkin, Alexei A. et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54:3607-3630 (1998) (Exhibit No. 2007 filed in interferences 106008, 106013, 106007 on Nov. 18, 2014).

Kurreck J., "Antisense Technologies: Improvement Through Novel Chemical Modifications", European Journal of Biochemistry, vol. 270(8):1628-1644 (2003).

Lab-on-a-Chip Data, pp. 28, Exhibit No. 1185 filed in Interferences 106,007 and 106,008 on Feb. 16, 2015.

Laboratory Notebook Entry (Exon 51 Experiments): RT-PCR Analysis of 8036 Cells, pp. 2, Exhibit No. 1179 filed in Interferences 106,007 and 106,008 on Feb. 16, 2015.

Laboratory Notebook Entry (Exon 51 Experiments): RT-PCR Analysis of KM155.C25 Cells, pp. 2, Exhibit No. 1178 filed in Interferences 106,007 and 106,008 on Feb. 16, 2015.

Laboratory Notebook Entry (Exon 51 Experiments): Transfection of 8036 Cells, pp. 1, Exhibit No. 1172 filed in Interferences 106,007 and 106,008 on Feb. 16, 2015.

Laboratory Notebook Entry (Exon 51 Experiments): Transfection of KM155.C25 Cells, pp. 1, Exhibit No. 1171 filed in Interferences 106,007 and 106,008 on Feb. 16, 2015.

Laboratory Notebook Entry (Exon 53 Experiments): RT-PCR Analysis of KM155.C25 Cells, pp. 2, Exhibit No. 1180 filed in Interferences 106,007 and 106,008 on Feb. 16, 2015.

(56) References Cited

OTHER PUBLICATIONS

Laboratory Notebook Entry (Exon 53 Experiments): RT-PCR Analysis of R1809 Cells, pp. 2, Exhibit No. 1181 filed in Interferences 106,007 and 106,008 on Feb. 16, 2015.
Laboratory Notebook Entry (Exon 53 Experiments): Transfection of KM155.C25 Cells, pp. 1, Exhibit No. 1173 filed in Interferences 106,007 and 106,008 on Feb. 16, 2015.
Laboratory Notebook Entry (Exon 53 Experiments): Transfection of R1809 Cells, pp. 1, Exhibit No. 1174 filed in Interferences 106,007 and 106,008 on Feb. 16, 2015.
Laboratory Notebook Entry: General RNA recovery, 1 Page, Exhibit No. 1176 filed in Interferences 106,007 and 106,008 on Feb. 16, 2015.
Laboratory Notebook Entry: Lab-on-a-Chip Analysis, pp. 3, Exhibit No. 1184 filed in Interferences 106,007 and 106,008 on Feb. 16, 2015.
Larsen et al., "Antisense properties of peptide nucleic acid," Biochim. Et Biophys. Acta, vol. 1489, pp. 159-166 (1999), Exhibit No. 1190 filed in Interferences 106,007 and 106,008 on Feb. 17, 2015.
List of Publications for Matthew J. A. Wood, M.D., D. Phil., 11 pages, (Exhibit No. 2124 filed in interferences 106,007 and 106,008 on Feb. 17, 2015.
Liu, Hong-Xiang et al., "Identification of functional exonic splicing enhancer motifs recognized by individual SR proteins," Genes & Development, vol. 12:1998-2012 (1998).
Lu et al, "Massive Idiosyncratic Exon Skipping Corrects the Nonsense Mutation in Dystrophic Mouse Muscle and Produces Functional Revertant Fibers by Clonal Expansion," The Journal of Cell Biology, vol. 148(5):985-995, Mar. 6, 2000 ("Lu et al.") (Exhibit No. 1082 filed in interferences 106008, 106007 on Dec. 23, 2014).
Lu, Qi Long et al., "Functional amounts of dystrophin produced by skipping the mutated exon in the mdx dystrophic mouse," Nature Medicine, vol. 9(8):1009-1014 (2003).
Lu, Qi-long et al., "What Can We Learn From Clinical Trials of Exon Skipping for DMD?" Molecular Therapy—Nucleic Acids, vol. 3:e152, doi.10.1038/mtna.2014.6, 4 pages (2014).
Lyophilisation of Oligonucleotides, pp. 2, Exhibit No. 1133 filed in Interferences 106,007 and 106,008 on Feb. 17, 2015.
Mann, Christopher J. et al., "Antisense-induced exon skipping and synthesis of dystrophin in the mdx mouse," PNAS, vol. 98(1):42-47 (2001).
Mann, Christopher J. et al., "Improved antisense oligonucleotide induced exon skipping in the mdx mouse model of muscular dystrophy," The Journal of Gene Medicine, vol. 4:644-654 (2002).
Mannino, Raphael J. et al., "Liposome Mediated Gene Transfer," BioTechniques, vol. 6(7):682-690 (1988).
Manual of Patent Examining Procedure 2308.02 (6th ed., rev. 3, Jul. 1997), (University of Western Australia Exhibit 2143, filed Apr. 3, 2015 in Interferences 106007, 106008, and 106013, pp. 1-2).
Manzur A, et al.,. "Glucocorticoid corticosteroids for Duchenne muscular dystrophy," Cochrane Database Syst Rev. 2004;(2):CD003725.
Marshall, N.B. et al., "Arginine-rich cell-penetrating peptides facilitate delivery of antisense oligomers into murine leukocytes and alter pre-mRNA splicing," Journal of Immunological Methods, vol. 325:114-126 (2007).
Mathews et al., "Expanded Sequence Dependence of Thermodynamic Parameters Improves Prediction of RNA Secondary Structure," J. Mol. Biol. 288:911-940 (1999), (University of Western Australia Exhibit 2131, filed Apr. 3, 2015 in Interferences 106007, 106008, and 106013, pp. 1-31).
Mathews et al., "Expanded Sequence Dependence of Thermodynamic Parameters Improves Prediction of RNA Secondary Structure," J. Mol. Biol., vol. 288, pp. 911-940 (1999), Exhibit No. 1212 filed in Interferences 106,007 and 106,008 on Feb. 17, 2015.
Matsuo, Masafumi et al., "Exon Skipping during Splicing of Dystrophin mRNA Precursor due to an Intraexon Deletion in the Dystrophin Gene of Duchenne Muscular Dystrophy Kobe," J. Clin. Invest., vol. 87:2127-2131 (1991).
Matsuo, Masafumi et al., "Treatment of Duchenne Muscular Dystrophy with Oligonucleotides against an Exonic Splicing Enhancer Sequence," Basic Appl. Myol., vol. 13(6):281-285 (2003).
Matsuo, Masafumi, "Duchenne and Becker Muscular Dystrophy: From Gene Diagnosis to Molecular Therapy," IUBMB Life, vol. 53:147-152 (2002).
Matsuo, Masafumi, "Duchenne/Becker muscular dystrophy: from molecular diagnosis to gene therapy," Brain & Develoment, vol. 18:167-172 (1996).
Matteucci, Mark, "Structural modifications toward improved antisense oligonucleotides," Perspectives in Drug Discovery and Design, vol. 4:1-16 (1996).
Mazzone E, et al. "Functional changes in Duchenne muscular dystrophy: a 12-month longitudinal cohort study," Neurology 2011:77(3):250-6.
McCarville, M. Beth et al., "Rhabdomyosarcoma in Pediatric Patients: The Good, the Bad, and the Unusual," AJR, vol. 176:1563-1569 (2001) (Exhibit No. 1034 filed in interferences 106008, 106007 on Nov. 18, 2014).
McClorey, G. et al., "Antisense oligonucleotide-induced axon skipping restores dystrophin expression in vitro in a canine model of DMD," Gene Therapy, vol. 13:1373-1381 (2006).
McClorey, G. et al., "Induced dystrophin exon skipping in human muscle explants," Neuromuscular Disorders, vol. 16:583-590 (2006).
McClorey, Graham et al., "Splicing intervention for Duchenne muscular dystrophy," Current Opinion in Pharmacology, vol. 5:529-534 (2005).
McDonald CM, et al., "Profiles of Neuromuscular Diseases, Duchenne muscular dystrophy," Am J Phys Med Rehabil 1995;74:S70-S92.
McDonald CM, et al., "The 6-minute walk test as a new outcome measure in Duchenne muscular dystrophy," Muscle Nerve 2010:41:500-10.
McDonald CM, et al., "The 6-minute walk test in Duchenne/Becker muscular dystrophy: longitudinal observations," Muscle Nerve 2010;42: 966-74.
Mendell JR et al., "Evidence-based path to newborn screening for Duchenne muscular Dystrophy," Ann Neurol , 2012;71:304-13.
Mendell JR, et al., "Dystrophin immunity revealed by gene therapy in Duchenne muscular dystrophy," N Engl J Med 2010; 363:1429-37.
Mendell JR, et al., "Randomized, double-blind six-month trial of prednisone in Duchenne's muscular dystrophy," N Engl J Med 1989;320:1592-97.
Mendell, Jerry R. et al., "Eteplirsen for the Treatment of Duchenne Muscular Dystrophy," Ann. Neurol., vol. 74:637-647 (2013) (Exhibit No. 2058 filed in interferences 106008, 106013, 106007 on Nov. 18, 2014).
Mendell, Jerry R. et al., "Eteplirsen in Duchenne Muscular Dystrophy (DMD): 144 Week Update on Six-Minute Walk Test (6MWT) and Safety," slideshow, presented at the 19th International Congress of the World Muscle Society, 17 pages (2014) (Exhibit No. 2059 filed in interferences 106008, 106013, 106007 on Nov. 18, 2014).
Mendell, Jerry R. et al., "Gene therapy for muscular dystrophy: Lessons learned and path forward," Neuroscience Letters, vol. 527:90-99 (2012).
Merlini L, et al., "Early corticosteroid treatment in 4 Duchenne muscular dystrophy patients: 14-year follow-up," Muscle Nerve 2012;45:796-802.
Mfold illustrations for Exon 51 and Exon 53 with varying amounts of intron sequence, (University of Western Australia Exhibit 2132, filed Apr. 3, 2015 in Interferences 106007, 106008, and 106013, pp. 1-21.
Mitrpant, Chalermchai et al., "Rational Design of Antisense Oligomers to Induce Dystrophin Exon Skipping," Molecular Therapy, vol. 17(8):1418-1426 (2009).
Monaco, Anthony P. et al., "An Explanation for the Phenotypic Differences between Patients Bearing Partial Deletions of the DMD Locus," Genomics, vol. 2:90-95 (1988).
Morcos, Paul A., "Gene switching analyzing a broad range of mutations using steric block antisense oligonucleotides," Methods in Enzymology, vol. 313:174-189 (1999).

(56) References Cited

OTHER PUBLICATIONS

Moulton, H.M., "Compound and Method for Treating Myotonic Dystrophy," U.S. Appl. No. 12/493,140, 82 pages, filed Jun. 26, 2009.

Moulton, Hong M. et al., "Morpholinos and their peptide conjugates: Therapeutic promise and challenge for Duchenne muscular dystrophy," Biochimica et Biophysica Acta, vol. 1798:2296-2303 (2010).

Muntoni F, et al., "Dystrophin and mutations: one gene, several proteins, multiple phenotypes," Lancet Neurol. 2003;2:731-40.

Muntoni, Francesco et al., "128th ENMC International Workshop on 'Preclinical optimization and Phase I/II Clinical Trials Using Antisense Oligonucleotides in Duchenne Muscular Dystrophy' Oct. 22-24, 2004, Naarden, The Netherlands," Neuromuscular Disorders, vol. 15:450-457 (2005) (Exhibit No. 2025 filed in Interferences 106008, 106013, 106007 on Nov. 18, 2014).

Muntoni, Francesco et al., "149th ENMC International Workshop and 1st TREAT-NMD Workshop on: 'Planning Phase I/II Clinical trials using Systemically Delivered Antisense Oligonucleotides in Duchenne Muscular Dystrophy,'" Neuromuscular Disorders, vol. 18:268-275 (2008).

Nelson, David L. et al., "Nucleotides and Nucleic Acids," Lehninger Principles of Biochemistry, 3rd Edition, Chapter 10, pp. 325-328 and glossary p. G-11, Worth Publishers, New York (2000).

Nguyen TM, et. al., "Use of Epitope libraries to identify exon-specific monoclonal antibodies for characterization of altered dystrophins in muscular dystrophy," Am J Hum Genet 1993;52:1057-66.

Oberbauer, "Renal uptake of an 18-mer phosphorothioate oligonucleotide," Kidney Int'l, vol. 48, pp. 1226-1232 (1995), Exhibit No. 1191 filed in Interferences 106,007 and 106,008 on Feb. 17, 2015.

Oligonucleotide Cleavage and Deprotection Laboratory Notebook Entry, pp. 1, Exhibit No. 1138 filed in Interferences 106,007 and 106,008 on Feb. 16, 2015.

Oligonucleotide diagrams, 5 pages (Exhibit No. 1053 filed in interferences 106008, 106007 on Nov. 18, 2014).

Partial European Search Report for Application No. 10004274.6, 6 pages, dated Oct. 2, 2012.

Partial European Search Report for Application No. 12162995.0, 6 pages, dated Oct. 2, 2012.

Patentee's Response to European Patent Application No. 05076770.6, dated Jul. 28, 2006, 4 pages.

*Patrick O. Brown and Tidear D. Shalon v. Stephen P.A. Fodor, Dennis W. Solas and William J. Dower*: Interference Merits Panel, Interference No. 104,358, 24 pages, dated Aug. 9, 1999 (Exhibit No. 2113 filed in interferences 106008, 106013, 106007 on Nov. 18, 2014).

*University of Western Australia v. Academisch Ziekenhuis Leiden*, University of Western Australia Request for Oral Argument, filed in Patent Interference No. 106,007, Apr. 10, 2015, pp. 1-4 (Doc 457).

*University of Western Australia v. Academisch Ziekenhuis Leiden*, University of Western Australia Request for Oral Argument, filed in Patent Interference No. 106,008, Apr. 10, 2015, pp. 1-4 (Doc 465).

*University of Western Australia v. Academisch Ziekenhuis Leiden*, University of Western Australia Request for Oral Argument, filed in Patent Interference No. 106,013, Apr. 10. 2015, pp. 1-3 (Doc 190).

*University of Western Australia v. Academisch Ziekenhuis Leiden*, University of Western Australia Revised Designation of Lead and Backup Counsel, 4 pages, Patent Interference No. 106,007, (Doc 415), dated Mar. 10, 2015.

*University of Western Australia v. Academisch Ziekenhuis Leiden*, University of Western Australia Revised Designation of Lead and Backup Counsel, 4 pages, Patent Interference No. 106,013, (Doc 150 ), dated Mar. 10, 2015.

*University of Western Australia v. Academisch Ziekenhuis Leiden*, University of Western Australia Revised Designation of Lead and Backup Counsel, 5 pages, Patent Interference No. 106,006, (Doc 423 ), dated Mar. 10, 2015.

*University of Western Australia v. Academisch Ziekenhuis Leiden*, University of Western Australia, Exhibit List as of Feb. 17, 2015, 8 pages, Patent Interference No. 106,007, (Doc No. 398) dated Feb. 17, 2015.

*University of Western Australia v. Academisch Ziekenhuis Leiden*, University of Western Australia, Exhibit List as of Feb. 17, 2015, 8 pages, Patent Interference No. 106,008, (Doc No. 406) dated Feb. 17, 2015.

*University of Western Australia v. Academisch Ziekenhuis Leiden*, UWA Clean Involved Claims and Sequence, Patent Interference No. 106,007, 8 pages, dated Aug. 1, 2014 (Doc 12).

*University of Western Australia v. Academisch Ziekenhuis Leiden*, UWA Clean Involved Claims and Sequence, Patent Interference No. 106,013, 7 pages, dated Oct. 14, 2014 (Doc 7).

*University of Western Australia v. Academisch Ziekenhuis Leiden*, UWA Clean Involved Claims and Sequences, Patent Interference No. 106,008, 8 pages, dated Aug. 7, 2014 (Doc 12).

*University of Western Australia v. Academisch Ziekenhuis Leiden*, UWA Exhibit List as of Nov. 18, 2014, 7 pages, Patent Interference No. 106,008, dated Nov. 18, 2014 (Doc 216).

*University of Western Australia v. Academisch Ziekenhuis Leiden*, UWA Exhibit List, 7 pages, Patent Interference No. 106,007, dated Nov. 18, 2014 (Doc 213).

*University of Western Australia v. Academisch Ziekenhuis Leiden*, UWA Exhibit List, 7 pages, Patent Interference No. 106,013, dated Nov. 18, 2014 (Doc 134).

*University of Western Australia v. Academisch Ziekenhuis Leiden*, UWA Exhibit List, 7 pages, Patent Interference No. 106,008, dated Dec. 12, 2014 (Doc 221).

*University of Western Australia v. Academisch Ziekenhuis Leiden*, UWA Exhibit List, 8 pages, Patent Interference No. 106,007, dated Dec. 12, 2014 (Doc 217).

*University of Western Australia v. Academisch Ziekenhuis Leiden*, UWA List of Proposed Motions, Patent Interference No. 106,007, 7 pages, dated Sep. 10, 2014 (Doc 17).

*University of Western Australia v. Academisch Ziekenhuis Leiden*, UWA List of Proposed Motions, Patent Interference No. 106,008, 6 pages, dated Sep. 10, 2014 (Doc 16).

*University of Western Australia v. Academisch Ziekenhuis Leiden*, UWA Miscellaneous Motion 1 (for authorization to file terminal disclaimer), 5 pages, Patent Interference No. 106,008, dated Oct. 17, 2014 (Doc 22).

*University of Western Australia v. Academisch Ziekenhuis Leiden*, UWA Motion 1 (For Judgment Under 35 U.S.C., section 112(a)), 40 pages, Patent Interference No. 106,007, dated Nov. 18, 2014 (Doc 210).

*University of Western Australia v. Academisch Ziekenhuis Leiden*, UWA Motion 1 (For Judgment Under 35 § 112(a)) Patent Interference No. 106,008 (Doc 213), 38 Pages, on Nov. 18, 2014.

*University of Western Australia v. Academisch Ziekenhuis Leiden*, UWA Motion 1 (To Maintain Interference between UWA U.S. Pat. No. 8,486,907 and AZL U.S. Appl. No. 14/198,992), 45 pages, Patent Interference No. 106,013, dated Nov. 18, 2014 (Doc 133).

*University of Western Australia v. Academisch Ziekenhuis Leiden*, UWA Motion 2 (For Judgment Under 35 U.S.C. section 112(b)), 32 pages, Patent Interference No. 106,008, dated Nov. 18, 2014 (Doc 214).

*University of Western Australia v. Academisch Ziekenhuis Leiden*, UWA Motion 2 (For Judgment Under 35 U.S.C. section 112(b)), 34 pages, Patent Interference No. 106,007, dated Nov. 18, 2014 (Doc 211).

*University of Western Australia v. Academisch Ziekenhuis Leiden*, UWA Motion 3 (For judgment that Claims 11-12, 14-15, and 17-29 of U.S. Appl. No. 13/550,210 are barred under 35 U.S.C. section 135(b)), 25 Pages, Patent Interference No. 106,008, dated Nov. 18, 2014 (Doc 215).

*University of Western Australia v. Academisch Ziekenhuis Leiden*, UWA Motion 3 Requesting an additional Interference between UWA U.S. Pat. No. 8,455,636 and AZL U.S. Appl. No. 14/248,279, 36 pages, Patent Interference No. 106,007, dated Nov. 18, 2014 (Doc 212).

(56) References Cited

OTHER PUBLICATIONS

*University of Western Australia v. Academisch Ziekenhuis Leiden*, UWA Notice of Filing Priority Statement, 2 pages, Patent Interference No. 106,007, dated Nov. 18, 2014 (Doc 215).
*University of Western Australia v. Academisch Ziekenhuis Leiden*, UWA Notice of Filing Priority Statement, 2 pages, Patent Interference No. 106,008, dated Nov. 18, 2014 (Doc 218).
*University of Western Australia v. Academisch Ziekenhuis Leiden*, UWA Notice of Recent Authority, filed in Patent Interference No. 106,007, Jul. 2, 2015, pp. 1-16 (Doc 469).
*University of Western Australia v. Academisch Ziekenhuis Leiden*, UWA Notice of Recent Authority, filed in Patent Interference No. 106,008, Jul. 2, 2015, pp. 1-16 (Doc 477).
*University of Western Australia v. Academisch Ziekenhuis Leiden*, UWA Notice of Related Proceedings, Patent Interference No. 106,007, 3 pages, dated Aug. 1, 2014 (Doc 11).
*University of Western Australia v. Academisch Ziekenhuis Leiden*, UWA Notice of Related Proceedings, Patent Interference No. 106,008, 5 pages, dated Aug. 7, 2014 (Doc 11).
*University of Western Australia v. Academisch Ziekenhuis Leiden*, UWA Notice of Related Proceedings, Patent Interference No. 106,013, 3 pages, dated Oct. 14, 2014 (Doc 6).
U.S. Pat. No. 7,960,541 (Wilton et al.), pp. 84; Exhibit No. 1002 filed in interferences 106,007 and 106,008 on Nov. 18, 2014.
U.S. Pat. No. 8,450,474 (Wilton et al.), pp. 95; Exhibit No. 1087 filed in interferences 106,007 and 106,008 on Feb. 13, 2015.
U.S. Pat. No. 8,455,634 (Wilton et al.) pp. 96, Exhibit No. 1088 filed in interferences 106,007 and 106,008 on Feb. 13, 2015.
U.S. Pat. No. 8,455,635 (Wilton et al.), pp. 96, Exhibit No. 1089 filed in interferences 106,007 and 106,008 on Feb. 13, 2015.
U.S. Pat. No. 8,455,636 (Wilton et al.), pp. 92; Exhibit No. 1003 filed in interferences 106,007 and 106,008 on Nov. 18, 2014.
U.S. Pat. No. 8,476,423 (Wilton et al.), pp. 95; Exhibit No. 1111 filed in interferences 106,007 and 106,008 on Feb. 13, 2015.
U.S. Pat. No. 8,501,703 (Bennett et al.), pp. 16, Exhibit No. 1090 filed in interferences 106,007 and 106,008 on Feb. 13, 2015.
U.S. Pat. No. 8,501,704 (Mourich et al.), pp. 39, Exhibit No. 1091 filed in interferences 106,007 and 106,008 on Feb. 13, 2015.
U.S. Pat. No. 8,524,676 (Stein et al.), pp. 28, Exhibit No. 1092 filed in interferences 106,007 and 106,008 on Feb. 13, 2015.
U.S. Pat. No. 8,524,880 (Wilton et al.), pp. 89, Exhibit No. 1093 filed in interferences 106,007 and 106,008 on Feb. 13, 2015.
U.S. Pat. No. 8,536,147 (Weller el al.), pp. 95, Exhibit No. 1094 filed in interferences 106,007 and 106,008 on Feb. 17, 2015.
U.S. Pat. No. 8,592,386 (Mourich et al.), pp. 46, Exhibit No. 1095 filed in interferences 106,007 and 106,008 on Feb. 13, 2015.
U.S. Pat. No. 8,618,270 (Iversen et al.), pp. 28, Exhibit No. 1096 filed in interferences 106,007 and 106,008 on Feb. 13, 2015.
U.S. Pat. No. 8,637,483 (Wilton et al.), pp. 157, Exhibit No. 1097 filed in interferences 106,007 and 106,008 on Feb. 13, 2015.
U.S. Pat. No. 8,697,858 (Iversen), pp. 95, Exhibit No. 1098 filed in interferences 106,007 and 106,008 on Feb. 13, 2015.
U.S. Pat. No. 8,703,735 (Iversen et al.) pp. 73, Exhibit No. 1099 filed in interferences 106,007 and 106,008 on Feb. 13, 2015.
U.S. Pat. No. 8,741,863 (Moulton et al.), pp. 68, Exhibit No. 1100 filed in interferences 106,007 and 106,008 on Feb. 13, 2015.
*University of Western Australia v. Academisch Ziekenhuis Leiden*, Academisch Ziekenhuis Leiden Opposition 2 (Indefiniteness), 31 pages, Patent Interference No. 106,007, (Doc 396), dated Feb. 17, 2015.
*University of Western Australia v. Academisch Ziekenhuis Leiden*, Academisch Ziekenhuis Leiden Opposition 2 (Indefiniteness), 32 pages, Patent Interference No. 106,008, (Doc 401), dated Feb. 17, 2015.
*University of Western Australia v. Academisch Ziekenhuis Leiden*, Academisch Ziekenhuis Leiden Opposition 3 (35 U.S.C. §135(b)), 44 pages, Patent Interference No. 106,008, (Doc 397), dated Feb. 17, 2015.
*University of Western Australia v. Academisch Ziekenhuis Leiden*, Academisch Ziekenhuis Leiden Opposition 3 (Standing Order § 203.1 and 37 C.F.R. § 41.202(a) and (e)), 20 pages, Patent Interference No. 106,007, (Doc 389), dated Feb. 17, 2015.
*University of Western Australia v. Academisch Ziekenhuis Leiden*, Academisch Ziekenhuis Leiden Reply 1 (For Judgment that UWA'a Claims are Unpatentable Under 35 U.S.C. §§ 102 and 103), dated Apr. 3, 2015, filed in Patent Interference No. 106008, pp. 1-17 (Doc 431).
*University of Western Australia v. Academisch Ziekenhuis Leiden*, Academisch Ziekenhuis Leiden Reply 1 (For Judgment that UWA's Claims are Unpatentable Under 35 U.S.C. §§ 102 and 103), dated Apr. 3, 2015, filed in Patent Interference No. 106007, pp. 1-17 (Doc 424).
*University of Westem Australia v. Academisch Ziekenhuis Leiden*, Academisch Ziekenhuis Leiden Reply 2 (To Deny the Benefit of AU 2004903474), dated Apr. 3, 2015, filed in Patent Interference No. 106007, pp. 1-11(Doc 425).
*University of Western Australia v. Academisch Ziekenhuis Leiden*, Academisch Ziekenhuis Leiden Reply 2 (To Deny the Benefit of AU 2004903474), dated Apr. 3, 2015, filed in Patent Interference No. 106008, pp. 1-12 (Doc 432).
*University of Western Australia v. Academisch Ziekenhuis Leiden*, Academisch Ziekenhuis Leiden Reply 3 (For Judgment of Unpatentability based on Myriad) dated Apr. 3, 2015, filed in Patent Interference No. 106007, pp. 1-12 (Doc 426).
*University of Western Australia v. Academisch Ziekenhuis Leiden*, Academisch Ziekenhuis Leiden Reply 3 (For Judgment of Unpatentability based on Myriad) dated Apr. 3, 2015, filed in Patent Interference No. 106008, pp. 1-13 (Doc 433).
*University of Western Australia v. Academisch Ziekenhuis Leiden*, Academisch Ziekenhuis Leiden Reply 4 (In Support of Responsive Motion 4 to Add Two New Claims) dated Apr. 3, 2015, filed in Patent Interference No. 106007, pp. 1-17 (Doc 427).
*University of Western Australia v. Academisch Ziekenhuis Leiden*, Academisch Ziekenhuis Leiden Reply 4 (In Support of Responsive Motion 4 to Add Two New Claims) dated Apr. 3, 2015, filed in Patent Interference No. 106008, pp. 1-17 (Doc 434).
*University of Western Australia v. Academisch Ziekenhuis Leiden*, Academisch Ziekenhuis Leiden Request for Oral Argument, filed in Patent Interference No. 106,007, Apr. 10, 2015, pp. 1-3 (Doc 454).
*University of Western Australia v. Academisch Ziekenhuis Leiden*, Academisch Ziekenhuis Leiden Request for Oral Argument, filed in Patent Interference No. 106,008, Apr. 10. 2015, pp. 1-3 (Doc 462).
*University of Western Australia v. Academisch Ziekenhuis Leiden*, Academisch Ziekenhuis Leiden Responsive Motion 4 (To Add Two New Claims), 57 pages, Patent Interference No. 106,008, (Doc 245), dated Dec. 23, 2014.
*University of Western Australia v. Academisch Ziekenhuis Leiden*, Academisch Ziekenhuis Leiden Responsive Motion 4 (To Add Two New Claims), 65 pages, Patent Interference No. 106,007, (Doc 241), dated Dec. 23, 2014.
*University of Western Australia v. Academisch Ziekenhuis Leiden*, Academisch Ziekenhuis Leiden Statement Regarding Oral Argument, filed in Patent interference No. 106,013, Apr. 10, 2015, pp. 1-3 (Doc 189).
*University of Western Australia v. Academisch Ziekenhuis Leiden*, Academisch Ziekenhuis Leiden's List of Exhibits as of May 5, 2015, filed in Patent Interference No. 106,007, May 5, 2015, pp. 1-18 (Doc 466).
*University of Western Australia v. Academisch Ziekenhuis Leiden*, Academisch Ziekenhuis Leiden's List of Exhibits as of May 5, 2015, filed in Patent Interference No. 106,008, May 5, 2015, pp. 1-18 (Doc 474).
*University of Western Australia v. Academisch Ziekenhuis Leiden*, Academisch Ziekenhuis Leiden's Opposition 4 (To Not Exclude Evidence), filed in Patent Interference No. 106,007, May 5, 2015, pp. 1-22 (Doc 465).
*University of Western Australia v. Academisch Ziekenhuis Leiden*, Academisch Ziekenhuis Leiden's Opposition 4 (To Not Exclude Evidence), filed in Patent Interference No. 106,008, May 5, 2015, pp. 1-21 (Doc 473).

(56) References Cited

OTHER PUBLICATIONS

*University of Western Australia v. Academisch Ziekenhuis Leiden*, Academisch Ziekenhuis Leiden's Second Supplemental Notice of Real Party in Interest, filed in Patent Interference No. 106,007, May 28, 2015, pp. 1-3, (Doc 468).
*University of Western Australia v. Academisch Ziekenhuis Leiden*, Academisch Ziekenhuis Leiden's Second Supplemental Notice of Real Party in Interest, filed in Patent Interference No. 106,008, May 28, 2015, pp. 1-3, (Doc 476).
*University of Western Australia v. Academisch Ziekenhuis Leiden*, Academisch Ziekenhuis Leiden's Second Supplemental Notice of Real Party in Interest, filed in Patent Interference No. 106013, May 28, 2015, pp. 1-3, (Doc 191).
*University of Western Australia v. Academisch Ziekenhuis Leiden*, Academish Ziekenhuis Leiden Supplemental Notice of Real Party in Interest, pp. 3, Doc 149, Patent Interference No. 106,013 dated Feb. 23, 2015.
*University of Western Australia v. Academisch Ziekenhuis Leiden*, Academish Ziekenhuis Leiden Supplemental Notice of Real Party in Interest, pp. 3, Doc 413, Patent Interference No. 106,007 dated Feb. 23, 2015.
*University of Western Australia v. Academisch Ziekenhuis Leiden*, Academish Ziekenhuis Leiden Supplemental Notice of Real Party in Interest, pp. 3. Doc 421, Patent Interference No. 106,0008 dated Feb. 23, 2015.
*University of Western Australia v. Academisch Ziekenhuis Leiden*, Amendment and Response, U.S. Appl. No. 11/233,495, filed Jan. 22, 2014, 8 pages, (Exhibit No. 2117 filed in interferences 106,007 and 106, 008, on Feb. 17, 2015.
*University of Western Australia v. Academisch Ziekenhuis Leiden*, AZL Annotated Claims, Patent Interference No. 106,007, 15 pages, dated Aug. 15, 2014 (Doc 15).
*University of Western Australia v. Academisch Ziekenhuis Leiden*, AZL Annotated Claims, Patent Interference No. 106,008, 14 pages, dated Aug. 21, 2014 (Doc 14).
*University of Western Australia v. Academisch Ziekenhuis Leiden*, AZL Annotated Claims, Patent Interference No. 106,013, 14 pages, dated Oct. 27, 2014 (Doc 16).
*University of Western Australia v. Academisch Ziekenhuis Leiden*, AZL Clean Claims and Sequence, filed in Patent Interference No. 106,013, 5 pages, dated Oct. 15, 2014 ((Doc 12).
*University of Western Australia v. Academisch Ziekenhuis Leiden*, AZL Corrected Notice of Related Proceedings, Patent Interference No. 106,007, 3 pages, dated Aug. 1, 2014 (Doc 13).
*University of Western Australia v. Academisch Ziekenhuis Leiden*, AZL Exhibit List, 10 pages, Patent Interference No. 106,007 dated Dec. 23, 2014 (Doc 240).
*University of Western Australia v. Academisch Ziekenhuis Leiden*, AZL Exhibit List, 10 pages, Patent Interference No. 106,008, dated Dec. 23, 2014 (Doc 244).
*University of Western Australia v. Academisch Ziekenhuis Leiden*, AZL List of Exhibits, 9 pages, Patent Interference No. 106,007, dated Nov. 18, 2014 (Doc 209).
*University of Western Australia v. Academisch Ziekenhuis Leiden*, Azl List of Exhibits, as of Nov. 8, 2014, 9 pages, Patent Interference No. 106,008, dated Nov. 18, 2014 (Doc 212).
*University of Western Australia v. Academisch Ziekenhuis Leiden*, AZL List of Proposed Motions, Patent Interference No. 106,007, 6 pages, dated Sep. 10, 2014 (Doc 16).
*University of Western Australia v. Academisch Ziekenhuis Leiden*, AZL List of Proposed Motions, Patent Interference No. 106,008, 8 pages, dated Sep. 10, 2014 (Doc 15).
*University of Western Australia v. Academisch Ziekenhuis Leiden*, AZL Motion 1 (For Judgment that UWA's Claims are Unpatentable Under 35 U.S.C. sections 102 and 103), 69 pages, Patent Interference No. 106,007, dated Nov. 18, 2014 (Doc 181).
*University of Western Australia v. Academisch Ziekenhuis Leiden*, AZL Motion 1 (For Judgment that UWA's Claims are Unpatentable Under 35 U.S.C. sections 102 and 103), 69 pages, Patent Interference No. 106,008, dated Nov. 18, 2014 (Doc 184).

*University of Western Australia v. Academisch Ziekenhuis Leiden*, AZL Motion 2 (To Deny UWA the Benefit of AU 2004903474), 23 pages, Patent Interference No. 106,007, dated Nov. 18, 2014 (Doc 26).
*University of Western Australia v. Academisch Ziekenhuis Leiden*, AZL Motion 2 (To Deny UWA the Benefit of AU 2004903474), 24 pages, Patent Interference No. 106,008, dated Nov. 18, 2014 (Doc 29).
*University of Western Australia v. Academisch Ziekenhuis Leiden*, AZL Motion 3 (For Judgment of Unpatentability based on Myriad) 20 pages, Patent Interference No. 106,008, dated Nov. 18, 2014 (Doc 30).
*University of Western Australia v. Academisch Ziekenhuis Leiden*, AZL Motion 3 (For Judgment of Unpatentability based on Myriad), 19 pages, Patent Interference No. 106,007, dated Nov. 18, 2014 (Doc 27).
*University of Western Australia v. Academisch Ziekenhuis Leiden*, AZL Notice of Related Proceedings, Patent Interference No. 106,007, 3 pages, dated Jul. 31, 2014 (Doc 6).
*University of Western Australia v. Academisch Ziekenhuis Leiden*, AZL Notice of Related Proceedings, Patent Interference No. 106,008, 3 pages, dated Aug. 5, 2014 (Doc 7).
*University of Western Australia v. Academisch Ziekenhuis Leiden*, AZL Notice Related Proceedings, Patent Interference. No. 106,013, 3 pages, dated Oct. 15. 2014 (Doc 11).
*University of Western Australia v. Academisch Ziekenhuis Leiden*, Clean Claims and Sequences, 5 pages, dated Aug. 5, 2014, Interference No. 106,008, (Exhibit No. 2047 filed in interferences 106,008, 106,013, 106,007 on Nov. 18, 2014).
*University of Western Australia v. Academisch Ziekenhuis Leiden*, Clean Claims and Sequences, 5 pages, dated Jul. 31, 2014, Interference No. 106,007, (Exhbit No. 2045 filed in interferences 106,008, 106,013, 106,007 on Nov. 18, 2014).
*University of Western Australia v. Academisch Ziekenhuis Leiden*, Clean Claims and Sequences, 5 pages, dated Oct. 15, 2014., Interference No. 106,013, (Exhibit No. 2050 filed in interferences 106,008, 106,013, 106,007 on Nov. 18, 2014).
*University of Western Australia v. Academisch Ziekenhuis Leiden*, Decision—Motions—37 CFR§ 41.125(a), filed in Patent Interference No. 106,013, Jun. 22, 2015; pp. 1-12 (Doc 192).
*University of Western Australia v. Academisch Ziekenhuis Leiden*, Declaration of Erik Sontheimer dated Nov. 17, 2014, Exhibit 1012 filed in Patent Interference Nos. 106,007 and 106,008, 112 pages, filed Nov. 18, 2014.
*University of Western Australia v. Academisch Ziekenhuis Leiden*, Declaration of Interference, Patent Interference No. 106,007, 7 pages, dated Jul. 18, 2014 (Doc 1).
*University of Western Australia v. Academisch Ziekenhuis Leiden*, Declaration of Interference, Patent Interference No. 106,008, 7 pages, dated Jul. 24, 2014 (Doc 1).
*University of Western Australia v. Academisch Ziekenhuis Leiden*, Declaration of Interference, Patent Interference No. 106,013, 8 pages, dated Sep. 29, 2014 (Doc 1).
*University of Western Australia v. Academisch Ziekenhuis Leiden*, Declaration of Matthew J.A. Wood, Patent Interference Nos. 106,007, 106,008 and 106,013, 184 pages, dated Nov. 16, 2014 (Exhibit No. 2081 filed in interferences 106008, 106013, 106007 on Nov. 18, 2014).
*University of Western Australia v. Academisch Ziekenhuis Leiden*, Joint Stipulation regarding Time Periods 2, 3 and 4, 3 pages, Patent Interference No. 106,013, (Doc 135), dated Nov. 25, 2015.
*University of Western Australia v. Academisch Ziekenhuis Leiden*, Joint Stipulation regarding Time Periods 3-4, 4 pages, Patent Interference No. 106,007, (Doc 243), dated Jan. 29, 2015.
*University of Western Australia v. Academisch Ziekenhuis Leiden*, Joint Stipulation regarding Time Periods 3-4, 4 pages, Patent Interference No. 106,008, (Doc 247), dated Jan. 29, 2015.
*University of Western Australia v. Academisch Ziekenhuis Leiden*, Joint Stipulation regarding Time Periods 3-4, 4 pages, Patent Interference No. 106,013, (Doc 137), dated Jan. 29, 2015.
*University of Western Australia v. Academisch Ziekenhuis Leiden*, Joint Stipulation Regarding Time Periods 4-6, 4 pages, Patent Interference No. 106,007, dated Mar. 19, 2015 (Doc 416).

(56) References Cited

OTHER PUBLICATIONS

*University of Western Australia v. Academisch Ziekenhuis Leiden,* Joint Stipulation Regarding Time Periods 4-6, 4 pages, Patent Interference No. 106013, (Doc 151), dated Mar. 19, 2015.
*University of Western Australia v. Academisch Ziekenhuis Leiden,* Joint Stipulation Regarding Time Periods 4-6, 4 pages, Patent Interference No. 106,008, (Doc 424 ), dated Mar. 19, 2015.
*University of Western Australia v. Academisch Ziekenhuis Leiden,* Miscellaneous Order under 37 CFR 41.104(a), 4 pages, Patent Interference Nos. 106,007 and 106,008, dated Dec. 15, 2014.
*University of Western Australia v. Academisch Ziekenhuis Leiden,* Order—Authorizing Motions, Patent Interference No. 106,007, 3 pages, dated Sep. 26, 2014 (Doc 20).
*University of Western Australia v. Academisch Ziekenhuis Leiden,* Order—Authorizing Motions, Patent Interference No. 106,007, 6 pages, dated Sep. 23, 2014 (Doc 19).
*University of Western Australia v. Academisch Ziekenhuis Leiden,* Order—Authorizing Motions, Patent Interference No. 106,008, 6 pages, dated Sep. 23, 2014 (Doc 18).
*University of Western Australia v. Academisch Ziekenhuis Leiden,* Order—Miscellaneous 37 C.F.R. 41.104(a), 2 pages, Patent Interference Nos. 106,007, 106,008, 106,013, dated Nov. 14, 2014.
*University of Western Australia v. Academisch Ziekenhuis Leiden,* Order to Show Cause—37 CFR§ 41.104(a), filed in Patent Interference No. 106,013, Jun. 22, 2015, pp. 1-3 (Doc 193).
*University of Western Australia v. Academisch Ziekenhuis Leiden,* Redeclaration, Patent Interference. No. 106,008, 2 pages, dated Sep. 23, 2014 (Doc 19).
*University of Western Australia v. Academisch Ziekenhuis Leiden,* Second Declaration of Matthew J. A. Wood, M.D., D. Phil., Patent Interference Nos. 106007 and 106,008, 78 pages, dated Feb. 17, 2015 (Exhibit No. 2116 filed in interferences 106,007 and 106,008, on Feb. 17, 2015.
*University of Western Australia v. Academisch Ziekenhuis Leiden,* Statement Concerning Initial Settlement Discussions, 3 pages, Patent Interference No. 106,013, (Doc 136), dated Dec. 30, 2014.
*University of Western Australia v. Academisch Ziekenhuis Leiden,* Statement Concerning Subsequent Settlement Discussions, 3 pages, Patent Interference No. 106,007, (Doc 242), dated Dec. 30, 2014.
*University of Western Australia v. Academisch Ziekenhuis Leiden,* Statement Concerning Subsequent Settlement Discussions, 3 pages, Patent Interference No. 106,008, (Doc 246), dated Dec. 30, 2014.
*University of Western Australia v. Academisch Ziekenhuis Leiden,* University of Western Austalia Response to Order to Show Cause, filed in Patent Interference No. 106,013, Jul. 20, 2015, pp. 1-28 (Doc 194).
*University of Western Australia v. Academisch Ziekenhuis Leiden,* University of Western Australia Exhibit List as of Apr. 10, 2015, filed in Patent Interference No. 106,007, Apr. 10, 2015, pp. 1-10 (Doc 456).
*University of Western Australia v. Academisch Ziekenhuis Leiden,* University of Western Australia Exhibit List as of Apr. 10, 2015, filed in Patent Interference No. 106,008, Apr. 10, 2015, pp. 1-10 (Doc 464).
*University of Western Australia v. Academisch Ziekenhuis Leiden,* University of Western Australia Exhibit List as of Apr. 3, 2015, filed in Interference 106007, Apr. 3, 2015, pp. 1-10 (Doc 431).
*University of Western Australia v. Academisch Ziekenhuis Leiden,* University of Western Australia Exhibit List as of Apr. 3, 2015, filed in Interference 106008, Apr. 3, 2015, pp. 1-10 (Doc 439).
*University of Western Australia v. Academisch Ziekenhuis Leiden,* University of Western Australia Exhibit List as of Apr. 3, 2015, filed in Interference 106013, Apr. 3, 2015, pp. 1-10 (Doc 153).
*University of Western Australia v. Academisch Ziekenhuis Leiden,* University of Western Australia Miscellaneous Motion 4 (to exclude evidence), filed in Patent Interference No. 106,007, Apr. 10, 2015, pp. 1-21 (Doc 455).

*University of Western Australia v. Academisch Ziekenhuis Leiden,* University of Western Australia Miscellaneous Motion 4 (to exclude evidence), filed in Patent Interference No. 106,008, Apr. 10, 2015, pp. 1-21 (Doc 463).
*University of Western Australia v. Academisch Ziekenhuis Leiden,* University of Western Australia Opposition 1 (Regarding Patentability Under 35 U.S.C. § 102/103), 38 pages, Patent Interference No. 106,007, (Doc 393), dated Feb. 17, 2015.
*University of Western Australia v. Academisch Ziekenhuis Leiden,* University of Western Australia Opposition 1 (Regarding Patentability Under 35 U.S.C. § 102/103), 39 pages, Patent Interference No. 106,008, (Doc 402), dated Feb. 17, 2015.
*University of Western Australia v. Academisch Ziekenhuis Leiden,* University of Western Australia Opposition 2 (To Retain UWA's Benefit of AU 2004903474), 31 pages, Patent Interference No. 106,008, (Doc 403), dated Feb. 17, 2015.
*University of Western Australia v. Academisch Ziekenhuis Leiden,* University of Western Australia Opposition 2 (To Retain UWA's Benefit of AU 2004903474), 37 pages, Patent Interference No. 106,007, (Doc 394), dated Feb. 17, 2015.
*University of Western Australia v. Academisch Ziekenhuis Leiden,* University of Western Australia Opposition 3 (Regarding Patentability Under 35 U.S.C. §101), 22 pages, Patent Interference No. 106,007, (Doc 395), dated Feb. 17, 2015.
*University of Western Australia v. Academisch Ziekenhuis Leiden,* University of Western Australia Opposition 3 (Regarding Patentability Under 35 U.S.C. § 101), 22 pages, Patent Interference No. 106,008, (Doc 404), dated Feb. 17, 2015.
*University of Western Australia v. Academisch Ziekenhuis Leiden,* University of Western Australia Opposition 4 (To deny entry of AZL's Proposed New Claims 104 and 105), 36 pages, Patent Interference No. 106,007, (Doc 397), dated Feb. 17, 2015.
*University of Western Australia v. Academisch Ziekenhuis Leiden,* University of Western Australia Opposition 4 (To deny entry of AZL's Proposed New Claims 30 and 31), 36 pages, Patent Interference No. 106,008, (Doc 405), dated Feb. 17, 2015.
*University of Western Australia v. Academisch Ziekenhuis Leiden,* University of Western Australia Reply 1 (to AZL Opposition 1), filed Apr. 3, 2015 in Interference 106007, pp. 1-28 (Doc 428).
*University of Western Australia v. Academisch Ziekenhuis Leiden,* University of Western Australia Reply 1 (to AZL Opposition 1), filed Apr. 3, 2015 in Interference 106008, pp. 1-28 (Doc 436).
*University of Western Australia v. Academisch Ziekenhuis Leiden,* University of Western Australia Reply 1 (to maintain the Interference) filed Apr. 3, 2015 in Interference 106013, pp. 1-17 (Doc 152).
*University of Western Australia v. Academisch Ziekenhuis Leiden,* University of Western Australia Reply 2 (to AZL Opposition 2) filed Apr. 3, 2015 in Interference 106007, pp. 1-22 (Doc 429).
*University of Western Australia v. Academisch Liekenhuis Leiden,* University of Western Australia Reply 2 (to AZL Opposition 2) filed Apr. 3, 2015 in Interference 106008, pp. 1-22 (Doc 437).
*University of Western Australia v. Academisch Ziekenhuis Leiden,* University of Western Australia Reply 3 (for Judgment under 35 U.S.C, §135(b)) filed Apr. 3, 2015 in Interference 106008, pp. 1-19 (Doc 438).
*University of Western Australia v. Academisch Ziekenhuis Leiden,* University of Western Australia Reply 3 (to Institute an Interference) filed Apr. 3, 2015 in Interference 106007, pp. 1-17 (Doc 430).
*University of Western Australia v. Academisch Ziekenhuis Leiden,* University of Western Australia Reply 4 (To Exclude Evidence), filed in Patent Interference No. 106,007, May 12, 2015, pp. 1-13 (Doc 467).
*University of Western Australia v. Academisch Ziekenhuis Leiden,* University of Western Australia Reply 4 (To Exclude Evidence), filed in Patent Interference No. 106,008, May 12, 2015, pp. 1-13 (Doc 475).
PCT Application as-filed for application No. PCT/NL03/00214, 71 pages, dated Sep. 21, 2005 (Exhibit No. 2042 filed in interferences 106008, 106013, 106007 on Nov. 18, 2014).
PD-10 Desalting Columns, pp. 12, Exhibit No. 1141 filed in Interferences 106,007 and 106,008 on Feb. 16, 2015.
Popplewell, Linda et al., "Design of phosphorodiamidate morpholino oligmers (PMOs) for the induction of exon skipping of the human

(56) References Cited

OTHER PUBLICATIONS

DMD gene," Human Gene Therapy 19(10): ESGCT 2008 Poster Presentations, p. 1174, Poster No. P203.
Popplewell, Linda J. et al., "Comparative analysis of antisense oligonucleotide sequences targeting exon 53 of the human DMD gene: Implications for future clinical trials," Neuromuscular Disorders, vol. 20(2): 102-110 (2010) 9 pages (Exhibit No. 2031 filed in interferences 106008, 106013, 106007 on Nov. 18, 2014).
Popplewell, Linda J. et al., "Design of Antisense Oligonucleotides for Exon Skipping of the Human Dystrophin Gene," Human Gene Therapy 19(4): BSGT 2008 Poster Presentation, p. 407, Poster No. P-35.
Popplewell, Linda J. et al., "Design of Phosphorodiamidate Morpholino Oligomers (PMOs) for the Induction of Exon Skipping of the Human DMD Gene," Molecular Therapy, vol. 17(3):554-561 (2009).
Popplewell, Linda J. et al., "Targeted Skipping of Exon 53 of the Human DMD Gene Recommendation of the Highly Efficient Antisense Oligonucleotide for Clinical Trial," Human Gene Therapy 20(4): BSGT 2009 Poster Presentations, p. 399, Poster No. P10.
Poster Abstract listing for The Tenth Annual Meeting of the RNA Society, held at the Banff Centre for Conferences, in Banff, Alberta, Canada, from May 24-29, 2005, (University of Western Australia Exhibit 2137, filed Apr. 3, 2015 in Interferences 106007, 106008, and 106013, pp. 1-11).
Pramono, "Induction of Exon Skipping of the Dystrophin Transcript in Lymphoblastoid Cells by Transfecting an Antisense Oligodeoxynucleotide Complementary to an Exon Recognition Sequence," Biochem. and Biophy. Res. Comm., vol. 226, pp. 445-449 (1996), Exhibit No. 1192 filed in Interferences 106,007 and 106,008 on Feb. 17, 2015.
Preliminary Amendment for U.S. Appl. No. 12/976,381, 4 pages, dated Dec. 22, 2010 (Exhibit No. 2066 filed in interferences 106008, 106013, 106007 on Nov. 18, 2014).
Preliminary Amendment for U.S. Appl. No. 12/198,007, 3 pages, dated Nov. 7, 2008 (Exhibit No. 2067 filed in interferences 106008, 106013, 106007 on Nov. 18, 2014).
Program Schedule for The Tenth Annual Meeting of the RNA Society, held at the Banff Centre for Conferences, in Banff, Alberta, Canada, from May 24-29, 2005, (University of Western Australia Exhibit 2136, filed Apr. 3, 2015 in Interferences 106007, 106008, and 106013, pp. 1-4).
Proliferation and Differentiation of Myoblast Cultures, pp. 2, Exhibit No. 1169 filed in Interferences 106,007 and 106,008 on Feb. 16, 2015.
Prosensa Press Release, dated Oct. 10, 2014 (2 pages), Exhibit No. 1203 filed in Interferences 106,007 and 106,008 on Feb. 17, 2015.
Prosensa, "GSK and Prosensa Announce Primary Endpoint Not Met in Phase III Study of Drisapersen in Patients With Duchenne Muscular Dystrophy," press release, 4 pages, dated Sep. 20, 2013 (Exhibit No. 2039 filed in interferences 106008, 106013, 106007 on Nov. 18, 2014).
*Raz et al.* v. *Davis et al.*, Board of Patent Appeals and Inteferences, Patent and Trademark Office, Int. No. 105,712, Tech. Ctr. 1600, Sep. 29, 2011 (24 pages) (2011 WL 4568986 (Bd.Pat.App. & Interf.), Exhibit No. 1209 filed in Interferences 106,007 and 106,008 on Feb. 17, 2015.
Reese, Colin B. et al., "Reaction Between 1-Arenesulphonyl-3-Nitro-1,2,4-Triazoles and Nucleoside Base Residues. Elucidation of the Nature of Side-Reactions During Oligonucleotide Synthesis," Tetrahedron Letters, vol. 21:2265-2268 (1980).
Reese, Colin B. et al., "The Protection of Thymine and Guanine Residues in Oligodeoxyribonucleotide Synthesis," J. Chem. Soc. Perkin Trans. 1, pp. 1263-1271 (1984).
Reexamination Certificate—U.S. Appl. No. 90/011,320, issued Mar. 27, 2012, 2 pages, (Exhibit No. 1072 filed in interferences 106008, 106007 on Dec. 23, 2014).
Reply to EPO Communication dated Jun. 26, 2014 in European Application Serial No. 13160338, (University of Western Australia Exhibit 2145, filed Apr. 3, 2015 in Interferences 106007, 106008, and 106013, pp. 14).
Reply to EPO Communication dated Oct. 21, 2014 in European Application Serial No. 12198517, (University of Western Australia Exhibit 2148, filed Apr. 3, 2015 in Interferences 106007, 106008, and 106013, pp. 1-7).
Reply to EPO Communication dated Oct. 23, 2014 in European Application Serial No. 12198485, (University of Western Australia Exhibit 2147, filed Apr. 3, 2015 in Interferences 106007, 106008, and 106013, pp. 1-8).
Response to Office Action and Amendments to the Claims for U.S. Appl. No. 13/550,210, 10 pages, dated May 12, 2014 (Exhibit No. 2064 filed in interferences 106008, 106013, 106007 on Nov. 18, 2014).
Rhodes et al., "BioMarin Bulks Up," BioCentuly, pp. 6-8 (Dec. 2014), Exhibit No. 1193 filed in Interferences 106,007 and 106,008 on Feb. 17, 2015.
RNA Isolation Using RNA-BEE, pp. 1, Exhibit No. 1175 filed in Interferences 106,007 and 106,008 on Feb. 16, 2015.
Roberts, Roland G. et al., "Exon Structure of the Human Dystrophin Gene," Genomics, vol. 16:536-538 (1993).
Roest et al., "Application of In Vitro Myo-Differentiation of Non-Muscle Cells to Enhance Gene Expression and Facilitate Analysis of Muscle Proteins," Neuromuscul. Disord., vol. 6, No. 3, pp. 195-202 (May 1996), Exhibit No. 1124 filed in interferences 106,007 and 106,008 on Feb. 17, 2015.
Rosso, Mario G. et al., "An *Arabidopsis thaliana* T-DNA mutagenized population (GABI-Kat) for flanking sequence tag-based reverse genetics," Plant Molecular Biology, vol. 53:247-259 (2003).
Saito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, Abstract [136] 1 page.
Saito, T. et al., "First-in-Human Study of NS-065/NCNP-01; the Morpholino Based Antisense Oglionucleotide for Exon 53 Skipping in Duchenne Muscular Dystrophy," ASGCT meeting, May 13, 2015, pp. 1-11.
Sarepta Therapeutics Press Release, dated Jan. 12, 2015, Exhibit No. 1119 filed in interferences 106,007 and 106,008 on Feb. 17, 2015.
Sarepta, "AVI BioPharma Initiates Dosing in Phase 2 Study of Eteplirsen in Duchenne Muscular Dystrophy Patients," press release, 4 pages, dated Aug. 15, 2011 (Exhibit No. 2082 filed in interferences 106008, 106013, 106007 on Nov. 18, 2014).
Sarepta, "Sarepta Therapeutics Announces Eteplirsen Demonstrates Continued Stability on Walking Test through 120 Weeks in Phase lib Study in Duchenne Muscular Dystrophy," press release, 3 pages, dated Jan. 15, 2014 (Exhibit No. 2034 filed in interferences 106008, 106013, 106007 on Nov. 18, 2014).
Sarepta, "Sarepta Therapeutics Reports Long-Term Outcomes through 144 Weeks from Phase IIb Study of Eteplirsen in Duchenne Muscular Dystrophy," press release, http://investorrelations.sarepta.com/phoenix.zhtml?c=64231&p=irol-newsArticle&id=1946426, 4 pages, dated Jul. 10, 2014.
Scully, Michele et al., "Review of Phase II and Phase III Clinical Trials for Duchenne Muscular Dystrophy", Expert Opinion on Orphan Drugs, vol. 1(1):33-46 (2013).
Second Preliminary Amendment filed in U.S. Appl. No. 13/550,210, 5 pages, dated Jan. 3, 2013 (Exhibit No. 2062 filed in interferences 106008, 106013, 106007 on Nov. 18, 2014).
Second Written Opinion for Application No. PCT/AU2010/001520, 7 pages, dated Oct. 13, 2011.
Semi Quantitative Lab-on-Chip Analysis of Second PCR Product, pp. 1, Exhibit No. 1183 filed in Interferences 106,007 and 106,008 on Feb. 16, 2015.
Sequence Listing—U.S. Appl. No. 13/550,210, filed Jul. 16, 2012 (9 pages), Exhibit No. 1205 filed in Interferences 106,007 and 106,008 on Feb. 17, 2015.
Sequence of Exon 46 of Dystrophin Gene, 1 page.
Sequence of Exon 51 of Dystrophin Gene, 1 page.
Shabanpoor et al., "Bi-specific splice-switching PMO oligonucleotides conjugated via a single peptide active in a mouse model of Duchenne muscular dystrophy," Nucleic Acids Res., pp. 1-11 (Dec. 2014), Exhibit No. 1114 filed in interferences 106,007 and 106,008 on Feb. 17, 2015.

(56) References Cited

OTHER PUBLICATIONS

Shapiro, Marvin B. et al., "RNA splice junctions of different classes of eukaryotes: sequence statistics and functioned implications in gene expression," Nucleic Acids Research, vol. 15(17):7155-7174 (1987).
Sherratt, Tim G. et al., "Exon Skipping and Translation in Patients with Frameshift Deletions in the Dystrophin Gene," Am. J. Hum. Genet., vol. 53:1007-1015 (1993).
Shiga, Nobuyuki et al., "Disruption of the Splicing Enhancer Sequence within Exon 27 of the Dystrophin Gene by a Nonsense Mutation induced Partial Skipping of the Exon and Is Responsible for Becker Muscular Dystrophy," J. Clin. Invest., vol. 100(9):2204-2210 (1997).
Shimizu, Miho et al., "Oligo(2'-O-methyl)ribonucleotides Effective probes for duplex DNA," FEBS Letters, vol. 302 (2):155-158 (1992) (Exhibit No. 1035 filed in interferences 106008, 106007 on Nov. 18, 2014).
*Siemens Healthcare Diagnostics, Inc. v. Enzo Life Sciences, Inc.*, 2013 WL 4411227, *11 [Parallel cite: U.S.D.C., D. Mass., Civil No. 10-40124-FDS], Decided Aug. 14, 2013 (12 pages); [Cited as: 2013 WL 4411227,], Exhibit No. 1210 filed in Interferences 106,007 and 106,008 on Feb. 17, 2015.
Sierakowska, Halina et al., "Repair of thalassemic human beta-globin mRNA in mammalian cells by antisense oligonucleotides," Proc. Natl. Acad. Sci. USA, vol. 93:12840-12344 (1996).
Sontheimer et al., "Metal ion catalysis during group II intron self-splicing: parallels with the spliceosome," Genes & Development, vol. 13, pp. 1729-1741 (1999), Exhibit No. 1195 filed in Interferences 106,007 and 106,008 on Feb. 17, 2015.
Sontheimer et al., "Three Novel Functional Variants of Human U5 Small Nuclear RNA," vol. 12, No. 2, pp. 734-746 (Feb. 1992), Exhibit No. 1194 filed in Interferences 106,007 and 106,008 on Feb. 17, 2015.
"Efficacy Study of AVI-4658 to induce Dystrophin Expression in Selected Duchenne Muscular Dystrophy Patients" ClinicalTrials. gov dated Jan. 22, 2013.
"Efficacy Study of AVI-4658 to Induce Dystrophin Expression in Selected Duchenne Muscular Dydtrophy Patients," Clinical Trial Identifier No. NCT01396239, ClinicalTrials.gov, dated Jul. 15, 2011, p. 1-4.
"Eteplirsen—Inhibitor of Dystrophin Expression—Treatment of Duchenne Muscular Dystrophy", Drugs of the Future, vol. 38(1):13-17 (2013).
2nd Expert Declaration of Dr. Erik Sontheimer ("2nd S Decl.") Exhibit No. 1067 filed in interferences 106008, 106007 on Dec. 23, 2014).
3rd Declaration of Erik J. Sontheimer, Ph.D. ("3rd S. Decl."), pp. 123, Exhibit No. 1186 filed in Interferences 106,007 and 106,008 on Feb. 17, 2015.
A Comparative Study on AONs between 20 and 50 Nucleotides Designed to Induce the Skipping of Exon 53 from the Dystrophin Pre-mRNA, pp. 6, Exhibit No. 1128 filed in Interferences 106,007 and 106,008 on Feb. 17, 2015.
A Comparative Study on AONs Between 20 and 50 Nucleotides Designed to Induce the Skipping of Exon 51 from the Dystrophin Pre-mRNA, pp. 6, Exhibit No. 1127 filed in Interferences 106,007 and 106,008 of Feb. 17, 2015.
Aartsma-Rus A, et al. "Theoretic applicability of antisense-mediated exon skipping for Duchenne muscular dystrophy mutations," Hum Mutat 2009;30:293-99.
Aartsma-Rus et al., "Antisense-induced exon skipping for duplications in Duchenne muscular dystrophy," BMC Medical Genetics 8:43 (2007), (University of Western Australia Exhibit 2135, filed Apr. 3, 2015 in Interferences 106007, 106008, and 106013, pp. 1-9.
Aartsma-Rus, Annemieke et al., "194th ENMC international workshop. 3rd ENMC workshop on exon skipping: Towards clinical application of antisense-mediated exon skipping for Duchenne muscular dystrophy Dec. 8-10, 2012, Naarden, The Netherlands," Neuromuscular Disorders, vol. 23:934-944 (2013).

Aartsma-Rus, Annemieke et al., "Antisense-Induced Multiexon Skipping for Duchenne Muscular Dystrophy Makes More Sense," Am. J. Hum. Genet., vol. 74:83-92 (2004).
Aartsma-Rus, Annemieke et al., "Functional Analysis of 114 Exon-Internal AONs for Targeted DMD Exon Skipping: Indication for Steric Hindrance of SR Protein Binding Sites," Oligonucleotides, vol. 15:284-297 (2005) (Exhibit No. 2016 filed in interferences 106008, 106013, 106007 on Nov. 18, 2014).
Aartsma-Rus, Annemieke et al., "Guidelines for Antisense Oligonucleotide Design and Insight Into Splice-modulating Mechanisms," Molecular Therapy, vol. 17(3):548-553 (2009) (Exhibit No. 2014 filed in interferences 106008, 106013, 106007 on Nov. 18, 2014).
Aartsma-Rus, Annemieke et al., "Targeted exon skipping as a potential gene correction therapy for Duchenne muscular dystrophy," Neuromuscular Disorders, vol. 12:S71-S77 (2002).
Aartsma-Rus, Annemieke et al., "Therapeutic antisense-induced exon skipping in cultured muscle cells from six different DMD patients," Human Molecular Genetics, vol. 12(8):907-914 (2003).
Abbs, Stephen et al., "A convenient multiplex PCR system for the detection of dystrophin gene deletions: a comparative analysis with cDNA hybridisation shows mistypings by both methods," J. Med. Genet., vol. 28:304-311 (1991).
Abes, S. et al., "Efficient Splicing Correction by PNA Conjugation to an R6-Penetratin Delivery Peptide", Nucleic Acids Research vol. 35(13):4495-4502 (2007).
Agrawal, Sudhir et al., "GEM 91—An Antisense Oligonucleotide Phosphorothioate as a Therapeutic Agent for AIDS," Antisense Research and Development, vol. 2:261-266 (1992).
Agrawal, Sudhir et al., "Oligodeoxynucleoside phosphoramidates and phosphorothioates as inhibitors of human immunodeficiency virus," Proc. Natl. Acad. Sci. USA, vol. 85:7079-7083 (1988).
Ahmad A, et al., "Mdx mice inducibly expressing dystrophin provide insights into the potential of gene therapy for Duchenne muscular dystrophy," Hum Mol Genet 2000;9:2507-2515.
Akhtar, Saghir et al., "Cellular uptake and intracellular fate of antisense oligonucleoticies" Trends in Cell Bioiogy, vol. 2:139-144 (1992).
Akhtar, Saghir, "Delivery Strategies for Antisense Oligonucleotide Therapeutics," CRC Press, Inc., Boca Raton, FL, 160 pages (1995).
Alignments of Dystrophin mRNA and Oligonucleotides, 6 pages, submitted to the Patent Trial and Appeal Board in interference No. 106008, dated Nov. 18, 2014 (Exhibit No. 1054 filed in interferences 106008, 106007 on Nov. 18, 2014).
Alter, Julia et al., "Systemic delivery of morpholino oligonucleotide restores dystrophin expression bodywide and improves dystrophic pathology," Nature Medicine, vol. 12(2):175-177 (2006).
Amendment under 37 CFR 1.312 for U.S. Appl. No. 14/248,279, 5 pages, dated Sep. 19, 2014 (Exhibit No. 2053 filed in interferences 106008, 106013, 106007 on Nov. 18, 2014).
Analysis of Second PCR Product by Gel Electrophoresis, pp. 1, Exhibit No. 1182 filed in Interferences 106,007 and 106,008 on Feb. 16, 2015.
Anderson, W. French, "Human Gene Therapy," Science, vol. 256:808-813 (1992).
Annotated scenario introduced and referred to during Mar. 12, 2015 deposition of Erik J. Sonthelmer, Ph.D., (University of Western Australia Exhibit 2139, flied Apr. 3, 2015 in Interferences 106007, 106008, and 106013, p. 1.).
Anthony, Karen et al., "Dystrophin quantification: Biological and Translational Research Implications," Neurology, vol. 83:1-8 (2014) (Exhibit No. 2028 filed in interferences 106008, 106013, 106007 on Nov. 18, 2014).
AON PS1958 Mass Spectrometry Data, pp. 7, Exhibit No. 1146 filed in Interferences 106,007 and 106,008 on Feb. 16, 2015.
AON PS1958 UPLC Data, pp. 2, Exhibit No. 1157 filed in Interferences 106,007 and 106,008 on Feb. 16, 2015.
AON PS1959 Mass Spectrometry Data, pp. 5, Exhibit No. 1147 filed in Interferences 106,007 and 106,008 on Feb. 16, 2015.
AON PS1959 UPLC Data, pp. 2, Exhibit No. 1158 filed in Interferences 106,007 and 106,008 on Feb. 16, 2015.
AON PS1960 Mass Spectrometry Data, pp. 8, Exhibit No. 1148 filed in Interferences 106,007 and 106,008 on Feb. 16, 2015.

(56) References Cited

OTHER PUBLICATIONS

AON PS1960 UPLC Data, pp. 2, Exhibit No. 1159 filed in Interferences 106,007 and 106,008 on Feb. 16, 2015.
AON PS1961 Mass Spectrometry Data, pp. 5, Exhibit No. 1149 filed in Interferences 106,001 and 106,008 on Feb. 16, 2015.
AON PS1961 UPLC Data, pp. 2, Exhibit No. 1160 filed in Interferences 106,007 and 106,008 on Feb. 16, 2015.
AON PS1962 Mass Spectrometry Data, pp. 7, Exhibit No. 1150 filed in Interferences 106,007 and 106,008 on Feb. 16, 2015.
AON PS1962 UPLC Data, pp. 2, Exhibit No. 1161 filed in Interferences 106,007 and 106,008 on Feb. 16, 2015.
AON PS1963 Mass Spectrometry Data, pp. 10, Exhibit No. 1151 filed in Interferences 106,007 and 106,008 on Feb. 16, 2015.
AON PS1963 UPLC Data, pp. 2, Exhibit No. 1162 filed in Interferences 106,007 and 106,008 on Feb. 16, 2015.
AON PS1964 Mass Spectrometry Data, pp. 13, Exhibit No. 1152 filed in Interferences 106,007 and 106,008 on Feb. 16, 2015.
AON PS1964 UPLC Data, pp. 2, Exhibit No. 1163 filed in Interferences 106,007 and 106,008 on Feb. 16, 2015.
AON PS1965 Mass Spectrometry Data, pp. 9, Exhibit No. 1153 filed in Interferences 106,007 and 106,008 on Feb. 16, 2015.
AON PS1965 UPLC Data, pp. 2, Exhibit No. 1164 filed in Interferences 106,007 and 106,008 on Feb. 16, 2015.
AON PS1966 Mass Spectrometry Data, pp. 8, Exhibit No. 1154 filed in Interferences 106,007 and 106,008 Feb. 16, 2015.
AON PS1966 UPLC Data, pp. 2, Exhibit No. 1165 filed in Interferences 106,007 and 106,008 on Feb. 16, 2015.
AON PS1967 Mass Spectrometry Data, pp. 7, Exhibit No. 1155 in Interferences 106,007 and 106,008 Feb. 16, 2015.
AON PS1967 UPLC Data, pp. 2, Exhibit No. 1166 filed in Interferences 106,007 and 106,008 on Feb. 16, 2015.
AON PS229 (h53AON1) HPLC Chromatograph pp. 2, Exhibit No. 1140 filed in Interferences 106,007 and 106,008 on Feb. 16, 2015.
Exon 53 Internal Sequence Schematic, pp. 1, Exhibit No. 1225 filed in Interferences 106,007 and 106,008 on Feb. 17, 2015.
Fairclough et al., "Therapy for Duchenne muscuiar dystrophy: renewed optimism from genetic approaches," Nature Reviews, pp. vol. 14, 373-378 (Jun. 2013), Exhibit No. 1112 filed in interferences 106,007 and 106,008 on Feb. 17, 2015.
Fall, Abbie M. et al., "Induction of revertant fibres in the mdx mouse using antisense oligonucleotides," Genetic Vaccines and Therapy, vol. 4:3, doi:10.1186/1479-0556-4-3, 12 pages (2006).
Federal Register, vol. 58, No. 183, pp. 49432-49434, Sep. 23, 1993 (6 pages); [Cited as: 58 FR 49132-01, 1993 WL 371451 (F.R.)], Exhibit No. 1221 filed in Interferences 106,007 and 106,008 on Feb. 17, 2015.
Federal Register, vol. 69, No. 155, pp. 49960-50020 dated Aug. 12, 2004 (62 pages), Exhibit No. 1220 filed in Interferences 106,007 and 106,008 on Feb. 17, 2015.
File Excerpt from AZL U.S. Appl. No. 11/233,495: Amendment After Non-Final Office Action, as-filed Nov. 1, 2010 (Exhibit No. 1085 filed in interferences 106008, 106007 on Dec. 23, 2014).
File Excerpt from AZL U.S. Appl. No. 11/233,495: Claims examined in Non-Final Office Action, dated Dec. 1, 2008 (Exhibit No. 1079 filed in interferences 106008, 106007 on Dec. 23, 2014).
File Excerpt from AZL U.S. Appl. No. 11/233,495: Final Office Action dated Aug. 31, 2010 (Exhibit No. 1086 filed in interferences 106008, 106007 on Dec. 23, 2014).
File Excerpt from U.S. Appl. No. 11/233,495: Non-Final Office Action dated Dec. 1, 2008 and Final Office Action dated Jun. 25, 2009 (Exhibit No. 1078 filed in interferences 106008, 106007 on Dec. 23, 2014).
File Excerpt from U.S. Appl. No. 12/198,007: AZL's Preliminary Amendment and Response, as-filed Nov. 7, 2008 (Exhibit No. 1075 filed in interferences 106008, 106007 on Dec. 23, 2014).
File Excerpt from U.S. Appl. No. 12/976,381: AZL's First Preliminary Amendment, as-filed Dec. 22, 2010 (Exhibit No. 1076 filed in interferences 106008, 106007 on Dec. 23, 2014).
File Excerpts from U.S. Appl. No. 11/233,495: Response to Non-Final Office Action, as filed Jul. 26, 2011 (14 pages), Exhibit No. 1222 filed in Interferences 106,007 and 106,008 on Feb. 17, 2015.
File Excerpts from U.S. Appl. No. 13/270,992 (UWA's U.S. Pat. No. 8,486,907): NFOA, dated Jul. 30, 2012; Applicant-Initiated Interview Summary, dated Nov. 8, 2012; Amendment, as filed Jan. 30, 2013; NOA, dated Apr. 4, 2013, Exhibit No. 1118 (122 pages) filed in interferences 106,007 and 106,008 of Feb. 17, 2015.
Flanagan, W. Michael, et al., "A cytosine analog that confers enhanced potency to antisense oligonucleotides," Proc. Nat'l Acad. Sci. USA, vol. 96, pp. 3513-3518 (Mar. 1999), Exhibit No. 1211 filed in Interferences 106,007 and 106,008 on Feb. 17, 2015.
Flanigan, Kevin M. et al., "Pharmacokinetics and safety of single doses of drisapersen in non-ambulant subjects with Duchenne muscular dystrophy: Results of a double-blind randomized clinical trial," Neuromuscular Disorders, vol. 24:16-24 (2014) (Exhibit No. 2038 filed in interferences 106008, 106013, 106007 on Nov. 18, 2014).
Flanigan, Kevin M., et al. (2003) "Rapid Direct Sequence Analysis of the Dystrophin Gene," Am. J. Hum. Genet. 72:931-939, dated Feb. 17, 2015 (Exhibit No. 2120 filed in interferences 106,007 and 106,008 on Feb. 17, 2015.
Fletcher S. et al, Morpholino oligomer-mediated exon skipping averts the onset of dystrophic pathology in the mdx mouse. Mol Ther 2007;15:1587-1592.
Fletcher, Sue et al., "Dystrophin Isoform Induction In Vivo by Antisense-mediated Alternative Splicing," Molecular Therapy, vol. 18(6):1218-1223 (2010).
Fletcher, Sue et al., "Targeted Exon Skipping to Address 'Leaky' Mutations in the Dystrophin Gene," Molecular Therapy-Nucleic Acids, vol. 1, e48, doi:10.1038/mtna.2012.40, 11 pages (2012).
Fletcher, Susan et al., "Dystrophin expression in the mdx mouse after localised and systemic administration of a morpholino antisense oligonucleotide," J. Gene Med., vol. 8:207-216 (2006).
Fletcher, Susan et al., "Gene therapy and molecular approaches to the treatment of hereditary muscular disorders," Curr. Opin. Neurol., vol. 13:553-560 (2000).
Foster, Helen et al., "Genetic Therapeutic Approaches for Duchenne Muscular Dystrophy," Human Gene Therapy, vol. 23:676-387 (2012).
Fourth Declaration of Erik Sontheimer, Ph.D. (Pursuant to Bd.R. 41.155(b)(2) and SO ¶¶ 155.1.3 and 155.1.4), dated Mar. 9, 2015, (University of Western Australia Exhibit 2138, filed Apr. 3, 2015 in Interferences 106007, 106008, and 106013, pp. 1-4).
Fragall, Clayton T. et al., "Mismatched single stranded antisense oligonucleotides can induce efficient dystrophin splice switching," BMC Medical Genetics, vol. 12:141, 8 pages (2011) (Exhibit No. 2019 filed in interferences 106008, 106013, 106007 on Nov. 18, 2014.
Fraley, Robert et al., "New generation liposomes: the engineering of an efficient vehicle for intracellular delivery of nucleic acids," Trends Biochem., vol. 6:77-80 (1981).
Frazier, Kendall S. et al., "Species-specific Inflammatory Responses as a Primary Component for the Development of Glomerular Lesions in Mice and Monkeys Following Chronic Administration of a Second-generation Antisense Oligonucleotide," Toxicologica Pathology, 13 pages (2013).
Friedmann, Theodore, "Progress Toward Human Gene Therapy," Science, vol. 244(4910):1275-1281 (1989).
Gebski, Bianca L. et al., "Morpholine antisense oligonucleotide induced dystrophin exon 23 skipping in mdx mouse muscle," Human Molecular Genetics, vol. 12(15):1801-1811 (2003).
Generic Method for Average Mass Determination Using LC-UV-MS in the Negative Mode, pp. 15, Exhibit No. 1145 filed in Interferences 106,007 and 106,008 on Feb. 16, 2015.
Generic UPLC Purity Method for Oligonucleotides 19- to 25-mers), pp. 18, Exhibit No. 1156 filed in Interferences 106,007 and 106,008 on Feb. 16, 2015.
Gennaro, Alfonso R., (ed.), Remington's Pharmaceutical Sciences, 18th Edition, Mack Publishing, Co., Easton PA, 2020 pages (1990).
Giles, Richard V. et al., "Antisense Morpholino Oligonucleotide Analog Induces Missplicing of C-myc mRNA," Antisense & Nucleic Acid Drug Development, vol. 9:213-220 (1999).

(56) References Cited

OTHER PUBLICATIONS

GlaxoSmithKline Press Release, Issued in London, UK, dated Jun. 27, 2013 (5 pages), Exhibit No. 1202 filed in Interferences 106,007 and 106,008 on Feb. 17, 2015.
GlaxoSmithKline, "GSK and Prosensa announce start of Phase III study of investigational Duchenne Muscular Dystrophy medication," press release, 6 pages, dated Jan. 19, 2011 (Exhibit No. 2060 filed in interferences 106008, 106013, 106007 on Nov. 18, 2014).
GlaxoSmithKline, Prosensa regains rights to drisapersen from GSK and retains rights to all other programmes for the treatment of Duchenne muscular dystrophy (DMD), press release, 4 pages, dated Jan. 13, 2014 (Exhibit 2040 in Interferences 106007, 106008, and 106013 on Nov. 18, 2014).
Goemans, Nathalie M. et al., "Systemic Administration of PRO051 in Duchenne's Muscular Dystrophy," The New England Journal of Medicine, vol. 364:1513-1522 (2011) (Exhibit No. 2036 filed in interferences 106008, 106013, 106007 on Nov. 18, 2014).
Gordon, Peter M. et al., "Metal ion catalysis during the exon-ligation step of nuclear pre-mRNA splicing: Extending the parallels between the spliceosome and group II introns," RNA, vol. 6:199-205 (2000) (Exhibit No. 1055 filed in interferences 106008, 106007 on Nov. 18, 2014).
Gordon, Peter M., et al., "Kinetic Characterization of the Second Step of Group II Intron Splicing: Role of Metal Ions and the Cleavage Site 2'-OH in Catalysis," Biochemistry, vol. 39, pp. 12939-12952 (2000), Exhibit No. 1188 filed in Interferences 106,007 and 106,008 on Feb. 17, 2015.
Goyenvalle, Aurelle et al., "Prevention of Dystrophic Pathology in Severely Affected Dystrophin/Utrophin-deficient Mice by Morpholino-oligomer-mediated Exon-skipping," Molecular Therapy, vol. 18(1):198-205 (2010).
Hammond, Suzan M. et al., "Correlating In Vitro Splice Switching Activity With Systemic In Vivo Delivery Using Novel ZEN-modified Oligonucleotides," Molecular Therapy—Nucleic Acids, vol. 3:1, 11 pages (2014) (Exhibit No. 2011 filed in interferences 106008, 106013, 106007 on Nov. 18, 2014).
Hammond, Suzan M., et al., "Genetic therapies for RNA mis-splicing diseases," Cell, vol. 27, No. 5, pp. 196-205 (May 2011), Exhibit No. 1113 filed in interferences 106,007 and 106,008 on Feb. 17, 2015.
Hammond, Suzan M., et al., "PRO-051, an antisense oligonucleotide for the potential treatment of Duchenne muscular dystrophy," Curr. Opinion Mol. Therap., vol. 12, No. 4, pp. 478-486 (2010), Exhibit No. 1121 filed in interferences 106,007 and 106,008 on Feb. 13, 2015.
Harding, PL et al., "The Influence of Antisense Oligonucleotide Length on Dystrophin Exon Skipping," Molecular Therapy, vol. 15(1):157-166 (2007) (Exhibit No. 1030 filed in interferences 106008, 106007 on Nov. 18, 2014).
Harel-Bellan, Annick et al., "Specific Inhibition of c-myc Protein Biosynthesis Using an Antisense Synthetic Deoxy-Oligonucleotide in Human T Lymphocytes." The Journal of Immunology, vol. 140(7):2431-2435 (1988).
Havenga, M.J.E., et al., "Exploiting the Natural Diversity in Adenovirus Tropism for Therapy and Prevention of Disease," J. Virol., vol. 76, No. 9, pp. 4612-4620 (May 2002), Exhibit No. 1123 filed in interferences 106,007 and 106,008 on Feb. 13, 2015.
Heasman, Janet, "Morpholino Oligos: Making Sense of Antisense?" Developmental Biology, vol. 243:209-214 (2002).
Heemskerk, Hans A. et al., "In vivo comparison of 2'-O-methyl phosphorothioate and morpholino antisense oligonucleotides for Duchenne muscular dystrophy exon skipping," The Journal of Gene Medicine, vol. 11:257-266 (2009) (Exhibit No. 2020 filed in interferences 106008, 106013, 106007 on Nov. 18, 2014).
Heid, Christian A. et al., "Real Time Quantitative PCR," Genome Research, vol. 6:986-994 (1996) (Exhibit No. 1061 filed in interferences 106008, 106007 on Nov. 18, 2014).
Herschlag, Daniel et al., "Contributions of 2' Hydroxyl Groups of the RNA Substrate to Binding and Catalysis by the Tetrahymena Ribozyme: An Energetic Picture of an Active Site Composed of RNA," Biochemistry, vol. 32:8299-8311 (1993) (Exhibit No. 1031 filed in interferences 106008, 106007 on Nov. 18, 2014).
Hoffman EP, et al., "Characterization of dystrophin in muscle-biopsy specimens from patients with Duchenne's or Becker's muscular dystrophy" N Engl J Med 1988;318-1363-68.
"Efficacy, Safety, and Tolerability Rollover Study of Eteplirsen in Subjects with Duchenne Muscular Dystrophy," Clinical Trial Identifier No. NCT01540409, ClinicalTrials.gov, published online Feb. 23, 2012, p. 1-4.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Jul. 31, 2012, 3 pages.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Oct. 17, 2013, 3 pages.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Feb. 27, 2012, 3 pages.
Errata to the Sarepla Briefing Information for the Apr. 25, 2016 Meeting of the Peripheral and Central Nervous System Drugs Advisory Committee, Eteplirsen Errata Document, NDA 206488, 5 pages.
Extended European Search Report, EP 15190341.6, dated Apr. 28, 2016, 9 pages.
FDA Briefing Document, "Peripheral and Central Nervous System," Drugs Advisory Committee Meeting, NDA 206488 Eteplirsen, Food and Drug Administration, pp. 1-73, Jan. 22, 2016.
FDA Briefing Information for the Apr. 25, 2016 Meeting of the Peripheral and Central Nervous System Drugs Advisory Committee, Eteplirsen, NDA 206488, 115 pages.
Jett Foundation Presentation by McSherry, C. "Patient and Caregiver-Reported Outcomes of Patients in Clinical Trials of Eteplirsen for Treatment of Duchenne" at Peripheral and Central Nervous System Drugs Advisory Committee, Apr. 25, 2016, 17 pages.
Letter to the U.S. Food and Drug Administration, (Dr. Billy Dunn, M.D. Director Division of Neurology Products, Office of Drug Evaluation 1, Center for Drug Evaluation and Research), for The Peripheral and Central Nervous System Advisory Committee Meeting (AdComm) supporting approval of eteplirsen, dated Feb. 24, 2016, 4 pages.
Letter to the U.S. Food and Drug Administration. (Dr. Janet Woodcock, M.D. Director, CDER), from The Congress of The United States regarding Duchenne muscular dystrophy, dated Feb. 17, 2016, 7 pages.
Popplewell, et al., Design of Phosphorodiamidate Morpholine Oligomers (PMOs) for the Induction of Exon Skipping of the Human DMD Gene, DSGT Poster, 2008, 1 page.
Sarepta Briefing Information for the Apr. 25, 2016 Meeting of the Peripheral and Central Nervous System Drugs Advisory Committee, Eteplirsen Briefing Document, NDA 206488, 186 pages.
Sarepta Presentation at Peripheral and Central Nervous System Drugs Advisory Committee, Apr. 25, 2016, 133 pages.
Sarepta Press Release, Sarepta Issues Statement on Advisory Committee Outcome for Use of Eteplirsen in the Treatment of Duchenne Muscular Dystrophy, Apr. 25, 2016, 2 pages.
Sarepta Therapeutics, Advisory Committee Briefing Materials: Available for Public Release, "Peripheral and Central Nervous System Drugs Advisory Committee," Eteplirsen Briefing Document Addendum, NDA 206488, pp. 1-9, dated Jan. 22, 2016.
Sarepta Therapeutics, Advisory Committee Briefing Materials: Available for Public Release, "Peripheral and Central Nervous System Drugs Advisory Committee," Eteplirsen Briefing Document, NDA 206488, pp. 1-166, dated Jan. 22, 2016.
U.S. Food and Drug Administration Presentation at Peripheral and Central Nervous System Drugs Advisory Committee, Apr. 25, 2016, 178 pages.
*University of Western Australia* v. *Academisch Ziekenhuis Leiden*, Decision—Motions—37 CFR § 41.125(a) (Substitute), filed in Patent Interference No. 106007, May 12, 2016, pp. 1-53 (Doc 476).

(56) References Cited

OTHER PUBLICATIONS

*University of Western Australia v. Academisch Ziekenhuis Leiden*, Judgment—Motions—37 CFR § 41.127, filed in Patent Interference No. 106007, Apr. 29, 2016, pp. 1-3, (Doc 474).
*University of Western Australia v. Academisch Ziekenhuis Leiden*, Redeclaration—37 CFR 41.203(c), filed in Patent Interference No. 106007, Apr. 29, 2016, pp. 1-2, (Doc 473).
*University of Western Australia v. Academisch Ziekenhuis Leiden*, Withdrawal and Reissue of Decision on Motions, filed in Patent Interference No. 106007, May 12, 2016, pp. 1-2 (Doc 475).
*University of Western Australia v. Academisch Ziekenhuis Leiden*, Decision—Motions—37 CFR § 41.125(a), filed in Patent Interference No. 106007, Apr. 29, 2016. pp. 1-53. (Doc 472).
*University of Western Australia v. Academisch Ziekenhuis Leiden*, Decision-Rehearing—37 CFR § 41.125(c), filed in Patent Interference No. 106,013, Dec. 29, 2015, pp. 1-12 (Doc 202).
AVI BioPharma, The Lancet Publishes Clinical Trial Data That Demonstrate Statistically Significant and Dose-Dependent Expression of Dystrophin in Duchenne Muscular Dystrophy Patients With AVI BioPharma's Eteplirsen, Press Release, Jul. 25, 2011, pp. 1-2.
Extended European Search Report, EP 16172354.9, dated Jan. 23, 2017, 7 pages.
Extended European Search Report, EP 17159328.8, dated Sep. 5, 2017, 10 pages.
FDA News Release, "FDA grants accelerated approval to first drug for Duchenne muscular dystrophy," Sep. 19, 2016, 3 pages.
Feener, C. et al., "Alternative splicing or human dystrophin mRNA generates isoforms at the carboxy terminus," Nature, vol. 338:509-511 (1989).
GenBank AF213437.1 Dated Jan. 17, 2002.
International Search Report and Written Opinion, PCT/US2016/054534, dated Jan. 17, 2017, 13 pages.
Kole et al. "Exon skipping therapy for Duchenne muscular dystrophy," Advanced Drug Delivery Reviews, vol. 87:104-107 (2015).
Letter from the FDA to Sarepta Therapeutics, Inc., Re: Accelerated Approval for the use of Exondys 51 (eteplirsen), FDA Reference ID: 3987286, dated Sep. 19, 2016, 11 pages.
Prescribing Information for EXONDYS 51 (eteplirsen) Injection, dated Sep. 2016, 10 pages.
Sarepta Therapeutics, Inc. News Release, "Sarepta Therapeutics Announces FDA Accelerated Approval of EXONDYS 51™ (eteplirsen) injection, an Exon Skipping Therapy to Treat Duchenne Muscular Dystrophy (DMD) Patients Amenable to Skipping Exon 51," Sep. 19, 2016, 2 pages.
*University of Western Australia v. Academisch Ziekenhuis Leiden*, Decision—Motions—37 C.F.R. § 41.125(a), filed in Patent Interference No. 106008, Sep. 20, 2016, pp. 1-20 (Doc 480).
*University of Western Australia v. Academisch Ziekenhuis Leiden*, Judgment—Motions—37 C.F.R. § 41.127 filed in Patent Interference No. 106008, Sep. 20, 2016, pp. 1-3 (Doc 481).
WHO Drug Information, International Nonproprietary Names for Pharmaceutical Substances (INN), Proposed INN: List 115, "CASIMERSEN," vol. 30(2): 3 pages (2016).
WHO Drug Information, International Nonproprietary Names for Pharmaceutical Substances (INN), Proposed INN: List 115, "Golodirsen," vol. 30(2): 3 pages (2016).
Office Action dated Apr. 1, 2015, in U.S. Appl. No. 14/213,607, Bestwick et al., filed Mar. 14, 2014, 12 pages.
Office Action dated Jun. 18, 2018, in U.S. Appl. No. 15/431,468, Bestwick et al., filed Feb. 13, 2017, 12 pages.
Aartsma-Rus, Annemieke et al., "Guidelines for Antisense Oligonucleotide Design and Insight Into Splice-modulating Mechanisms," Molecular Therapy, Vo. 17(3):548-553 (2009). Supplementary Table 1.
Office Action dated Jun. 8, 2018, in U.S. Appl. No. 15/422,127, Bestwick et al., filed Feb. 1, 2017, 14 pages.
Office Action dated Nov. 27, 2017, in U.S. Appl. No. 15/422,127, Bestwick et al., filed Feb. 1, 2017, 14 pages.
Co-Pending U.S. Appl. No. 16/213,428, inventor Bestwick, Richard K., filed Dec. 7, 2018.
Office Action dated Aug. 15, 2019, in U.S. Appl. No. 16/213,428, Bestwick et al., filed Dec. 7, 2018, 7 pages.

SEQUENCE LISTING

<160> NUMBER OF SEQ ID NOS: 42

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
cagatctgtc aaatcgcctg cagg                                          24

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 2
caacagatct gtcaaatcgc ctgcagg                                       27

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 3
ctcaacagat ctgtcaaatc gcctgcagg                                     29

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
gtgtctttct gagaaactgt tcagc                                         25

<210> SEQ ID NO 5
<211> LENGTH: 28
<212> TYPE: DNA
<213> ORGANISM: Artificial Sequence
<220> FEATURE:

<223> OTHER INFORMATION: Synthetic oligonucleotide

<400> SEQUENCE: 5
gagaaactgt tcagcttctg ttagccac                                              28

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 6
gaaactgttc agcttctgtt agccactg                                              28

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
ctgttcagct tctgttagcc actg                                                  24

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
atctgtcaaa tcgcctgcag                                                       20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
tttgtgtctt tctgagaaac                                                       20

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
tgttcagctt ctgttagcca ctga                                                  24

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
gatctgtcaa atcgcctgca ggtaa                                                 25

```
<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
aaactgttca gcttctgtta gccac                                         25

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
ttgtgtcttt ctgagaaact gttca                                         25

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 14
caacagatct gtcaaatcgc ctgcag                                        26

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 15
cagatctgtc aaatcgcctg caggta                                        26

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 16
ctgttcagct tctgttagcc actgatt                                       27

<210> SEQ ID NO 17
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 17
gaaactgttc agcttctgtt agccactgat t                                  31

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide
```

<400> SEQUENCE: 18
agaaactgtt cagcttctgt tagcca                                              26

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Arg Arg Arg Gln Arg Arg Lys Lys Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Arg Lys Lys Arg Arg Gln Arg Arg Arg
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Arg Arg Arg Arg Arg Arg Arg Arg Arg Phe Phe
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Arg Arg Arg Arg Arg Phe Phe Arg Arg Arg Arg
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Synthetic peptide

<400> SEQUENCE: 23

Arg Arg Arg Arg
1

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Arg Arg Arg Arg Arg
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Arg Arg Arg Arg Arg Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Arg Arg Arg Arg Arg Arg Arg
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Arg Arg Arg Arg Arg Arg Arg Arg
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Arg Arg Arg Arg Arg Arg Arg Arg Arg
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:

```
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 29

Arg Xaa Arg Xaa Arg Xaa Arg Xaa Arg Xaa Arg Xaa Arg Xaa Arg Xaa
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is 6-aminohexanoic acid
<220> FEATURE:
<221> NAME/KEY: misc_feature
<222> LOCATION: (8)..(8)
<223> OTHER INFORMATION: Xaa is 6-aminohexanoic acid
<220> FEATURE:
<221> NAME/KEY: misc_feature
<222> LOCATION: (11)..(11)
<223> OTHER INFORMATION: Xaa is 6-aminohexanoic acid

<400> SEQUENCE: 30

Arg Xaa Arg Arg Xaa Arg Arg Xaa Arg Arg Xaa Arg
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is 6-aminohexanoic acid
<220> FEATURE:
<221> NAME/KEY: misc_feature
<222> LOCATION: (8)..(8)
<223> OTHER INFORMATION: Xaa is 6-aminohexanoic acid
<220> FEATURE:
<221> NAME/KEY: misc_feature
<222> LOCATION: (11)..(11)
<223> OTHER INFORMATION: Xaa is 6-aminohexanoic acid
<220> FEATURE:
<221> NAME/KEY: misc_feature
<222> LOCATION: (14)..(14)
<223> OTHER INFORMATION: Xaa is 6-aminohexanoic acid

<400> SEQUENCE: 31
```

Arg Xaa Arg Arg Xaa Arg Arg Xaa Arg Arg Xaa Arg Arg Xaa Arg
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is beta-alanine
<220> FEATURE:
<221> NAME/KEY: misc_feature
<222> LOCATION: (8)..(8)
<223> OTHER INFORMATION: Xaa is 6-aminohexanoic acid
<220> FEATURE:
<221> NAME/KEY: misc_feature
<222> LOCATION: (11)..(11)
<223> OTHER INFORMATION: Xaa is beta-alanine

<400> SEQUENCE: 32

Arg Xaa Arg Arg Xaa Arg Arg Xaa Arg Arg Xaa Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

Arg Ala Arg Arg Ala Arg Arg Ala Arg Arg Ala Arg Phe Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic peptide

<400> SEQUENCE: 34

Arg Gly Arg Arg Gly Arg Arg Gly Arg Arg Gly Arg Phe Phe
1               5                   10

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 35
cttggacaga acttaccgac tgg                                           23

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 36
gtttcttcca aagcagcctc tcg                                          23

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
gcaggatttg aacagaggc g                                             21

<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 38
catctacatt tgtctgccac tgg                                          23

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
caatgctcct gacctctgtg c                                            21

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 40 gctctttcc aggttcaagt gg                                            22

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
gtctacaaca aagctcaggt cg                                           22

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
gcaatgttat ctgcttcctc caacc                                        25
```

EXON SKIPPING COMPOSITIONS FOR TREATING MUSCULAR DYSTROPHY

RELATED APPLICATIONS

This application is a continuation of U.S. patent application Ser. No. 15/431,468, filed Feb. 13, 2017, which is a continuation of U.S. patent application Ser. No. 14/942,629, filed Nov. 16, 2015, now abandoned, which is a continuation of U.S. patent application Ser. No. 14/213,607, filed on Mar. 14, 2014, now issued as U.S. Pat. No. 9,217,148, which claims the benefit of U.S. Provisional Patent Application No. 61/784,547, filed on Mar. 14, 2013. The entire contents of each of the foregoing applications are incorporated herein by reference in their entireties.

FIELD OF THE INVENTION

The present invention relates to novel antisense compounds and compositions suitable for facilitating exon skipping in the human dystrophin gene. It also provides methods for inducing exon skipping using the novel antisense compositions adapted for use in the methods of the invention.

STATEMENT REGARDING SEQUENCE LISTING

The instant application contains a Sequence Listing which has been submitted electronically in ASCII format and is hereby incorporated by reference in its entirety. Said ASCII copy, created on Dec. 13, 2018, is named 4140_004007_SL.txt and is 10,678 bytes in size. The Sequence Listing is being submitted by EFS Web and is hereby incorporated by reference into the specification.

BACKGROUND OF THE INVENTION

Antisense technologies are being developed using a range of chemistries to affect gene expression at a variety of different levels (transcription, splicing, stability, translation). Much of that research has focused on the use of antisense compounds to correct or compensate for abnormal or disease-associated genes in a wide range of indications. Antisense molecules are able to inhibit gene expression with specificity, and because of this, many research efforts concerning oligonucleotides as modulators of gene expression have focused on inhibiting the expression of targeted genes or the function of cis-acting elements. The antisense oligonucleotides are typically directed against RNA, either the sense strand (e.g., mRNA), or minus-strand in the case of some viral RNA targets. To achieve a desired effect of specific gene down-regulation, the oligonucleotides generally promote the decay of the targeted mRNA, block translation of the mRNA or block the function of cis-acting RNA elements, thereby effectively preventing either de novo synthesis of the target protein or replication of the viral RNA.

However, such techniques are not useful where the object is to up-regulate production of the native protein or compensate for mutations that induce premature termination of translation, such as nonsense or frame-shifting mutations. In these cases, the defective gene transcript should not be subjected to targeted degradation or steric inhibition, so the antisense oligonucleotide chemistry should not promote target mRNA decay or block translation.

In a variety of genetic diseases, the effects of mutations on the eventual expression of a gene can be modulated through a process of targeted exon skipping during the splicing process. The splicing process is directed by complex multi-component machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short, semi-conserved RNA segments to which various nuclear splicing factors that are then involved in the splicing reactions bind. By changing the way the splicing machinery reads or recognizes the motifs involved in pre-mRNA processing, it is possible to create differentially spliced mRNA molecules. It has now been recognized that the majority of human genes are alternatively spliced during normal gene expression, although the mechanisms involved have not been identified. Bennett et al. (U.S. Pat. No. 6,210,892) describe antisense modulation of wild-type cellular mRNA processing using antisense oligonucleotide analogs that do not induce RNAse H-mediated cleavage of the target RNA. This finds utility in being able to generate alternatively spliced mRNAs that lack specific exons (e.g., as described by (Sazani, Kole, et al. 2007) for the generation of soluble TNF superfamily receptors that lack exons encoding membrane spanning domains.

In cases where a normally functional protein is prematurely terminated because of mutations therein, a means for restoring some functional protein production through antisense technology has been shown to be possible through intervention during the splicing processes, and that if exons associated with disease-causing mutations can be specifically deleted from some genes, a shortened protein product can sometimes be produced that has similar biological properties of the native protein or has sufficient biological activity to ameliorate the disease caused by mutations associated with the exon (see e.g., Sierakowska, Sambade et al. 1996; Wilton, Lloyd et al. 1999; van Deutekom, Bremmer-Bout et al. 2001; Lu, Mann et al. 2003; Aartsma-Rus, Janson et al. 2004). Kole et al. (U.S. Pat. Nos. 5,627,274; 5,916,808; 5,976,879; and 5,665,593) disclose methods of combating aberrant splicing using modified antisense oligonucleotide analogs that do not promote decay of the targeted pre-mRNA. Bennett et al. (U.S. Pat. No. 6,210,892) describe antisense modulation of wild-type cellular mRNA processing also using antisense oligonucleotide analogs that do not induce RNAse H-mediated cleavage of the target RNA.

The process of targeted exon skipping is likely to be particularly useful in long genes where there are many exons and introns, where there is redundancy in the genetic constitution of the exons or where a protein is able to function without one or more particular exons. Efforts to redirect gene processing for the treatment of genetic diseases associated with truncations caused by mutations in various genes have focused on the use of antisense oligonucleotides that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD.

A less severe form of muscular dystrophy, Becker muscular dystrophy (BMD) has been found to arise where a mutation, typically a deletion of one or more exons, results in a correct reading frame along the entire dystrophin transcript, such that translation of mRNA into protein is not prematurely terminated. If the joining of the upstream and downstream exons in the processing of a mutated dystrophin pre-mRNA maintains the correct reading frame of the gene, the result is an mRNA coding for a protein with a short internal deletion that retains some activity, resulting in a Becker phenotype.

For many years it has been known that deletions of an exon or exons which do not alter the reading frame of a dystrophin protein would give rise to a BMD phenotype, whereas an exon deletion that causes a frame-shift will give rise to DMD (Monaco, Bertelson et al. 1988). In general, dystrophin mutations including point mutations and exon deletions that change the reading frame and thus interrupt proper protein translation result in DMD. It should also be noted that some BMD and DMD patients have exon deletions covering multiple exons.

Modulation of mutant dystrophin pre-mRNA splicing with antisense oligoribonucleotides has been reported both in vitro and in vivo (see e.g., Matsuo, Masumura et al. 1991; Takeshima, Nishio et al. 1995; Pramono, Takeshima et al. 1996; Dunckley, Eperon et al. 1997; Dunckley, Manoharan et al. 1998; Errington, Mann et al. 2003).

The first example of specific and reproducible exon skipping in the mdr mouse model was reported by Wilton et al. (Wilton, Lloyd et al. 1999). By directing an antisense molecule to the donor splice site, consistent and efficient exon 23 skipping was induced in the dystrophin mRNA within 6 hours of treatment of the cultured cells. Wilton et al. also describe targeting the acceptor region of the mouse dystrophin pre-mRNA with longer antisense oligonucleotides. While the first antisense oligonucleotide directed at the intron 23 donor splice site induced consistent exon skipping in primary cultured myoblasts, this compound was found to be much less efficient in immortalized cell cultures expressing higher levels of dystrophin. However, with refined targeting and antisense oligonucleotide design, the efficiency of specific exon removal was increased by almost an order of magnitude (Mann, Honeyman et al. 2002).

Recent studies have begun to address the challenge of achieving sustained dystrophin expression accompanied by minimal adverse effects in tissues affected by the absence of dystrophin. Intramuscular injection of an antisense oligonucleotide targeted to exon 51 (PRO051) into the tibialis anterior muscle in four patients with DMD resulted in specific skipping of exon 51 without any clinically apparent adverse effects (Mann, Honeyman et al. 2002; van Deutekom, Janson et al. 2007). Studies looking at systemic delivery of an antisense phosphorodiamidate morpholino oligomer conjugated to a cell-penetrating peptide (PPMO) targeted to exon 23 in mdx mice produced high and sustained dystrophin protein production in skeletal and cardiac muscles without detectable toxicity (Jearawiriyapaisarn, Moulton et al. 2008; Wu, Moulton et al. 2008; Yin, Moulton et al. 2008).

Recent clinical trials testing the safety and efficacy of splice switching oligonucleotides (SSOs) for the treatment of DMD are based on SSO technology to induce alternative splicing of pre-mRNAs by steric blockade of the spliceosome (Cirak et al., 2011; Goemans et al., 2011; Kinali et al., 2009; van Deutekom et al., 2007).

Despite these successes, there remains a need for improved antisense oligomers targeted to multiple dystrophin exons and improved delivery compositions and methods for DMD therapeutic applications.

SUMMARY OF THE INVENTION

According to one aspect, the invention provides antisense molecules capable of binding to a selected target in human dystrophin pre-mRNA to induce exon skipping. In another aspect, the invention provides two or more antisense oligonucleotides which are used together to induce single or multiple exon skipping. For example, exon skipping of a single or multiple exons can be achieved by linking together two or more antisense oligonucleotide molecules.

In another aspect, the invention relates to an isolated antisense oligonucleotide of 20 to 50 nucleotides in length, including at least 10, 12, 15, 17 or 20 consecutive nucleotides complementary to an exon 44 target region of the dystrophin gene designated as an annealing site selected from the group consisting of: H44A(−07+17) and H44A(+62+89), wherein the antisense oligonucleotide specifically hybridizes to the annealing site inducing exon 44 skipping. In one embodiment, the antisense oligonucleotide is 20 to 30 or 24 to 28 nucleotides in length. Another embodiment of the invention relates to an isolated antisense oligonucleotide of 20 to 50 nucleotides in length, including at least 10, 12, 15, 17 or 20 consecutive nucleotides complementary to an exon 44 target region of the dystrophin gene designated as an annealing site selected from the group consisting of: H44A (−07+17) and H44A(+62+89), wherein the antisense oligonucleotide specifically hybridizes to the annealing site inducing exon 44 skipping. In yet another embodiment, the invention relates to an isolated antisense oligonucleotide of 20 to 50 nucleotides in length, including at least 10, 12, 15, 17 or 20 consecutive nucleotides complementary to an exon 44 target region of the dystrophin gene designated as an annealing site selected from the group consisting of: H44A (−07+17) and H44A(+62+89), wherein the antisense oligonucleotide specifically hybridizes to the annealing site inducing exon 53 skipping. In one embodiment, the antisense oligonucleotide is 20 to 30 or 24 to 28 nucleotides in length.

In another aspect, the invention relates to an isolated antisense oligonucleotide of 20 to 50 nucleotides in length, including at least 10, 12, 15, 17, or 20 consecutive nucleotides of a nucleotide sequence selected from the group consisting of: SEQ ID NOs: 1 and 6, wherein the oligonucleotide specifically hybridizes to an exon 44 target region of the human dystrophin gene and induces exon 44 skipping. In one embodiment, the antisense oligonucleotide is 20 to 30 or 24 to 28 nucleotides in length. In another embodiment, thymine bases in SEQ ID NOs: 1 and 6 are optionally uracil.

Other embodiments of the invention relate to an isolated antisense oligonucleotide of 20 to 50 nucleotides in length, including at least 10, 12, 15, 17, or 20 consecutive nucleotides of a nucleotide sequence selected from the group consisting of: SEQ ID NOs: 2, 3, 4, 5 and 7, wherein the oligonucleotide specifically hybridizes to an exon 44 target region of the Dystrophin gene and induces exon 44 skipping. In one embodiment, the antisense oligonucleotide is 20 to 30 or 24 to 29 nucleotides in length. In another embodiment, thymine bases in SEQ ID NOs: 2, 3, 4, 5 and 7 are optionally uracil.

The present invention includes exemplary antisense sequences targeted to exon 44, such as those identified below.

```
H44A(-07+17):
                                             (SEQ ID NO: 1)
5'-CAGATCTGTCAAATCGCCTGCAGG-3'

H44A(-07+20):
                                             (SEQ ID NO: 2)
5'-CAACAGATCTGTCAAATCGCCTGCAGG-3'

H44A(-07+22):
                                             (SEQ ID NO: 3)
5'-CTCAACAGATCTGTCAAATCGCCTGCAGG-3'

H44A(+77+101):
                                             (SEQ ID NO: 4)
5'-GTGTCTTTCTGAGAAACTGTTCAGC-3'

H44A(+64+91):
                                             (SEQ ID NO: 5)
5'-GAGAAACTGTTCAGCTTCTGTTAGCCAC-3'

H44A(+62+89):
                                             (SEQ ID NO: 6)
5'-GAAACTGTTCAGCTTCTGTTAGCCACTG-3'

H44A(+62+85)):
                                             (SEQ ID NO: 7)
5'-CTGTTCAGCTTCTGTTAGCCACTG-3'
```

In one embodiment, the antisense oligomer specifically hybridizes to annealing site H44A(−07+17), such as SEQ ID NO: 1. In another embodiment, the antisense oligomer specifically hybridizes to annealing site H44A(+62+89), such as SEQ ID NO: 6.

In another aspect, the invention includes an antisense oligonucleotide compound that is: (i) composed of morpholino subunits and phosphorus-containing intersubunit linkages joining a morpholino nitrogen of one subunit to a 5' exocyclic carbon of an adjacent subunit, (ii) containing between 10-50, 15-50, 20-50, 20-30, or 25-35 nucleotide bases, (iii) having a base sequence effective to hybridize to at least 10, 12, 15, 17, or 20 consecutive bases of a target sequence in dystrophin pre-mRNA and induce exon skipping.

In one aspect, the antisense compound is composed of phosphorus-containing intersubunit linkages joining a morpholino nitrogen of one subunit to a 5' exocyclic carbon of an adjacent subunit. The morpholino subunits in the compound may be joined by phosphorodiamidate linkages, in accordance with the structure:

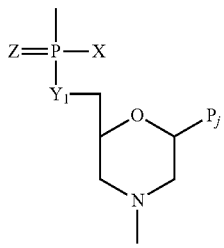

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino e.g., wherein X=$NR_2$, where each R is independently hydrogen or methyl. The above intersubunit linkages, which are uncharged, may be interspersed with linkages that are positively charged at physiological pH, where the total number of positively charged linkages is between 1 and up to all of the total number of intersubunit linkages.

In another exemplary embodiment, the compound is comprised of intersubunit linkage and terminal modifications as described in U.S. application Ser. No. 13/118,298, which is incorporated herein in its entirety.

In some embodiments, the antisense oligomers of the invention do not activate RNase H. In some embodiments, the antisense oligonucleotides comprise a non-natural backbone. In some embodiments, the sugar moieties of the oligonucleotide backbone are replaced with non-natural moieties, such as morpholinos. In some embodiments, the antisense oligonucleotides have the inter-nucleotide linkages of the oligonucleotide backbone replaced with non-natural inter-nucleotide linkages, such as modified phosphates. Exemplary modified phosphates include methyl phosphonates, methyl phosphorothioates, phosphoromorpholidates, phosophropiperazidates, and phosphoroamidates. In some embodiments, the antisense oligonucleotide is a 2'-O-methyl-oligoribonucleotide or a peptide nucleic acid.

In some embodiments, the antisense oligonucleotide is chemically linked to one or more moieties, such as a polyethylene glycol moiety, or conjugates, such as a arginine-rich cell penetrating peptide (e.g., SEQ ID NOs: 19-34), that enhance the activity, cellular distribution, or cellular uptake of the antisense oligonucleotide. In one exemplary embodiment, the arginine-rich polypeptide is covalently coupled at its N-terminal or C-terminal residue to the 3' or 5' end of the antisense compound. Also in an exemplary embodiment, the antisense compound is composed of morpholino subunits and phosphorus-containing intersubunit linkages joining a morpholino nitrogen of one subunit to a 5' exocyclic carbon of an adjacent subunit.

In another aspect, the invention provides expression vectors that incorporate the antisense oligonucleotides described above, e.g., the antisense oligonucleotides of SEQ ID NOs: 1-7. In some embodiments, the expression vector is a modified retrovirus or non-retroviral vector, such as a adeno-associated viral vector.

In another aspect, the invention provides pharmaceutical compositions that include the antisense oligonucleotides described above, and a saline solution that includes a phosphate buffer.

In another aspect, the invention provides antisense molecules selected and or adapted to aid in the prophylactic or therapeutic treatment of a genetic disorder comprising at least an antisense molecule in a form suitable for delivery to a patient.

In another aspect, the invention provides a method for treating a patient suffering from a genetic disease wherein there is a mutation in a gene encoding a particular protein and the affect of the mutation can be abrogated by exon skipping, comprising the steps of: (a) selecting an antisense molecule in accordance with the methods described herein; and (b) administering the molecule to a patient in need of such treatment. The invention also addresses the use of purified and isolated antisense oligonucleotides of the invention, for the manufacture of a medicament for treatment of a genetic disease.

In another aspect, the invention provides a method of treating a condition characterized by muscular dystrophy, such as Duchenne muscular dystrophy or Becker muscular dystrophy, which includes administering to a patient an effective amount of an appropriately designed antisense oligonucleotide of the invention, relevant to the particular genetic lesion in that patient. Further, the invention provides a method for prophylactically treating a patient to prevent or minimize muscular dystrophy, such as Duchenne muscular dystrophy or Becker muscular dystrophy, by administering to the patient an effective amount of an antisense oligonucleotide or a pharmaceutical composition comprising one or more of these biological molecules.

In another aspect, the invention also provides kits for treating a genetic disease, which kits comprise at least an antisense oligonucleotide of the present invention, packaged in a suitable container and instructions for its use.

These and other objects and features will be more fully understood when the following detailed description of the invention is read in conjunction with the figures.

BRIEF DESCRIPTION OF THE FIGURES

In FIG. 3, H44A(−06+14), H44A(−06+20) and H44A(−09+17) (SEQ ID NOs: 8, 14 and 15, respectively) are published oligomers. In FIG. 4, H44A(+85+104), H44A(+59+85) and H44A(+65+90) (SEQ ID NOs: 9, 16 and 18, respectively) are published oligomers.

DETAILED DESCRIPTION OF THE INVENTION

Figure 1A:
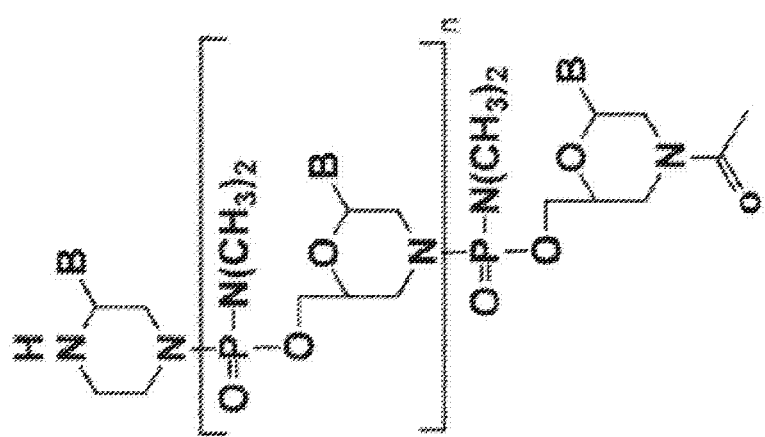
FIG. 1A shows an exemplary morpholino oligomer structure with a phosphorodiamidate linkage.

Embodiments of the present invention relate generally to improved antisense compounds, and methods of use thereof, which are specifically designed to induce exon skipping in the human dystrophin gene. Dystrophin plays a vital role in muscle function, and various muscle-related diseases are characterized by mutated forms of this gene. Hence, in certain embodiments, the improved antisense compounds described herein induce exon skipping in mutated forms of the human dystrophin gene, such as the mutated dystrophin genes found in Duchenne muscular dystrophy (DMD) and Becker muscular dystrophy (BMD).

Due to aberrant mRNA splicing events caused by mutations, these mutated human dystrophin genes either express defective dystrophin protein or express no measurable dystrophin at all, a condition that leads to various forms of muscular dystrophy. To remedy this condition, the antisense compounds of the present invention hybridize to selected regions of a pre-processed RNA of a mutated human dystrophin gene, induce exon skipping and differential splicing in that otherwise aberrantly spliced dystrophin mRNA, and thereby allow muscle cells to produce an mRNA transcript that encodes a functional dystrophin protein. In certain embodiments, the resulting dystrophin protein is not necessarily the "wild-type" form of dystrophin, but is rather a truncated, yet functional or semi-functional, form of dystrophin.

By increasing the levels of functional dystrophin protein in muscle cells, these and related embodiments are useful in the prophylaxis and treatment of muscular dystrophy, especially those forms of muscular dystrophy, such as DMD and BMD, that are characterized by the expression of defective dystrophin proteins due to aberrant mRNA splicing. The specific oligomers described herein further provide improved, dystrophin-exon-specific targeting over other oligomers in use, and thereby offer significant and practical advantages over alternate methods of treating relevant forms of muscular dystrophy.

Thus, the invention relates to isolated antisense oligonucleotides of 20 to 50 nucleotides in length, including at least 10, 12, 15, 17, 20 or more, consecutive nucleotides complementary to an exon 44 target region of the dystrophin gene designated as an annealing site selected from the group consisting of: H44A(−07+17) and H44A(+62+89). Antisense oligonucleotides specifically hybridize to the annealing site, inducing exon 44 skipping. Other antisense oligonucleotides of the invention are 20 to 50 nucleotides in length and include at least 10, 12, 15, 17, 20 or more, consecutive nucleotides complementary to an exon 44 target region of the dystrophin gene designated as an annealing site selected from the group consisting of: H44A(−07+17) and H44A(+62+89). Yet other antisense oligonucleotides of the invention are 20 to 50 nucleotides in length and include at least 10, 12, 15, 17, 20 or more, consecutive nucleotides complementary to an exon 44 target region of the dystrophin gene designated as an annealing site selected from the group consisting of: H44A(−07+20), H44A(−07+22), H44A(+77+101), H44A(+64+91) and H44A(+62+85).

Other antisense oligonucleotides of the invention are 20 to 50 nucleotides in length and include at least 10, 12, 15, 17, 20 or more, consecutive nucleotides of SEQ ID NOs: 1, or 6. Other embodiments relate to antisense oligonucleotides of 20 to 50 nucleotides in length, including at least 10, 12, 15, 17, 20 or more, consecutive nucleotides of SEQ ID NOs: 2-5 and 7. In some embodiments, thymine bases in SEQ ID NOs: 1-7 are optionally uracil. Exemplary antisense oligomers of the invention are set forth below:

```
H44A(-07+17):
                                    (SEQ ID NO: 1)
5'-CAGATCTGTCAAATCGCCTGCAGG-3'

H44A(-07+20):
                                    (SEQ ID NO: 2)
5'-CAACAGATCTGTCAAATCGCCTGCAGG-3'

H44A(-07+22):
                                    (SEQ ID NO: 3)
5'-CTCAACAGATCTGTCAAATCGCCTGCAGG-3'

H44A(+77+101):
                                    (SEQ ID NO: 4)
5'-GTGTCTTTCTGAGAAACTGTTCAGC-3'

H44A(+64+91):
                                    (SEQ ID NO: 5)
5'-GAGAAACTGTTCAGCTTCTGTTAGCCAC-3'

H44A(+62+89):
                                    (SEQ ID NO: 6)
5'-GAAACTGTTCAGCTTCTGTTAGCCACTG-3'

H44A(+62+85)):
                                    (SEQ ID NO: 7)
5'-CTGTTCAGCTTCTGTTAGCCACTG-3'
```

In a preferred embodiment, the antisense oligomer specifically hybridizes to the annealing site H44A(-07+17), such as SEQ ID NO: 1. In yet another preferred embodiment, the antisense oligomer specifically hybridizes to an annealing site H44A(+62+89), such as SEQ ID NO: 6. In another embodiment, the antisense oligomer is selected from SEQ ID NOS: 1 and 6.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

I. Definitions

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The terms "complementary" and "complementarity" refer to polynucleotides (i.e., a sequence of nucleotides) related by base-pairing rules. For example, the sequence "T-G-A (5'-3')," is complementary to the sequence "T-C-A (5'-3')." Complementarity may be "partial," in which only some of the nucleic acids' bases are matched according to base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" and "CPP" are used interchangeably and refer to cationic cell penetrating peptides, also called transport peptides, carrier peptides, or peptide transduction domains. The peptides, as shown herein, have the capability of inducing cell penetration within 100% of cells of a given cell culture population and allow macromolecular translocation within multiple tissues in vivo upon systemic administration. A preferred CPP embodiment is an arginine-rich peptide as described further below.

The terms "antisense oligomer" and "antisense compound" and "antisense oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits are based on ribose or another pentose sugar or, in a preferred embodiment, a morpholino group (see description of morpholino oligomers below). The oligomer may have exact or near sequence complementarity to the target sequence; variations in sequence near the termini of an oligomer are generally preferable to variations in the interior.

Such an antisense oligomer can be designed to block or inhibit translation of mRNA or to inhibit natural pre-mRNA splice processing, and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. A preferred target sequence is any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide. See, for example, the structure in FIG. 1A, which shows a preferred phosphorodiamidate linkage type. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, 5,506,337, 8,076,476, 8,299,206 and 7,943,762 (cationic linkages), all of which are incorporated herein by reference. Modified intersubunit linkages and terminal groups are detailed in PCT application US2011/038459 and publication WO/2011/150408 which are incorporated herein by reference in their entirety.

An "amino acid subunit" or "amino acid residue" can refer to an α-amino acid residue (—CO—CHR—NH—) or a β- or other amino acid residue (e.g. —CO—(CH$_2$)$_n$CHR—NH—), where R is a side chain (which may include hydrogen) and n is 1 to 6, preferably 1 to 4.

The term "naturally occurring amino acid" refers to an amino acid present in proteins found in nature. The term "non-natural amino acids" refers to those amino acids not present in proteins found in nature, examples include beta-alanine (β-Ala), 6-aminohexanoic acid (Ahx) and 6-aminopentanoic acid.

An "exon" refers to a defined section of nucleic acid that encodes for a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA. The human dystrophin gene has about 79 exons.

An "intron" refers to a nucleic acid region (within a gene) that is not translated into a protein. An intron is a non-coding section that is transcribed into a precursor mRNA (pre-mRNA), and subsequently removed by splicing during formation of the mature RNA.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect. For an antisense oligomer, this effect is typically brought about by inhibiting translation or natural splice-processing of a selected target sequence.

"Exon skipping" refers generally to the process by which an entire exon, or a portion thereof, is removed from a given pre-processed RNA, and is thereby excluded from being present in the mature RNA, such as the mature mRNA that is translated into a protein. Hence, the portion of the protein that is otherwise encoded by the skipped exon is not present in the expressed form of the protein, typically creating an altered, though still functional, form of the protein. In certain embodiments, the exon being skipped is an aberrant exon from the human dystrophin gene, which may contain a mutation or other alteration in its sequence that otherwise causes aberrant splicing. In certain embodiments, the exon being skipped is any one or more of exons 1-79 of the dystrophin gene, though exon 44 of the human dystrophin gene is preferred.

"Dystrophin" is a rod-shaped cytoplasmic protein, and a vital part of the protein complex that connects the cytoskeleton of a muscle fiber to the surrounding extracellular matrix through the cell membrane. Dystrophin contains multiple functional domains. For instance, dystrophin contains an actin binding domain at about amino acids 14-240 and a central rod domain at about amino acids 253-3040. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Repeats 15 and 16 are separated by an 18 amino acid stretch that appears to provide a major site for proteolytic cleavage of dystrophin. The sequence identity between most repeats ranges from 10-25%. One repeat contains three alpha-helices: 1, 2 and 3. Alpha-helices 1 and 3 are each formed by 7 helix turns, probably interacting as a coiled-coil through a hydrophobic interface. Alpha-helix 2 has a more complex structure and is formed by segments of four and three helix turns, separated by a Glycine or Proline residue. Each repeat is encoded by two exons, typically interrupted by an intron between amino acids 47 and 48 in the first part of alpha-helix 2. The other intron is found at different positions in the repeat, usually scattered over helix-3. Dystrophin also contains a cysteine-rich domain at about amino acids 3080-3360), including a cysteine-rich segment (i.e., 15 Cysteines in 280 amino acids) showing homology to the C-terminal domain of the slime mold (Dictyostelium discoideum) alpha-actinin. The carboxy-terminal domain is at about amino acids 3361-3685.

The amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally inherited muscular dystrophies. The DAPC is destabilized when dystrophin is absent, which results in diminished levels of the member proteins, and in turn leads to progressive fibre damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence that lead to incorrect splicing. The predominant expression of the defective dystrophin protein, or the complete lack of dystrophin or a dystrophin-like protein, leads to rapid progression of muscle degeneration, as noted above. In this regard, a "defective" dystrophin protein may be characterized by the forms of dystrophin that are produced in certain subjects with DMD or BMD, as known in the art, or by the absence of detectable dystrophin.

As used herein, the terms "function" and "functional" and the like refer to a biological, enzymatic, or therapeutic function.

A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. As one example, dystrophin-related activity in muscle cultures in vitro can be measured according to myotube size, myofibril organization (or disorganization), contractile activity, and spontaneous clustering of acetylcholine receptors (see, e.g., Brown et al., Journal of Cell Science. 112:209-216, 1999). Animal models are also valuable resources for studying the pathogenesis of disease, and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, Int J Exp Pathol 84: 165-172, 2003). These and other animal models can be used to measure the functional activity of various dystrophin proteins. Included are truncated forms of dystrophin, such as those forms that are produced by certain of the exon-skipping antisense compounds of the present invention.

By "isolated" is meant material that is substantially or essentially free from components that normally accompany it in its native state. For example, an "isolated polynucleotide," as used herein, may refer to a polynucleotide that has been purified or removed from the sequences that flank it in a naturally-occurring state, e.g., a DNA fragment that has been removed from the sequences that are normally adjacent to the fragment.

As used herein, "sufficient length" refers to an antisense oligonucleotide that is complementary to at least 8, more typically 8-30, contiguous nucleobases in a target dystrophin pre-mRNA. In some embodiments, an antisense of sufficient length includes at least 8, 9, 10, 11, 12, 13, 14, or 15 contiguous nucleobases in the target dystrophin pre-mRNA. In other embodiments an antisense of sufficient length includes at least 16, 17, 18, 19, 20, 21, 22, 23, 24, or 25 contiguous nucleobases in the target dystrophin pre-mRNA. An antisense oligonucleotide of sufficient length has at least a minimal number of nucleotides to be capable of specifically hybridizing to exon 44. Preferably an oligonucleotide of sufficient length is from about 10 to about 50 nucleotides in length, including oligonucleotides of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 or more nucleotides. In one embodiment, an oligonucleotide of sufficient length is from 10 to about 30 nucleotides in length. In another embodiment, an oligonucleotide of sufficient length is from 15 to about 25 nucleotides in length. In yet another embodiment, an oligonucleotide of sufficient length is from 20 to 30, or 20 to 50, nucleotides in length. In yet another embodiment, an oligonucleotide of sufficient length is from 25 to 28 nucleotides in length.

By "enhance" or "enhancing," or "increase" or "increasing," or "stimulate" or "stimulating," refers generally to the ability of one or antisense compounds or compositions to produce or cause a greater physiological response (i.e., downstream effects) in a cell or a subject, as compared to the response caused by either no antisense compound or a control compound. A measurable physiological response may include increased expression of a functional form of a dystrophin protein, or increased dystrophin-related biological activity in muscle tissue, among other responses apparent from the understanding in the art and the description herein. Increased muscle function can also be measured, including increases or improvements in muscle function by about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 600%, 65%, 70%, 75%, 80%, 85%, 90%, 95%, or 100%. The percentage of muscle fibres that express a functional dystrophin can also be measured, including increased dystrophin expression in about 1%, 2%, %, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibres. For instance, it has been shown that around 40% of muscle function improvement can occur if 25-30% of fibers express dystrophin (see, e.g., DelloRusso et al, Proc Natl Acad Sci USA 99: 12979-12984, 2002). An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The term "reduce" or "inhibit" may relate generally to the ability of one or more antisense compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of muscular dystrophy, or reductions in the expression of defective forms of dystrophin, such as the altered forms of dystrophin that are expressed in individuals with DMD or BMD. A "decrease" in a response may be statistically significant as compared to the response produced by no antisense compound or a control composition, and may include a 1%, 2%, 3%, 4%, 5%, 6%, 7° %, 8%, 9%, 10%, 11%, 12%, 13%, 14%, 15%, 16%, 17%, 18%, 19%, 20%, 25%, 30%, 35%, 40%, 45%, 500, 55%, 60%, 65%, 70%, 75%, 80%, 85%, 90%, 95%, or 100% decrease, including all integers in between.

Also included are vector delivery systems that are capable of expressing the oligomeric, dystrophin-targeting sequences of the present invention, such as vectors that express a polynucleotide sequence comprising any one or more of SEQ ID NOs: 1 and 9-13, as described herein. By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

Hence, included are methods of treating muscular dystrophy, such as DMD and BMD, by administering one or more antisense oligomers of the present invention (e.g., SEQ ID NOs: 1 and 6, and variants thereof), optionally as part of a pharmaceutical formulation or dosage form, to a subject in need thereof. Also included are methods of inducing exon-skipping in a subject by administering one or more antisense oligomers, in which the exon is exon 44 from the dystrophin gene, preferably the human dystrophin gene. A "subject," as used herein, includes any animal that exhibits a symptom, or is at risk for exhibiting a symptom, which can be treated with an antisense compound of the invention, such as a subject that has or is at risk for having DMD or BMD, or any of the symptoms associated with these conditions (e.g., muscle fibre loss). Suitable subjects (patients) include laboratory animals (such as mouse, rat, rabbit, or guinea pig), farm animals, and domestic animals or pets (such as a cat or dog). Non-human primates and, preferably, human patients, are included.

"Alkyl" or "alkylene" both refer to a saturated straight or branched chain hydrocarbon radical containing from 1 to 18 carbons. Examples include without limitation methyl, ethyl, propyl, iso-propyl, butyl, iso-butyl, tert-butyl, n-pentyl and n-hexyl. The term "lower alkyl" refers to an alkyl group, as defined herein, containing between 1 and 8 carbons.

"Alkenyl" refers to an unsaturated straight or branched chain hydrocarbon radical containing from 2 to 18 carbons and comprising at least one carbon to carbon double bond. Examples include without limitation ethenyl, propenyl, iso-propenyl, butenyl, iso-butenyl, tert-butenyl, n-pentenyl and n-hexenyl. The term "lower alkenyl" refers to an alkenyl group, as defined herein, containing between 2 and 8 carbons.

"Alkynyl" refers to an unsaturated straight or branched chain hydrocarbon radical containing from 2 to 18 carbons comprising at least one carbon to carbon triple bond. Examples include without limitation ethynyl, propynyl, iso-propynyl, butynyl, iso-butynyl, tert-butynyl, pentynyl and hexynyl. The term "lower alkynyl" refers to an alkynyl group, as defined herein, containing between 2 and 8 carbons.

"Cycloalkyl" refers to a mono- or poly-cyclic alkyl radical. Examples include without limitation cyclobutyl, cyclopentyl, cyclohexyl, cycloheptyl and cyclooctyl.

"Aryl" refers to a cyclic aromatic hydrocarbon moiety containing from to 18 carbons having one or more closed ring(s). Examples include without limitation phenyl, benzyl, naphthyl, anthracenyl, phenanthracenyl and biphenyl.

"Aralkyl" refers to a radical of the formula RaRb where Ra is an alkylene chain as defined above and Rb is one or more aryl radicals as defined above, for example, benzyl, diphenylmethyl and the like.

"Thioalkoxy" refers to a radical of the formula —SRc where Rc is an alkyl radical as defined herein. The term "lower thioalkoxy" refers to an alkoxy group, as defined herein, containing between 1 and 8 carbons.

"Alkoxy" refers to a radical of the formula —ORda where Rd is an alkyl radical as defined herein. The term "lower alkoxy" refers to an alkoxy group, as defined herein, containing between 1 and 8 carbons. Examples of alkoxy groups include, without limitation, methoxy and ethoxy.

"Alkoxyalkyl" refers to an alkyl group substituted with an alkoxy group.

"Carbonyl" refers to the C(=O)— radical.

"Guanidynyl" refers to the $H_2N(C=NH_2)$—NH— radical.

"Amidinyl" refers to the $H_2N(C=NH_2)$CH— radical.

"Amino" refers to the $NH_2$ radical.

"Alkylamino" refers to a radical of the formula —NHRd or —NRdRd where each Rd is, independently, an alkyl radical as defined herein. The term "lower alkylamino" refers to an alkylamino group, as defined herein, containing between 1 and 8 carbons.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, piperizinyl, hydantoinyl, valerolactamyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, tetrahydrothiopyranyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

The terms "optionally substituted alkyl", "optionally substituted alkenyl", "optionally substituted alkoxy", "optionally substituted thioalkoxy", "optionally substituted alkyl amino", "optionally substituted lower alkyl", "optionally substituted lower alkenyl", "optionally substituted lower alkoxy", "optionally substituted lower thioalkoxy", "optionally substituted lower alkyl amino" and "optionally substituted heterocyclyl" mean that, when substituted, at least one hydrogen atom is replaced with a substituent. In the case of an oxo substituent (=O) two hydrogen atoms are replaced. In this regard, substituents include: deuterium, optionally substituted alkyl, optionally substituted alkenyl, optionally substituted alkynyl, optionally substituted aryl, optionally substituted heterocycle, optionally substituted cycloalkyl, oxo, halogen, —CN, —ORx, NRxRy, NRxC(=O)Ry, NRxSO2Ry, —NRxC(=O)NRxRy, C(=O)Rx, C(=O)ORx, C(=O)NRxRy, —SOmRx and —SOmNRxRy, wherein m is 0, 1 or 2, Rx and Ry are the same or different and independently hydrogen, optionally substituted alkyl, optionally substituted alkenyl, optionally substituted alkynyl, optionally substituted aryl, optionally substituted heterocycle or optionally substituted cycloalkyl and each of said optionally substituted alkyl, optionally substituted alkenyl, optionally substituted alkynyl, optionally substituted aryl, optionally substituted heterocycle and optionally substituted cycloalkyl substituents may be further substituted with one or more of oxo, halogen, —CN, —ORx, NRxRy, NRxC(=O)Ry, NRxSO2Ry, —NRxC(=O)NRxRy, C(=O)Rx, C(=O)ORx, C(=O)NRxRy, —SOmRx and —SOmNRxRy.

An antisense molecule nomenclature system was proposed and published to distinguish between the different antisense molecules (see Mann et al., (2002) J Gen Med 4, 644-654). This nomenclature became especially relevant when testing several slightly different antisense molecules, all directed at the same target region, as shown below:

H#A/D(x:y).

The first letter designates the species (e.g. H: human, M: murine, C: canine). "#" designates target dystrophin exon number. "A/D" indicates acceptor or donor splice site at the beginning and end of the exon, respectively. (x y) represents the annealing coordinates where "−" or "+" indicate intronic or exonic sequences respectively. For example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2-18) where the last 2 exonic bases and the first 18 intronic bases correspond to the annealing site of the antisense molecule. Entirely exonic annealing coordinates that would be represented by A(+65+85), that is the site between the 65th and 85th nucleotide from the start of that exon.

II. Constructing the Antisense Oligonucleotide

Figure 1B:
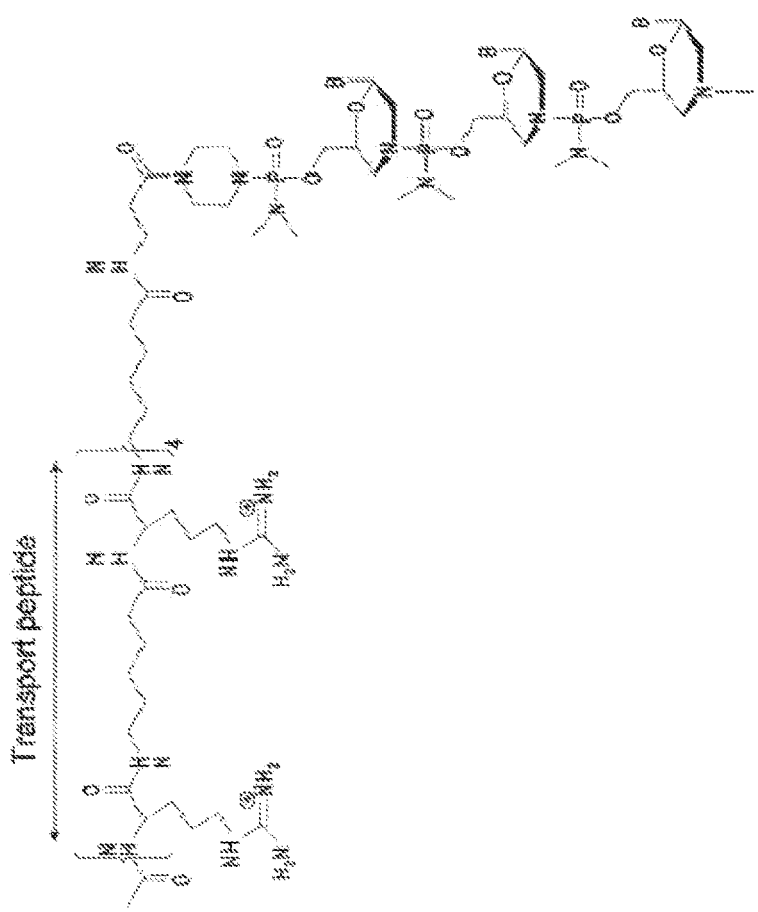
FIG. 1B shows a conjugate of an arginine-rich peptide and an antisense oligomer, in accordance with an embodiment of the invention.
Figure 1C:
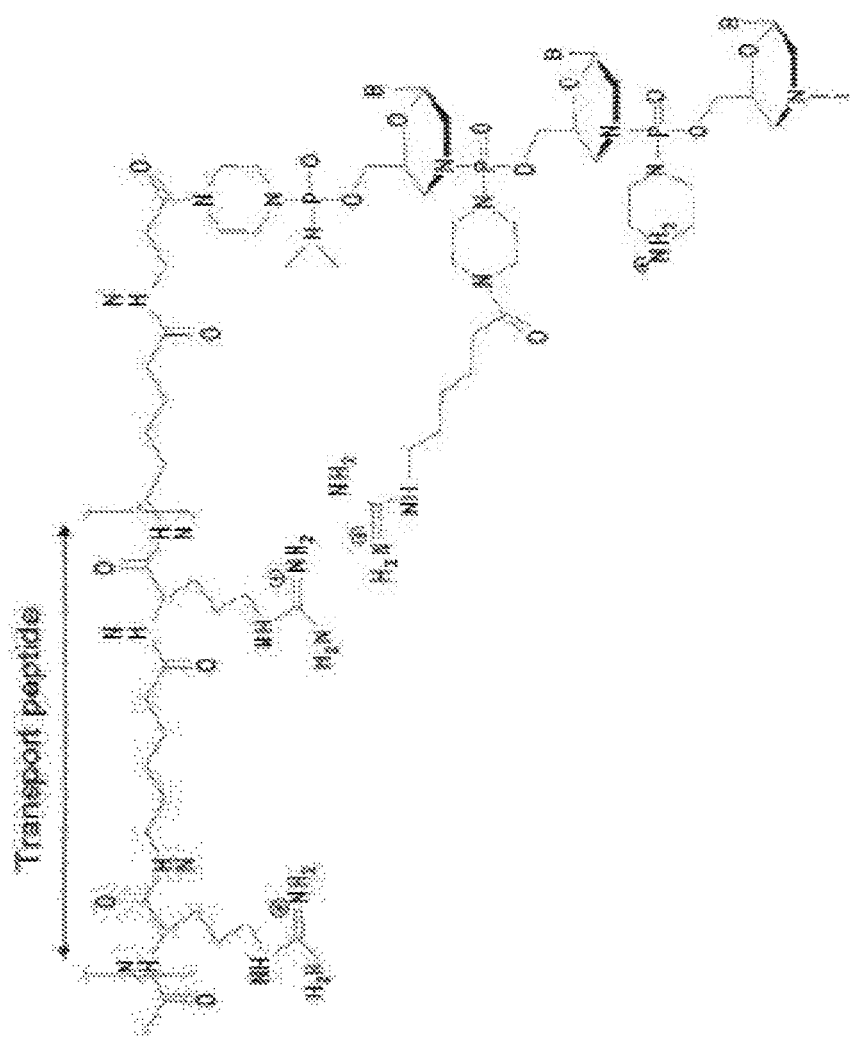
FIG. 1C shows a conjugate as in FIG. 1B, wherein the backbone linkages contain one or more positively charged groups.

Exemplary embodiments of the invention relate to morpholino oligonucleotides having phosphorus-containing backbone linkages are illustrated in FIGS. 1A-1C. Preferred is a phosphorodiamidate-linked morpholino oligonucleotide such as shown in FIG. 1C, which is modified, in accordance with one aspect of the present invention, to contain positively charged groups at preferably 10%-50% of its backbone linkages. Morpholino oligonucleotides with uncharged backbone linkages, including antisense oligonucleotides, are detailed, for example, in (Summerton and Weller 1997) and in co-owned U.S. Pat. Nos. 5,698,685, 5,217,866, 5,142,047, 5,034,506, 5,166,315, 5,185,444, 5,521,063, 5,506,337, 8,076,476, 8,299,206 and 7,943,762 all of which are expressly incorporated by reference herein.

Important properties of the morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNAse and RNase H degradation, respectively.

Figure 1D:
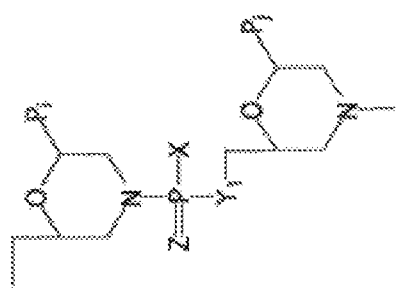
FIG. 1D-FIG. 1G show the repeating subunit segment of exemplary morpholino oligonucleotides, designated D through G.
Figure 1E:
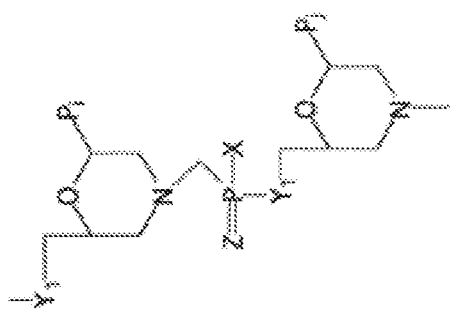

Exemplary backbone structures for antisense oligonucleotides of the claimed subject matter include the morpholino subunit types shown in FIGS. 1D-G, each linked by an uncharged or positively charged, phosphorus-containing subunit linkage. FIG. 1D shows a phosphorus-containing linkage which forms the five atom repeating-unit backbone, where the morpholino rings are linked by a 1-atom phosphoamide linkage. FIG. 1E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1F:
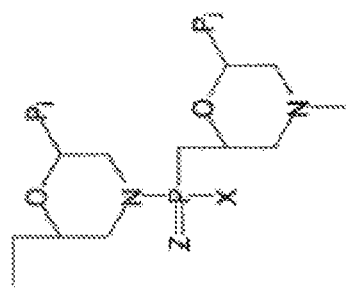
Figure 1G:
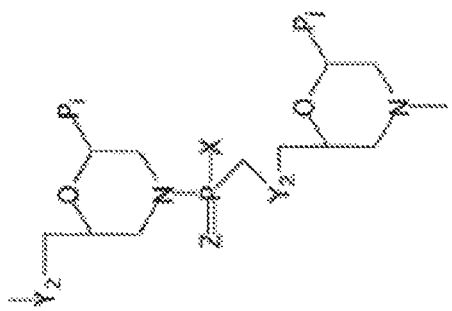
Figure 2:
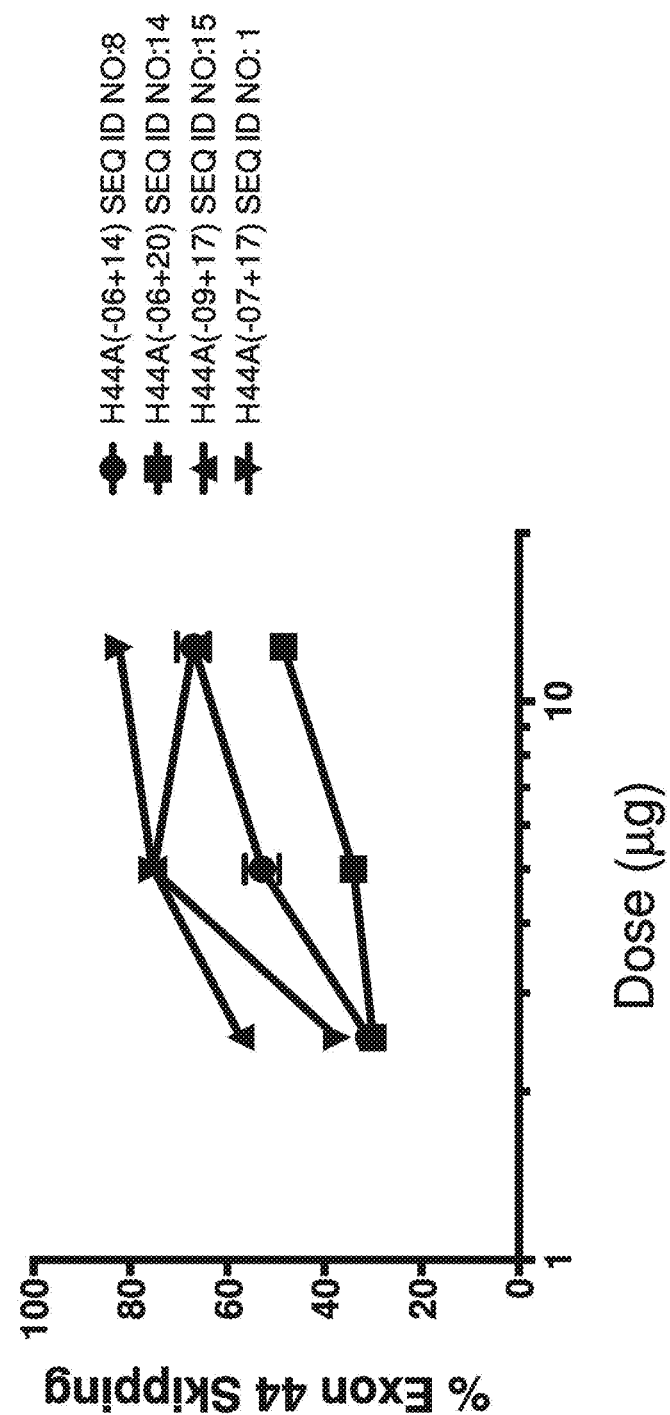
FIG. 2 and FIG. 3 depict graphs corresponding to experiments showing relative activities of exemplary antisense oligomers for inducing exon 44 skipping in cultured human rhabdomyosarcoma cells. RNA isolated from rhabdomyosarcoma cells treated with the indicated oligomers was subjected to exon 44-specific nested RT-PCR amplification, followed by gel electrophoresis and band intensity quantification. Data are plotted as % exon skipping as assessed by PCR i.e., the band intensity of the exon-skipped product relative to the full-length PCR product.

The linkages shown in FIGS. 1F and 1G are designed for 7-atom unit-length backbones. In structure 1F, the X moiety is as in Structure 1E, and the Y moiety may be methylene, sulfur, or, preferably, oxygen. In Structure 1G, the X and Y moieties are as in Structure 1E. Particularly preferred morpholino oligonucleotides include those composed of morpholino subunit structures of the form shown in FIG. 1E, where $X=NH_2$, $N(CH_3)_2$, or 1-piperazine or other charged group, $Y=O$, and $Z=O$.

A substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, according to standard synthetic methods. For example, addition of a polyethylene glycol moiety or other hydrophilic polymer, e.g., one having 1-100 monomeric subunits, may be useful in enhancing solubility.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

Oligomers for use in antisense applications generally range in length from about 10 to about 50 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages. In a preferred embodiment, the oligomers have 25 to 28 subunits.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

As noted above, certain embodiments are directed to oligomers comprising novel intersubunit linkages, including PMO-X oligomers and those having modified terminal groups. In some embodiments, these oligomers have higher affinity for DNA and RNA than do the corresponding unmodified oligomers and demonstrate improved cell delivery, potency, and/or tissue distribution properties compared to oligomers having other intersubunit linkages. The structural features and properties of the various linkage types and oligomers are described in more detail in the following discussion. The synthesis of these and related oligomers is described in co-owned U.S. application Ser. No. 13/118,298, which is incorporated by reference in its entirety.

In certain embodiments, the invention provides for an oligonucleotide having a sequence complementary to the target sequence which is associated with a human disease, and comprises a sequence of nucleotides having a formula:

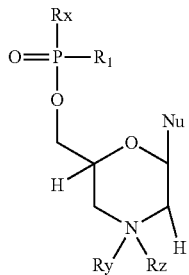

wherein Nu is a nucleobase;
$R_1$ has the formula

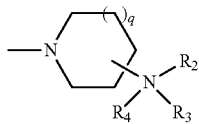

q is 0, 1, or 2;

$R_2$ is selected from the group consisting of hydrogen, $C_1$-$C_5$ alkyl, $C_1$-$C_5$ aralkyl, and a formamidinyl group, and $R_3$ is selected from the group consisting of hydrogen, $C_1$-$C_{10}$ acyl, $C_1$-$C_{10}$ aminoacyl, acyl moiety of a natural or unnatural alpha or beta amino acid, $C_1$-$C_{10}$ aralkyl, and $C_1$-$C_{10}$ alkyl, or $R_2$ and $R_3$ are joined to form a 5-7 membered ring where the ring may be optionally substituted with a substituent selected from the group consisting of $C_1$-$C_{10}$ alkyl, phenyl, halogen, and $C_1$-$C_{10}$ aralkyl;

$R_4$ is selected from the group consisting of an electron pair, hydrogen, a $C_1$-$C_6$ alkyl and $C_1$-$C_6$ aralkyl;

Rx is selected from the group consisting of sarcosinamide, hydroxyl, a nucleotide, a cell penetrating peptide moiety, and piperazinyl;

Ry is selected from the group consisting of hydrogen, a $C_1$-$C_6$ alkyl, a nucleotide a cell penetrating peptide moiety, an amino acid, a formamidinyl group, and $C_1$-$C_6$ acyl; and, Rz is selected from the group consisting of an electron pair, hydrogen, a $C_1$-$C_6$ alkyl, and $C_1$-$C_6$ acyl pharmaceutically acceptable salts thereof.

Nu may be selected from the group consisting of adenine, guanine, thymine, uracil, cytosine, and hypoxanthine. More preferably Nu is thymine or uracil.

In preferred embodiments, the invention provides an oligonucleotide having a sequence of nucleotides having a formula:

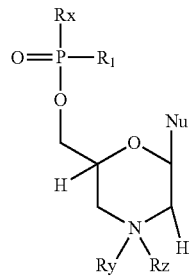

wherein Nu is a nucleobase;
$R_1$ is selected from the group consisting of $R_1'$ and $R_1''$ wherein $R_1'$ is dimethyl-amino and $R_1''$ has the formula

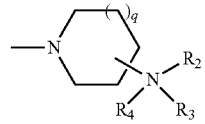

wherein at least one $R_1$ is $R_1''$;
q is 0, 1, or 2; with the proviso that at least one of $R_1$ is a piperidinyl moiety;

$R_2$ is selected from the group consisting of hydrogen, $C_1$-$C_5$ alkyl, $C_1$-$C_5$ aralkyl, and a formamidinyl group, and $R_3$ is selected from the group consisting of hydrogen, $C_1$-$C_{10}$ acyl, $C_1$-$C_{10}$ aminoacyl, acyl moiety of a natural or unnatural alpha or beta amino acid, $C_1$-$C_{10}$ aralkyl, and $C_1$-$C_{10}$ alkyl, or $R_2$ and $R_3$ are joined to form a 5-7 membered ring where the ring may be optionally substituted with a substituent selected from the group consisting of $C_1$-$C_{10}$ alkyl, phenyl, halogen, and $C_1$-$C_{10}$ aralkyl;

$R_4$ is selected from the group consisting of an electron pair, hydrogen, a $C_1$-$C_6$ alkyl and aralkyl;

Rx is selected from the group consisting of sarcosinamide, hydroxyl, a nucleotide, a cell penetrating peptide moiety, and piperazinyl;

Ry is selected from the group consisting of hydrogen, a $C_1$-$C_6$ alkyl, a nucleotide a cell penetrating peptide moiety, an amino acid, a formamidinyl group, and $C_1$-$C_6$ acyl; and, Rz is selected from the group consisting of an electron pair, hydrogen, a $C_1$-$C_6$ alkyl, and $C_1$-$C_6$ acyl pharmaceutically acceptable salts thereof.

Nu may be selected from the group consisting of adenine, guanine, thymine, uracil, cytosine, and hypoxanthine. More preferably Nu is thymine or uracil.

About 90-50% of the $R_1$ groups are dimethylamino (i.e. $R_1'$). More, preferably, 90-50% of the $R_1$ groups are dimethylamino. Most, preferably about 66% of the $R_1$ groups are dimethylamino.

$R_1''$ may be selected from the group consisting of

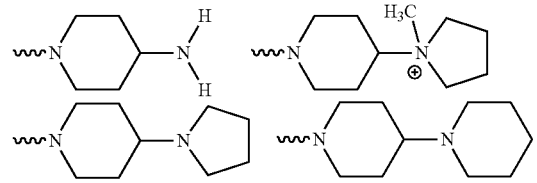

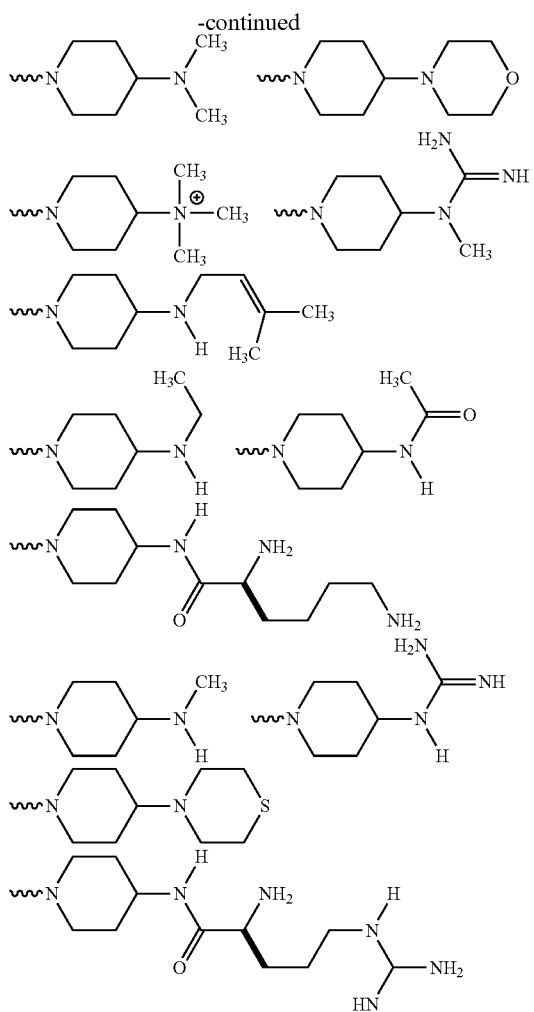

Preferably, at least one nucleotide of the oligonucleotide has the formula:

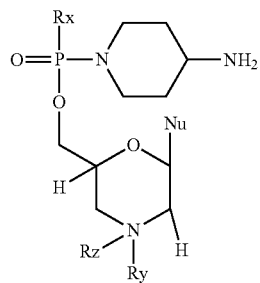

wherein Rx, Ry, Rz, and Nu are as stated above. Most preferably, Nu is thymine or uracil.

Although thymine (T) is the preferred base pairing moiety (Nu or Pi) containing the chemical modifications described above, any base subunit known to a person of skill in the art can be used as the base pairing moiety.

The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense molecule need not be 100% complementary to that of its target sequence to be specifically hybridizable. An antisense molecule is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While the above method may be used to select antisense molecules capable of deleting any exon from within a protein that is capable of being shortened without affecting its biological function, the exon deletion should not lead to a reading frame shift in the shortened transcribed mRNA. Thus, if in a linear sequence of three exons the end of the first exon encodes two of three nucleotides in a codon and the next exon is deleted then the third exon in the linear sequence must start with a single nucleotide that is capable of completing the nucleotide triplet for a codon. If the third exon does not commence with a single nucleotide there will be a reading frame shift that would lead to the generation of truncated or a non-functional protein.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of antisense oligonucleotides may need to be selected by the method of the invention wherein each is directed to a different region responsible for inducing splicing in the exons that are to be deleted.

The length of an antisense molecule may vary so long as it is capable of binding selectively to the intended location within the pre-mRNA molecule. The length of such sequences can be determined in accordance with selection procedures described herein. Generally, the antisense molecule will be from about 10 nucleotides in length up to about 50 nucleotides in length. It will be appreciated however that any length of nucleotides within this range may be used in the method. Preferably, the length of the antisense molecule is between 10-30 nucleotides in length.

The most common method for producing antisense molecules is the methylation of the 2' hydroxyribose position and the incorporation of a phosphorothioate backbone produces molecules that superficially resemble RNA but that are much more resistant to nuclease degradation.

To avoid degradation of pre-mRNA during duplex formation with the antisense molecules, the antisense molecules used in the method may be adapted to minimize or prevent cleavage by endogenous RNase H. This property is highly preferred as the treatment of the RNA with the unmethylated oligonucleotides either intracellularly or in crude extracts that contain RNase H leads to degradation of the pre-mRNA: antisense oligonucleotide duplexes. Any form of modified antisense molecules that is capable of by-passing or not inducing such degradation may be used in the present method. An example of antisense molecules which when duplexed with RNA are not cleaved by cellular RNase H is 2'-O-methyl derivatives. 2'-O-methyl-oligoribonucleotides are very stable in a cellular environment and in animal tissues, and their duplexes with RNA have higher Tm values than their ribo- or deoxyribo-counterparts.

Antisense molecules that do not activate RNase H can be made in accordance with known techniques (see, e.g., U.S. Pat. No. 5,149,797). Such antisense molecules, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense molecules that do not activate RNase H are available. For example, such antisense molecules may be oligonucleotides wherein at least one, or all, of the inter-nucleotide bridging phosphate residues are modified phosphates, such as methyl phosphonates, methyl phosphorothioates, phosphoromorpholidates, phosphoropiperazidates and phosphoramidates. For example, every other one of the internucleotide bridging phosphate residues may be modified as described. In another non-limiting example, such antisense molecules are molecules wherein at least one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While antisense oligonucleotides are a preferred form of the antisense molecules, the present invention comprehends other oligomeric antisense molecules, including but not limited to oligonucleotide mimetics such as are described below.

Specific examples of preferred antisense compounds useful in this invention include oligonucleotides containing modified backbones or non-natural inter-nucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their inter-nucleoside backbone can also be considered to be oligonucleosides.

In other preferred oligonucleotide mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone.

Modified oligonucleotides may also contain one or more substituted sugar moieties. Oligonucleotides may also include nucleobase (often referred to in the art simply as "base") modifications or substitutions. Certain nucleo-bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of this invention, are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

III. Peptide Transporters

The antisense compounds of the invention may include an oligonucleotide moiety conjugated to a CPP, preferably an arginine-rich peptide transport moiety effective to enhance transport of the compound into cells. The transport moiety is preferably attached to a terminus of the oligomer, as shown, for example, in FIGS. 1B and 1C. The peptides have the capability of inducing cell penetration within 30%, 400, 50%, 60/o, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter. In another embodiment, the cell-penetrating peptide may be Penetratin or the Tat peptide. These peptides are well known in the art and are disclosed, for example, in US Publication No. 2010-0016215 A1, incorporated by reference in its entirety. A particularly preferred approach to conjugation of peptides to antisense oligonucleotides can be found in PCT publication WO2012/150960, which is incorporated by reference in its entirety. A preferred embodiment of a peptide conjugated oligonucleotide of the present invention utilizes glycine as the linker between the CPP and the antisense oligonucleotide. For example, a preferred peptide conjugated PMO consists of $R_6$-G-PMO.

The transport moieties as described above have been shown to greatly enhance cell entry of attached oligomers, relative to uptake of the oligomer in the absence of the attached transport moiety. Uptake is preferably enhanced at least ten fold, and more preferably twenty fold, relative to the unconjugated compound.

The use of arginine-rich peptide transporters (i.e., cell-penetrating peptides) are particularly useful in practicing the present invention. Certain peptide transporters have been shown to be highly effective at delivery of antisense compounds into primary cells including muscle cells (Marshall, Oda et al. 2007; Jearawiriyapaisarn, Moulton et al. 2008; Wu, Moulton et al. 2008). Furthermore, compared to other known peptide transporters such as Penetratin and the Tat peptide, the peptide transporters described herein, when conjugated to an antisense PMO, demonstrate an enhanced ability to alter splicing of several gene transcripts (Marshall, Oda et al. 2007).

Exemplary peptide transporters, excluding linkers are given below in Table 1.

TABLE 1

Exemplary peptide transporters

| NAME (DESIGNATION) | SEQUENCE | SEQ ID NO[A] |
|---|---|---|
| rTAT | RRRQRRKKR | 19 |
| Tat | RKKRRQRRR | 20 |
| $R_9F_2$ | RRRRRRRRRFF | 21 |
| $R_5F_2R_4$ | RRRRRFFRRRR | 22 |
| $R_4$ | RRRR | 23 |
| $R_5$ | RRRRR | 24 |
| $R_6$ | RRRRRR | 25 |
| $R_7$ | RRRRRRR | 26 |
| $R_8$ | RRRRRRRR | 27 |
| $R_9$ | RRRRRRRRR | 28 |
| $(RX)_8$ | RXRXRXRXRXRXRXRX | 29 |
| $(RAhxR)_4$; (P007) | RAhxRRAhxRRAhxRRAhxR | 30 |
| $(RAhxR)_5$; (CP04057) | RAhxRRAhxRRAhxRRAhxRRAhxR | 31 |
| $(RAhxRRBR)_2$, (CP06062) | RAhxRRBRRAhxRRBR | 32 |
| $(RAR)_4F_2$ | RARRARRARRARFF | 33 |
| $(RGR)_4F_2$ | RGRRGRRGRRGRFF | 34 |

[A]Sequences assigned to SEQ ID NOs do not include the linkage portion (e.g., C, G, P, Ahx, B, AhxB where Ahx and B refer to 6-aminohexanoic acid and beta-alanine, respectively).

IV. Formulations

In certain embodiments, the present invention provides formulations or compositions suitable for the therapeutic delivery of antisense oligomers, as described herein. Hence, in certain embodiments, the present invention provides pharmaceutically acceptable compositions that comprise a therapeutically-effective amount of one or more of the oligomers described herein, formulated together with one or more pharmaceutically acceptable carriers (additives) and/or diluents. While it is possible for an oligomer of the present invention to be administered alone, it is preferable to administer the compound as a pharmaceutical formulation (composition).

Methods for the delivery of nucleic acid molecules are described, for example, in Akhtar et al., 1992, Trends Cell Bio., 2:139; and Delivery Strategies for Antisense Oligonucleotide Therapeutics, ed. Akhtar; Sullivan et al., PCT WO 94/02595. These and other protocols can be utilized for the delivery of virtually any nucleic acid molecule, including the isolated oligomers of the present invention.

As detailed below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999).

The invention also features the use of the composition comprising surface-modified liposomes containing poly (ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870, Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present invention includes oligomer compositions prepared for delivery as described in U.S. Pat. Nos. 6,692,911, 7,163,695 and 7,070,807. In this regard, in one embodiment, the present invention provides an oligomer of the present invention in a composition comprising copolymers of lysine and histidine (HK) (as described in U.S. Pat. Nos. 7,163,695, 7,070,807, and 6,692,911) either alone or in combination with PEG (e.g., branched or unbranched PEG or a mixture of both), in combination with PEG and a targeting moiety or any of the foregoing in combination with a crosslinking agent. In certain embodiments, the present invention provides antisense oligomers in compositions comprising gluconic-acid-modified polyhistidine or gluconylated-polyhistidine/transferrin-polylysine. One skilled in the art will also recognize that amino acids with properties similar to His and Lys may be substituted within the composition.

Certain embodiments of the oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject oligomers include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the oligomers of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from cyclodextrins, celluloses, liposomes, micelle forming agents, e.g., bile acids, and polymeric carriers, e.g., polyesters and polyanhydrides; and an oligomer of the present invention. In certain embodiments, an aforementioned formulation renders orally bioavailable an oligomer of the present invention.

Methods of preparing these formulations or compositions include the step of bringing into association an oligomer of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An oligomer of the present invention may also be administered as a bolus, electuary or paste.

In solid dosage forms of the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of the present invention to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also prepared by entrapping the drug in liposomes or microemulsions that are compatible with body tissues.

When the oligomers of the present invention are administered as pharmaceuticals, to humans and animals, they can be given per se or as a pharmaceutical composition containing, for example, 0.1 to 99% (more preferably, 10 to 30) of active ingredient in combination with a pharmaceutically acceptable carrier.

As noted above, the formulations or preparations of the present invention may be given orally, parenterally, topically, or rectally. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers of the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of the present invention employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to maintain the desired expression of a functional dystrophin protein.

Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β, or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several non-concentric membranes, i.e., several smaller vesicles contained within a larger vesicle, are termed multivesicular vesicles.

One aspect of the present invention relates to formulations comprising liposomes containing an oligomer of the present invention, where the liposome membrane is formulated to provide a liposome with increased carrying capacity. Alternatively or in addition, the compound of the present invention may be contained within, or adsorbed onto, the liposome bilayer of the liposome. An oligomer of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPGs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMOs in the micromolar range; higher CMC surfactants may be utilized to prepare micelles entrapped within liposomes of the present invention.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV. Amsterdam, 1993. For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT® and Lipofectamine® may be utilized to introduce polynucleotides or proteins into cells.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An oligomer may be formulated to be contained within, or, adapted to release by a surgical or medical device or implant. In certain aspects, an implant may be coated or otherwise treated with an oligomer. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of muscular dystrophy, such as myoblast transplantation, stem cell therapies, administration of aminoglycoside antibiotics, proteasome inhibitors, and up-regulation therapies (e.g., upregulation of utrophin, an autosomal paralogue of dystrophin).

The routes of administration described are intended only as a guide since a skilled practitioner will be able to determine readily the optimum route of administration and any dosage for any particular animal and condition. Multiple approaches for introducing functional new genetic material into cells, both in vitro and in vivo have been attempted (Friedmann (1989) Science, 244:1275-1280). These approaches include integration of the gene to be expressed into modified retroviruses (Friedmann (1989) supra; Rosenberg (1991) Cancer Research 51(18), suppl.: 5074S-5079S); integration into non-retrovirus vectors (e.g., adeno-associated viral vectors) (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256: 808-813.

V. Kits

The invention also provides kits for treatment of a patient with a genetic disease which kit comprises at least an antisense molecule (e.g., an antisense oligomer set forth in SEQ ID NOs: 1 and 9-13), packaged in a suitable container, together with instructions for its use. The kits may also contain peripheral reagents such as buffers, stabilizers, etc. Those of ordinary skill in the field should appreciate that applications of the above method has wide application for identifying antisense molecules suitable for use in the treatment of many other diseases.

VI. Examples

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

Materials and Methods

Cells and Tissue Culture Treatment Conditions

Human Rhabdomyosarcoma cells (ATCC, CCL-136; RD cells) were seeded into tissue culture-treated T75 flasks (Nunc) at $1.5 \times 10^6$ cells/flask in 24 mL of warmed DMEM with L-Glutamine (HyClone), 10% fetal bovine serum, and 1% Penicillin-Streptomycin antibiotic solution (CelGro); after 24 hours, media was aspirated, cells were washed once in warmed PBS, and fresh media was added. Cells were grown to 80% confluence in a 37° C. incubator at 5.0%. CO2 and harvested using trypsin. Lyophilized phosphorodiamidate morpholino oligomers (PMOs) were re-suspended at approximately 2.0 mM in nuclease-free water; to verify molarity, PMO solutions were measured using a NanoDrop 2000 spectrophotometer (Thermo Scientific). PMOs were delivered to RD cells using nucleoporation according to the manufacturer's instructions and the SG kit (Lonza). PMOs were tested at various concentrations (e.g., 2.5, 5, 12.5 and 25 micromolar). Cells were incubated for 24 hours post nucleoporation at $3 \times 10^5$ cells per well of a 12-well plate (n=3) and then subjected to RNA extraction as described below.

Primary human myoblasts were cultured in Skeletal Muscle Cell Growth Media (PromoCell) using standard techniques. Nucleoporation of the PMOs at various concentrations was done as described for RD cells above. Cells were then plated in triplicate wells of a 12-well plate in PromoCell growth media and allowed to incubate for 24 hours before RNA extraction as described below.

RNA Extraction and PCR Amplification

RNA was extracted from PMO-treated cells (RD cells or primary human myoblasts) using the RNAspin 96 well RNA isolation kit from GE Healthcare and subjected to nested RT-PCR using standard techniques and the following primer pairs. Outer primers: forward

```
                                    (SEQ ID NO: 35)
5'-CAATGCTCCTGACCTCTGTGC-3', reverse
                                    (SEQ ID NO: 36)
5'-GCTCTTTTCCAGGTTCAAGTGG-3';

inner primers:
forward
                                    (SEQ ID NO: 37)
5'-GTCTACAACAAAGCTCAGGTCG-3', reverse
```

```
                                    (SEQ ID NO: 38)
5'-GCAATGTTATCTGCTTCCTCCAACC-3',
```

Figure 3:
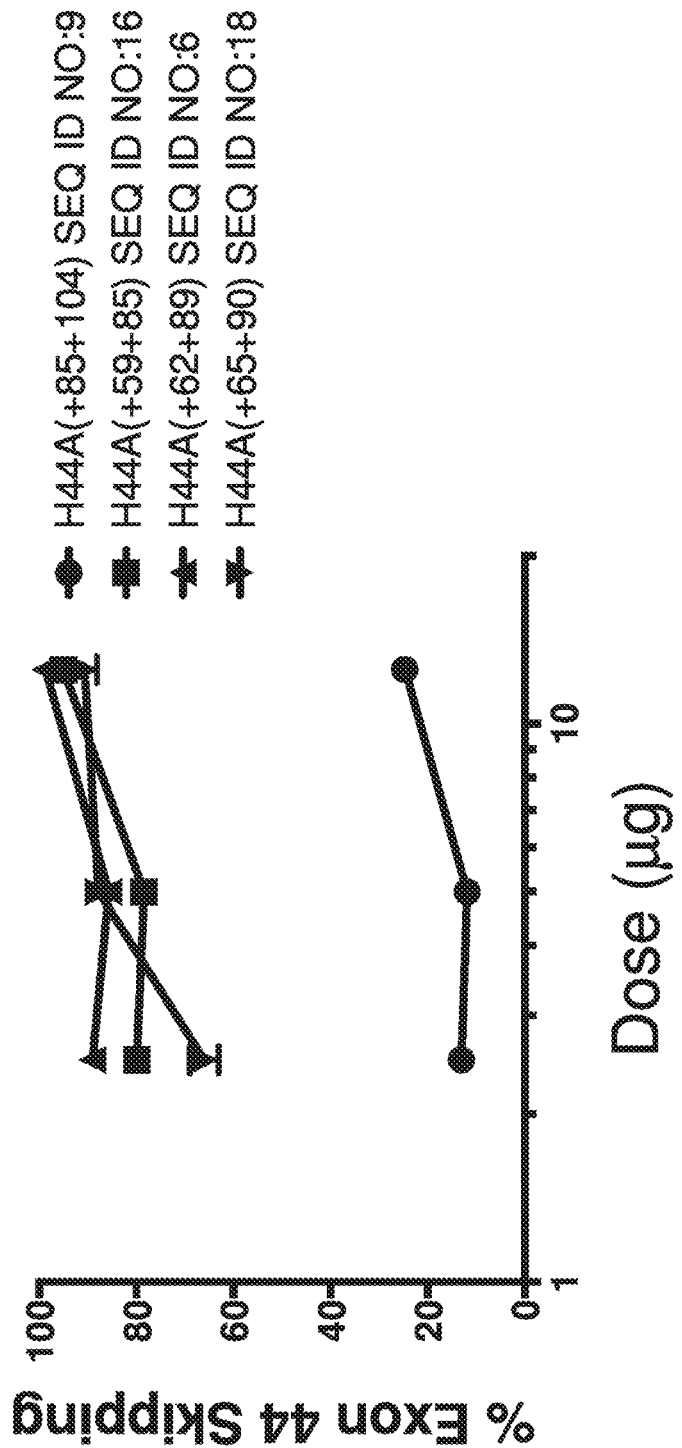

Exon skipping was measured using the Caliper LabChip bioanalyzer and the % exon skipping (i.e., band intensity of the exon-skipped product relative to the full length PCR product) was graphed as shown in FIGS. 3 and 4.

Example 1

Exon 44 Skipping

A series of antisense oligomers that target human dystrophin exon 44 were designed and synthesized as follows:

| Description | Sequence | SEQ ID NO |
|---|---|---|
| H44A(-07+17) | CAGATCTGTCAAATCGCCTGCAGG | 1 |
| H44A(-07+20) | CAACAGATCTGTCAAATCGCCTGCAGG | 2 |
| H44A(-07+22) | CTCAACAGATCTGTCAAATCGCCTGCAGG | 3 |
| H44A(+77+101) | GTGTCTTTCTGAGAAACTGTTCAGC | 4 |
| H44A(+64+91) | GAGAAACTGTTCAGCTTCTGTTAGCCAC | 5 |
| H44A(+62+89) | GAAACTGTTCAGCTTCTGTTAGCCACTG | 6 |
| H44A(+62+85) | CTGTTCAGCTTCTGTTAGCCACTG | 7 |

The antisense oligomers above were evaluated for exon skipping efficacy by treating RD cells at the various indicated concentrations. In these experiments, published antisense oligomers corresponding to H44A(-06+14) and H44A(+85+104) (U.S. Pat. No. 8,232,384, SEQ ID NOs: 167 and 165, respectively) and H44A(-06+20), H44A(-09+17), H44A(+59+85) and H44A(+65+90) (WO2011/057350; SEQ ID NOs: 68, 220, 54 and 10, respectively) were used as comparative oligomers. As shown in FIG. 3, oligomer H44A(-07+17) (SEQ ID NO: 1) was highly effective at inducing exon 44 skipping in RD cells compared to known sequences. As shown in FIG. 4, H44A(+62+89) (SEQ ID NO: 6) was highly effective in inducing exon 44 skipping in cultured RD cells compared to other highly active antisense oligonucleotides known in the art.

All publications and patent applications cited in this specification are herein incorporated by reference as if each individual publication or patent application were specifically and individually indicated to be incorporated by reference.

REFERENCES

Aartsma-Rus, A., A. A. Janson, et al. (2004). "Antisense-induced multiexon skipping for Duchenne muscular dystrophy makes more sense." *Am J Hum Genet* 74(1): 83-92.

Cirak, S., V. Arechavala-Gomeza, et al. (2011). "Exon skipping and dystrophin restoration in patients with Duchenne muscular dystrophy after systemic phosphorodiamidate morpholino oligomer treatment: an open-label, phase 2, dose-escalation study." *Lancet* 378(9791): 595-605.

Dunckley, M. G., I. C. Eperon, et al. (1997). "Modulation of splicing in the DMD gene by antisense oligoribonucleotides." *Nucleosides & Nucleotides* 16(7-9): 1665-1668.

Dunckley, M. G., M. Manoharan, et al. (1998). "Modification of splicing in the dystrophin gene in cultured Mdx muscle cells by antisense oligoribonucleotides." *Hum Mol Genet* 7(7): 1083-90.

Errington, S. J., C. J. Mann, et al. (2003). "Target selection for antisense oligonucleotide induced exon skipping in the dystrophin gene." *J Gene Med* 5(6): 518-27.

Goemans, N. M., M. Tulinius, et al. (2011). "Systemic Administration of PRO051 in Duchenne's Muscular Dystrophy." *N Engl J Med*.

Jearawiriyapaisarn, N., H. M. Moulton, et al. (2008). "Sustained Dystrophin Expression Induced by Peptide-conjugated Morpholino Oligomers in the Muscles of mdx Mice." *Mol Ther*.

Kinali, M., V. Arechavala-Gomeza, et al. (2009). "Local restoration of dystrophin expression with the morpholino oligomer AVI-4658 in Duchenne muscular dystrophy: a single-blind, placebo-controlled, dose-escalation, proof-of-concept study." *Lancet Neurol* 8(10): 918-28.

Lu, Q. L., C. J. Mann, et al. (2003). "Functional amounts of dystrophin produced by skipping the mutated exon in the mdx dystrophic mouse." *Nat Med* 9(8): 1009-14.

Mann, C. J., K. Honeyman, et al. (2002). "Improved antisense oligonucleotide induced exon skipping in the mdx mouse model of muscular dystrophy." *J Gene Med* 4(6): 644-54.

Marshall, N. B., S. K. Oda, et al. (2007). "Arginine-rich cell-penetrating peptides facilitate delivery of antisense oligomers into murine leukocytes and alter pre-mRNA splicing." *Journal of Immunological Methods* 325(1-2): 114-126.

Matsuo, M., T. Masumura, et al. (1991). "Exon skipping during splicing of dystrophin mRNA precursor due to an intraexon deletion in the dystrophin gene of Duchenne muscular dystrophy kobe." *J Clin Invest* 87(6): 2127-31.

Monaco, A. P., C. J. Bertelson, et al. (1988). "An explanation for the phenotypic differences between patients bearing partial deletions of the DMD locus." *Genomics* 2(1): 90-5.

Pramono, Z. A., Y. Takeshima, et al. (1996). "Induction of exon skipping of the dystrophin transcript in lymphoblastoid cells by transfecting an antisense oligodeoxynucleotide complementary to an exon recognition sequence." *Biochem Biophys Res Commun* 226(2): 445-9.

Sazani, P., R. Kole, et al. (2007). Splice switching oligomers for the TNF superfamily receptors and their use in treatment of disease. PCT WO2007058894, University of North Carolina Sierakowska, H., M. J. Sambade, et al. (1996). "Repair of thalassemic human beta-globin mRNA in mammalian cells by antisense oligonucleotides." *Proc Natl Acad Sci USA* 93(23): 12840-4.

Summerton, J. and D. Weller (1997). "Morpholino antisense oligomers: design, preparation, and properties." *Antisense Nucleic Acid Drug Dev* 7(3): 187-95.

Takeshima, Y., H. Nishio, et al. (1995). "Modulation of in vitro splicing of the upstream intron by modifying an intra-exon sequence which is deleted from the dystrophin gene in dystrophin Kobe." *J Clin Invest* 95(2): 515-20.

van Deutekom, J. C., M. Bremmer-Bout, et al. (2001). "Antisense-induced exon skipping restores dystrophin expression in DMD patient derived muscle cells." *Hum Mol Genet* 10(15): 1547-54.

van Deutekom, J. C., A. A. Janson, et al. (2007). "Local dystrophin restoration with antisense oligonucleotide PRO051." *N Engl J Med* 357(26): 2677-86.

Wilton, S. D., A. M. Fall, et al. (2007). "Antisense oligonucleotide-induced exon skipping across the human dystrophin gene transcript." *Mol Ther* 15(7): 1288-96.

Wilton, S. D., F. Lloyd, et al. (1999). "Specific removal of the nonsense mutation from the mdx dystrophin mRNA using antisense oligonucleotides." *Neuromuscul Disord* 9(5): 330-8.

Wu, B., H. M. Moulton, et al. (2008). "Effective rescue of dystrophin improves cardiac function in dystrophin-deficient mice by a modified morpholino oligomer." *Proc Natl Acad Sci USA* 105(39): 14814-9.

Yin, H., H. M. Moulton, et al. (2008). "Cell-penetrating peptide-conjugated antisense oligonucleotides restore systemic muscle and cardiac dystrophin expression and function." *Hum Mol Genet* 17(24): 3909-18.

SEQUENCE LISTING

| Description | Sequence | SEQ ID NO |
|---|---|---|
| H44A(-07+17) | CAGATCTGTCAAATCGCCTGCAGG | 1 |
| H44A(-07+20) | CAACAGATCTGTCAAATCGCCTGCAGG | 2 |
| H44A(-07+22) | CTCAACAGATCTGTCAAATCGCCTGCAGG | 3 |
| H44A(+77+101) | GTGTCTTTCTGAGAAACTGTTCAGC | 4 |
| H44A(+64+91) | GAGAAACTGTTCAGCTTCTGTTAGCCAC | 5 |
| H44A(+62+89) | GAAACTGTTCAGCTTCTGTTAGCCACTG | 6 |
| H44A(+62+85) | CTGTTCAGCTTCTGTTAGCCACTG | 7 |
| H44A(-06+14) | ATCTGTCAAATCGCCTGCAG | 8 |
| H44A(+85+104) | TTTGTGTCTTTCTGAGAAAC | 9 |
| H44A(+61+84) | TGTTCAGCTTCTGTTAGCCACTGA | 10 |
| H44A(-10+15) | GATCTGTCAAATCGCCTGCAGGTAA | 11 |
| H44A(+64+88) | AAACTGTTCAGCTTCTGTTAGCCAC | 12 |
| H44A(+79+103) | TTGTGTCTTTCTGAGAAACTGTTCA | 13 |
| H44A(-06+20) | CAACAGATCTGTCAAATCGCCTGCAG | 14 |
| H44A(-09+17) | CAGATCTGTCAAATCGCCTGCAGGTA | 15 |
| H44A(+59+85) | CTGTTCAGCTTCTGTTAGCCACTGATT | 16 |
| H44A(+59+89) | GAAACTGTTCAGCTTCTGTTAGCCACTGATT | 17 |
| H44A(+65+90) | AGAAACTGTTCAGCTTCTGTTAGCCA | 18 |
| rTAT | RRRQRRKKR | 19 |
| Tat | RKKRRQRRR | 20 |
| R9F2 | RRRRRRRRRFF | 21 |
| R5F2R4 | RRRRRFFRRRR | 22 |
| R4 | RRRR | 23 |
| R5 | RRRRR | 24 |
| R6 | RRRRRR | 25 |
| R7 | RRRRRRR | 26 |
| R8 | RRRRRRRR | 27 |
| R9 | RRRRRRRRR | 28 |

| SEQUENCE LISTING | | |
|---|---|---|
| Description | Sequence | SEQ ID NO |
| (RX)$_8$ | RXRXRXRXRXRXRXRX | 29 |
| (RAhxR)$_4$; (P007) | RAhxRRAhxRRAhxRRAhxR | 30 |
| (RAhxR)$_5$; (CP04057) | RAhxRRAhxRRAhxRRAhxRRAhxR | 31 |
| (RAhxRRBR)$_2$, (CP06062) | RAhxRRBRRAhxRRBR | 32 |

| SEQUENCE LISTING | | |
|---|---|---|
| Description | Sequence | SEQ ID NO |
| (RAR)$_4$F$_2$ | RARRARRARRARFF | 33 |
| (RGR)$_4$F$_2$ | RGRRGRRGRRGRFF | 34 |
| Primer | CTTGGACAGAACTTACCGACTGG | 35 |
| Primer | GTTTCTTCCAAAGCAGCCTCTCG | 36 |
| Primer | GCAGGATTTGGAACAGAGGCG | 37 |
| Primer | CATCTACATTTGTCTGCCACTGG | 38 |

We claim:

1. A method of treating Duchenne muscular dystrophy, comprising administering to a patient in need thereof an effective amount of an antisense oligonucleotide of 28 bases comprising the base sequence of SEQ ID NO: 6, wherein the oligonucleotide specifically hybridizes to an exon 44 target region of the Dystrophin pre-mRNA and induces exon 44 skipping, wherein the antisense oligonucleotide is a morpholino antisense oligonucleotide and wherein the thymine bases are optionally uracil bases;

or a pharmaceutically acceptable salt thereof.

2. The method of claim 1, wherein the antisense oligonucleotide is chemically linked to one or more moieties or conjugates that enhance the activity, cellular distribution, or cellular uptake of the antisense oligonucleotide.

3. The method of claim 1, wherein the antisense oligonucleotide is chemically linked to a polyethylene glycol moiety.

4. The method of claim 1, wherein the antisense oligonucleotide is administered intravenously.

* * * * *